(12) United States Patent
Chaulagain et al.

(10) Patent No.: US 12,091,466 B2
(45) Date of Patent: Sep. 17, 2024

(54) ANTI-CD38 ANTIBODIES FOR TREATMENT OF LIGHT CHAIN AMYLOIDOSIS AND OTHER CD38-POSITIVE HEMATOLOGICAL MALIGNANCIES

(71) Applicants: Janssen Biotech, Inc., Horsham, PA (US); Tufts Medical Center, Inc., Boston, MA (US)

(72) Inventors: Chakra Chaulagain, Broward, FL (US); Raymond Comenzo, Boston, MA (US); Parul Doshi, Spring House, PA (US); Xun Ma, Boston, MA (US); Amy Sasser, Spring House, PA (US)

(73) Assignees: JANSSEN BIOTECH, INC., Horsham, PA (US); TUFTS MEDICAL CENTER, INC., Boston, MA (US)

(*) Notice: Subject to any disclaimer, the term of this patent is extended or adjusted under 35 U.S.C. 154(b) by 721 days.

(21) Appl. No.: 16/986,214

(22) Filed: Aug. 5, 2020

(65) Prior Publication Data
US 2020/0407459 A1    Dec. 31, 2020

Related U.S. Application Data

(63) Continuation of application No. 15/160,476, filed on May 20, 2016, now Pat. No. 10,766,965.

(60) Provisional application No. 62/214,586, filed on Sep. 4, 2015, provisional application No. 62/164,206, filed on May 20, 2015.

(51) Int. Cl.
| | | |
|---|---|---|
| C07K 16/28 | (2006.01) |
| A61K 9/00 | (2006.01) |
| A61K 31/573 | (2006.01) |
| A61K 31/664 | (2006.01) |
| A61K 31/69 | (2006.01) |
| A61K 38/05 | (2006.01) |
| A61K 38/47 | (2006.01) |
| A61K 39/395 | (2006.01) |
| A61K 45/06 | (2006.01) |
| A61K 39/00 | (2006.01) |

(52) U.S. Cl.
CPC ........ *C07K 16/2896* (2013.01); *A61K 9/0019* (2013.01); *A61K 31/573* (2013.01); *A61K 31/664* (2013.01); *A61K 31/69* (2013.01); *A61K 38/05* (2013.01); *A61K 38/47* (2013.01); *A61K 39/3955* (2013.01); *A61K 45/06* (2013.01); *C12Y 302/01035* (2013.01); *A61K 2039/505* (2013.01); *C07K 2317/21* (2013.01); *C07K 2317/24* (2013.01); *C07K 2317/56* (2013.01); *C07K 2317/565* (2013.01); *C07K 2317/732* (2013.01)

(58) Field of Classification Search
CPC ............ C07K 16/2896; A61K 39/3955; A61K 2039/505; A61K 31/69; A61K 31/573; A61K 31/664
See application file for complete search history.

(56) References Cited

U.S. PATENT DOCUMENTS

| | | |
|---|---|---|
| 6,737,056 B1 | 5/2004 | Presta |
| 7,183,387 B1 | 2/2007 | Presta |
| 7,223,397 B1 | 5/2007 | Rosenblum et al. |
| 7,829,673 B2 | 11/2010 | DeWeers |
| 7,829,693 B2 | 11/2010 | Kreutzer et al. |
| 8,008,449 B2 | 8/2011 | Korman et al. |
| 8,088,896 B2 | 1/2012 | Tesar et al. |
| 8,153,765 B2 | 4/2012 | Park et al. |
| 8,318,154 B2 | 11/2012 | Frost et al. |
| 8,354,509 B2 | 1/2013 | Carven et al. |
| 8,431,380 B2 | 4/2013 | Bookbinder et al. |
| 9,040,050 B2 | 5/2015 | Van De Winkel |
| 9,603,927 B2 | 3/2017 | Doshi |
| 9,732,154 B2 | 8/2017 | Doshi |
| 10,385,135 B2 | 8/2019 | Janssen et al. |
| 10,556,961 B2 | 2/2020 | Doshi |
| 10,604,580 B2 | 3/2020 | Lokhorst |
| 10,668,149 B2 | 6/2020 | Doshi et al. |
| 10,766,965 B2 | 9/2020 | Chaulagain |
| 10,781,261 B2 | 9/2020 | Janssen et al. |
| 10,793,630 B2 | 10/2020 | Doshi et al. |
| 10,800,851 B2 | 10/2020 | Doshi |
| 11,021,543 B2 | 6/2021 | Ahmadi et al. |
| 11,566,079 B2 | 1/2023 | Jansson et al. |
| 11,618,787 B2 | 4/2023 | Ahmadi |
| 11,634,499 B2 | 4/2023 | Larmore |
| 11,708,419 B2 | 7/2023 | Jansson et al. |
| 11,708,420 B2 | 7/2023 | Jansson et al. |

(Continued)

FOREIGN PATENT DOCUMENTS

| | | |
|---|---|---|
| AU | 2013203186 A1 | 5/2013 |
| CL | 2013001944 A1 | 9/2014 |

(Continued)

OTHER PUBLICATIONS

"A Prospective Phase II of Daratumumab in Previously Treated Systemic Light Chain (AL) Amyloidosis", published online at //cms.cws.net/content/beta.myelomasociety.org/files/2017ash/Roussel,%20Murielle-ASH2017.pdf (2017).

(Continued)

*Primary Examiner* — Jessica H Roark
(74) *Attorney, Agent, or Firm* — Hamilton, Brook, Smith & Reynolds, P.C.; Deirdre E. Sanders

(57) ABSTRACT

The present invention relates to methods of treatment of light chain amyloidosis and other CD38-positive hematological malignancies with anti-CD38 antibodies.

18 Claims, 12 Drawing Sheets

Specification includes a Sequence Listing.

(56) References Cited

U.S. PATENT DOCUMENTS

| | | |
|---|---|---|
| 11,713,355 B2 | 8/2023 | Doshi et al. |
| 11,732,051 B2 | 8/2023 | Jansson et al. |
| 2004/0141982 A1 | 7/2004 | Lust et al. |
| 2004/0268425 A1 | 12/2004 | Bookbinder et al. |
| 2006/0257397 A1 | 11/2006 | Throsby |
| 2007/0148178 A1 | 6/2007 | Fyfe et al. |
| 2008/0063642 A1 | 3/2008 | Adelman et al. |
| 2008/0166344 A1 | 7/2008 | Nakahara et al. |
| 2009/0076249 A1 | 3/2009 | Deweers et al. |
| 2009/0148449 A1 | 6/2009 | DeWeers |
| 2009/0304687 A1 | 12/2009 | Drachman |
| 2009/0304710 A1 | 12/2009 | Park et al. |
| 2010/0068136 A1 | 3/2010 | Hansen |
| 2010/0074885 A1 | 3/2010 | Schiff et al. |
| 2010/0092489 A1 | 4/2010 | van de Winkel et al. |
| 2010/0285004 A1 | 11/2010 | Tesar et al. |
| 2011/0044977 A1 | 2/2011 | Adler et al. |
| 2011/0053247 A1 | 3/2011 | Baker et al. |
| 2011/0066111 A1 | 3/2011 | Teschner et al. |
| 2011/0076273 A1 | 3/2011 | Adler et al. |
| 2011/0099647 A1 | 4/2011 | De Weers et al. |
| 2011/0210017 A1 | 9/2011 | Lai et al. |
| 2011/0293606 A1 | 12/2011 | Lejeune |
| 2011/0300157 A1 | 12/2011 | Devy et al. |
| 2012/0171153 A1 | 7/2012 | Frost |
| 2012/0201827 A1 | 8/2012 | Elias |
| 2012/0219551 A1 | 8/2012 | Johnson et al. |
| 2012/0231008 A1 | 9/2012 | Guo et al. |
| 2012/0244110 A1 | 9/2012 | Chen et al. |
| 2012/0258081 A1 | 10/2012 | Corringham et al. |
| 2012/0259095 A1 | 10/2012 | Beliard et al. |
| 2012/0295864 A1 | 11/2012 | Taube et al. |
| 2013/0022588 A1 | 1/2013 | Yang et al. |
| 2013/0109593 A1 | 5/2013 | Hartmann et al. |
| 2013/0137134 A1 | 5/2013 | Mordechai et al. |
| 2013/0209355 A1 | 8/2013 | De Weers et al. |
| 2013/0302400 A1 | 11/2013 | Maneval et al. |
| 2013/0309250 A1 | 11/2013 | Cogswell et al. |
| 2013/0323247 A1 | 12/2013 | Zugmaier et al. |
| 2014/0051662 A1 | 2/2014 | Moussy |
| 2014/0099254 A1 | 4/2014 | Chang et al. |
| 2014/0155584 A1 | 6/2014 | Elias et al. |
| 2014/0248238 A1 | 9/2014 | Wilson et al. |
| 2014/0271644 A1 | 9/2014 | Elias et al. |
| 2014/0309183 A1 | 10/2014 | Kerr |
| 2014/0314800 A1 | 10/2014 | Mathieu et al. |
| 2014/0356318 A1 | 12/2014 | Barken |
| 2015/0118251 A1 | 4/2015 | Deslandes |
| 2015/0125447 A1 | 5/2015 | Heider |
| 2015/0231235 A1 | 8/2015 | Van De Winkel |
| 2015/0246123 A1 | 9/2015 | Doshi |
| 2015/0246975 A1 | 9/2015 | Doshi |
| 2015/0376276 A1 | 12/2015 | Lewis et al. |
| 2016/0009683 A1 | 1/2016 | Hansen et al. |
| 2016/0067205 A1 | 3/2016 | Lokhorst |
| 2016/0168228 A1 | 6/2016 | Despanie |
| 2016/0222106 A1 | 8/2016 | Doshi et al. |
| 2016/0367663 A1 | 12/2016 | Doshi et al. |
| 2016/0376373 A1 | 12/2016 | Ahmadi |
| 2017/0008966 A1 | 1/2017 | Chaulagain |
| 2017/0044265 A1 | 2/2017 | Ahmadi |
| 2017/0107295 A1 | 4/2017 | Lokhorst |
| 2017/0121414 A1 | 5/2017 | Jansson et al. |
| 2017/0121417 A1 | 5/2017 | Jansson et al. |
| 2017/0174780 A1 | 6/2017 | Doshi |
| 2017/0320961 A1 | 11/2017 | Doshi |
| 2018/0117150 A1 | 5/2018 | O'Dwyer |
| 2019/0127479 A1 | 5/2019 | Ahmadi et al. |
| 2019/0144557 A1 | 5/2019 | Ahmadi et al. |
| 2019/0233533 A1 | 8/2019 | Otten |
| 2019/0330363 A1 | 10/2019 | Janssen et al. |
| 2019/0352421 A1 | 11/2019 | Adams et al. |
| 2020/0002433 A1 | 1/2020 | Janssen et al. |
| 2020/0121588 A1 | 4/2020 | Campbell et al. |
| 2020/0148782 A1 | 5/2020 | Jansson et al. |
| 2020/0223936 A1 | 7/2020 | Doshi et al. |
| 2020/0231697 A1 | 7/2020 | Jansson et al. |
| 2020/0268847 A1 | 8/2020 | Qi |
| 2020/0308284 A1 | 10/2020 | Bandekar et al. |
| 2020/0308296 A1 | 10/2020 | Bandekar et al. |
| 2020/0316197 A1 | 10/2020 | Bandekar et al. |
| 2020/0330593 A1 | 10/2020 | Bandekar et al. |
| 2020/0339701 A1 | 10/2020 | Jansson et al. |
| 2020/0392242 A1 | 12/2020 | Liu |
| 2020/0397896 A1 | 12/2020 | Liu |
| 2020/0405854 A1 | 12/2020 | Liu |
| 2021/0047401 A1 | 2/2021 | Doshi et al. |
| 2021/0061920 A1 | 3/2021 | Doshi et al. |
| 2021/0095042 A1 | 4/2021 | Jansson et al. |
| 2021/0107991 A1 | 4/2021 | Jansson et al. |
| 2021/0403592 A1 | 12/2021 | Ahmadi et al. |
| 2022/0041745 A1 | 2/2022 | Bandekar et al. |
| 2022/0062415 A1 | 3/2022 | Xie et al. |
| 2022/0204638 A1 | 6/2022 | Liu et al. |
| 2022/0275090 A1 | 9/2022 | Alvarez Arias |
| 2022/0275101 A1* | 9/2022 | Schecter ............ C07K 16/2896 |
| 2022/0401465 A1 | 12/2022 | Fan et al. |
| 2023/0340145 A1 | 10/2023 | Ahmadi et al. |
| 2023/0391884 A1 | 12/2023 | Otten |
| 2024/0092927 A1 | 3/2024 | Jansson et al. |

FOREIGN PATENT DOCUMENTS

| | | |
|---|---|---|
| CL | 2016002158 A1 | 7/2017 |
| EA | 009383 B1 | 12/2007 |
| EA | 015584 B1 | 10/2011 |
| EA | 201390993 | 12/2013 |
| EP | 2561868 A1 | 2/2013 |
| EP | 2567976 A2 | 3/2013 |
| EP | 2 459 167 B1 | 5/2013 |
| EP | 2 477 603 B1 | 3/2016 |
| NZ | 576122 | 9/2012 |
| WO | WO 89/08114 A1 | 9/1989 |
| WO | WO 92/01049 A2 | 1/1992 |
| WO | WO 94/17184 A1 | 8/1994 |
| WO | WO 96/16990 A1 | 6/1996 |
| WO | WO 98/16245 A1 | 4/1998 |
| WO | WO 98/16254 A1 | 4/1998 |
| WO | WO 98/50435 A1 | 11/1998 |
| WO | WO 99/62526 A2 | 12/1999 |
| WO | WO 00/06194 A2 | 2/2000 |
| WO | WO 00/40265 A1 | 7/2000 |
| WO | WO 2001/060803 | 8/2001 |
| WO | WO 01/97844 A1 | 12/2001 |
| WO | WO 02/06347 A1 | 1/2002 |
| WO | WO 02/32288 A2 | 4/2002 |
| WO | WO 2003/106498 A2 | 12/2003 |
| WO | WO 2004/058288 A1 | 7/2004 |
| WO | WO 2004/078140 A2 | 9/2004 |
| WO | WO 2004/092160 A1 | 10/2004 |
| WO | WO 2005/042019 A1 | 5/2005 |
| WO | WO 2005/044855 A2 | 5/2005 |
| WO | WO 2005/063819 A2 | 7/2005 |
| WO | WO 2005/103083 A2 | 11/2005 |
| WO | WO 2006/088951 A2 | 8/2006 |
| WO | WO 2006/099875 A1 | 9/2006 |
| WO | WO 2006/125640 A2 | 11/2006 |
| WO | WO 2007/042309 A2 | 4/2007 |
| WO | WO 2008/037257 A2 | 4/2008 |
| WO | WO 2008/047242 A2 | 4/2008 |
| WO | WO 2008/073160 A2 | 6/2008 |
| WO | WO 2008/116103 A2 | 9/2008 |
| WO | WO 2008/121615 A2 | 10/2008 |
| WO | WO 2008/150530 A2 | 12/2008 |
| WO | WO 2009/062054 A1 | 5/2009 |
| WO | WO 2009/118142 A2 | 10/2009 |
| WO | WO 2009/128917 | 10/2009 |
| WO | WO 2010/052014 | 5/2010 |
| WO | WO 2010/061357 A1 | 6/2010 |
| WO | WO 2010/061358 A1 | 6/2010 |
| WO | WO 2010/061359 A1 | 6/2010 |
| WO | WO 2010/061360 A1 | 6/2010 |
| WO | WO 2011/012637 A2 | 2/2011 |
| WO | WO 2011/029892 A2 | 3/2011 |

(56) References Cited

FOREIGN PATENT DOCUMENTS

| | | |
|---|---|---|
| WO | WO 2011/109365 A2 | 9/2011 |
| WO | WO 2011/154453 A1 | 12/2011 |
| WO | WO 2012/041800 A1 | 4/2012 |
| WO | WO 2012/076663 A1 | 6/2012 |
| WO | WO 2012/092612 A1 | 7/2012 |
| WO | WO 2012/092616 A1 | 7/2012 |
| WO | WO 2013/059885 A2 | 5/2013 |
| WO | WO 2013/102144 A2 | 7/2013 |
| WO | WO 2013/164837 A1 | 11/2013 |
| WO | WO 2014/048921 A1 | 4/2014 |
| WO | WO 2014/068114 A1 | 5/2014 |
| WO | WO 2014/089416 A1 | 6/2014 |
| WO | WO 2014/142220 A1 | 9/2014 |
| WO | WO 2014/178820 A1 | 11/2014 |
| WO | WO 2015/009726 A2 | 1/2015 |
| WO | WO 2015/066450 A1 | 7/2015 |
| WO | WO 2015/121454 A1 | 8/2015 |
| WO | WO 2015/130728 A1 | 9/2015 |
| WO | WO 2015/130732 A2 | 9/2015 |
| WO | WO 2015/195555 A1 | 12/2015 |
| WO | WO 2015/195556 A1 | 12/2015 |
| WO | WO 2016/040294 A2 | 3/2016 |
| WO | WO 2016/089960 A1 | 6/2016 |
| WO | WO 2016/133903 A2 | 8/2016 |
| WO | WO 2016/187546 A1 | 11/2016 |
| WO | WO 2016/209921 A1 | 12/2016 |
| WO | WO 2016/210223 A1 | 12/2016 |
| WO | WO 2017/004266 A1 | 1/2017 |
| WO | WO 2017/079150 A1 | 5/2017 |
| WO | WO 2018/002181 A1 | 1/2018 |
| WO | WO 2018/213732 A1 | 11/2018 |
| WO | WO 2019/089832 A1 | 5/2019 |
| WO | WO 2019/186273 A1 | 10/2019 |
| WO | WO 2020/243911 A1 | 12/2020 |

OTHER PUBLICATIONS

Aarhust, et al., "ADP-ribosyl Cyclase and CD38 Catalyze the Synthesis of a Calcium mobilizing Metabolite from NADP+," The Journal of Biological Chemistry, 270(51): 30327-30333 (1995).

Abdi, J. et al., "Drug resistance in multiple myeloma: latest findings and new concepts on molecular mechanisms," Oncotarget, vol. 4; No. 12; 2186-2207 (2013).

Adriouch et al., "Extracellular NAD+: a danger signal hindering regulatory T cells," Microbes and Infection, 14:1284-1292 (2012).

Agheli, A. et al., "A Rare Case of Primary Amyloidosis, Presenting with Severe Pulmonary Hypertension and Bilateral Pleural Effusion," Blood, vol. 106: p. 5100 (2005).

Almagro, J.C. and Fransson, J., "Humanization of antibodies," Frontiers in Bioscience, vol. 13; 1619-1633 (2008).

Arican, et al., "Philadelphia Chromosome (+) T-Cell Acute Lymphoblastic Leukemia After Renal Transplantation," Transplantation Proceedings, vol. 31; 3242-3243 (1999).

Armitage et al., "Long-Term Remission Durability and Functional Status of Patients Treated for Diffuse Histiocytic Lymphoma with the CHOP Regimen," J. Clin. Oncol. 2:898-902, (1984).

Arthur, "Innovations in subcutaneous infusions," J. Infus. Nurs. 38(3); 179-87; May/Jun. 2015.

Bachireddy, et al., "Haematologic Malignancies: at the Forefront of Immunotherapeutic Innovation," Nature Reviews Cancer, vol. 15, No. 4, pp. 201-215, Apr. 1, 2015 (Apr. 1, 2015).

Bahlis, N.J. et al., "Daratumumab, lenalidomide, and dexamethasone (DRd) vs lenalidomide and dexamethasone (Rd) in relapsed or refractory multiple myeloma (RRMM): Efficacy and safety updated (POLLUX)," Journal of Clinical Oncology, vol. 35; No. 15; 8025; Abstract (2017).

Berglund, L. et al., "The epitope space of the human proteome," Protein Science, vol. 17; 606-613 (2008).

Blankestijn, et al., "Could daratumumab be used to treat severe allergy?," Journal of Allergy and Clinical Immunology, Elsevier, Amsterdam, NL, vol. 139, No. 5, p. 1677-1678, Jan. 19, 2017.

Brand, F-X. et al., "Prospect for Anti-HER2 Receptor Therapy in Breast Cancer," AntiCancer Research, vol. 26; 463-470 (2006).

Brown, et al., "Tolerance of single, but not multiple, amino acid replacements in antibody VH CDR 2: a means of minimizing B cell wastage from somatic hypermutation?" The Journal of Immunology, 156: 3285-3291 (1996).

Carter et al., "Identification and validation of cell surface antigens for antibody targeting in oncology," Endocrine-Related Cancer, vol. 11, pp. 659-687, (2004).

Chari et al., "Subcutaneous Delivery of Daratumumab in Patients with Relapsed or Refractory Multiple Myeloma (RRMM): PAVO, an Open-label, Multicenter, Dose Escalation Phase 1b Study," American Society of Hematology, Clinical Trials.gov Identifier NCTO2519452, Dec. 2017.

Chari A. et al., "Subcutaneous delivery of daratumumab in patients (pts) with relapsed or refractory multiple myeloma (RRMM): PAVO, an openlabel, multicenter, dose escalation phase 1b study," 2017 ASH Annual Meeting *ANZMAP Multiple Myeloma Highlights*, 2017.

Chaulagain, C.P., et al., "How we Treat Systemic Light-Chain Amyloidosis," Clinical Advances in Hematology & Oncology, vol. 13; No. 5; 315-324 (2015).

Chaulagain, C.P. and Comenzo, R.L., "New Insights and Modern Treatment of AL Amyloidosis," Curr Hematol Malig Rep, vol. 8; 291-298 (2013).

Chen, et al., "Selection and Analysis of an Optimized Anti-VEGF Antibody: Crystal Structure of an Affinity-matured Fab in Complex with Antigen," Journal of Molecular Biology, 293: 865-881 (1999).

Cheson et al., "Revised Response Criteria for Malignant Lymphoma," Journal of Clinical Oncology, vol. 25, No. 5, 579-586 (Feb. 10, 2007).

Chiarugi, A. et al., "The NAD metabolome—a key determinant of cancel cell biology," Nature Reviews, vol. 12; 741-752 (2012).

Chillemi, A. et al., "Anti-CD38 Antibody Therapy: Windows of Opportunity Yielded by the Functional Characteristics of the Target Molecule," Molecular Medicine, vol. 19; 99-108 (2013).

Chou, et al., "Drug Combination Studies and their Synergy Quantification Using the Chou-Talalay Method," Cancer Research, 70(2): 440-446 (2010).

ClinicalTrials.gov, "Daratumumab in Combination with ATRA (DARA/ATRA)," Identifier: NCT02751255; First posted: Apr. 26, 2016 (11 pages).

ClinicalTrials.gov "Study of YM155 in Refractory Diffuse Large B-cell Lymphoma (DLBCL) Subjects," Interventional Studies, U.S. National Library of Medicine, //clinicaltrials.gov/ct2/show/record/NCT00498914, First posted Jul. 11, 2007 [retrieved on Sep. 10, 2018] (14 pages).

ClinicalTrials.gov, "A Study of Daratumumab with the Addition of Recombinant Human Hyaluronidase (rHuPH20) for the Treatment of Participants with Relapsed or Refractory Multiple Myeloma," Identifier: NCT02519452; First Posted: Aug. 11, 2015 (13 pages).

ClinicalTrials.gov, "A Study to Evaluate Subcutaneous Daratumumab in Combination with Standard Multiple Myeloma Treatment Regimens," Identifier: NCT03412565, First Posted: Jan. 26, 2018 (16 pages).

ClinicalTrials.gov, "A Phase 1 Study to Assess the Safety, Tolerability, and Pharmacokinetics of TAK-079 in Healthy Participants," Identifier: NCT02219256, 13 pages; Latest version posted: Mar. 22, 2017. (13 pages).

Colman, "Effects of amino acid sequence changes on antibody-antigen interactions, A Structural View of Immune Recognition by Antibodies," Biomolecular Research Institute, 33-36, (1994).

Comenzo, R.L. et al., "Consensus guidelines for the conduct and reporting of clinical trials in systemic light-chain amyloidosis," Leukemia, vol. 26; 2317-2325 (2012).

Cotner, et al., "Human T Cell Proteins Recognized by Rabbit Heteroantisera and Monoclonal Antibodies," International Journal of Immunopharmaceuticals, 3(3): 255-268 (1981).

Data show daratumumab achieved a pronounced overall response rate as a single-agent with tolerable safety profile in heavily pre-treated multiple myeloma patients, Johnson & Johnson Press release[online] (retrived on Jul. 27, 2020), May 30, 2015, retrieved from the Internet<URL:https://www.jnj.com/media-center/press-

(56) References Cited

OTHER PUBLICATIONS releases/Data-show-daratumumab-achieved-a-pronounced-overall-response-rate-as-a-single-agent-with-tolerable-safety-profile-in-heavily-pre-treated-multiple-myeloma-patients>; 4 pages.

Davies, et al., "Affinity improvement of single antibody VH domains: residues in all three hypervariable regions affect antigen binding," Immunotechnology, 2: 169-179 (1996).

Davis, et al., "Transgenic mice as a source of fully human antibodies for the treatment of cancer," Cancer and Metastasis Reviews, 18: 421-425 (1999).

Deckert, et al., "SAR650984, A Novel Humanized CD38-Targeting Antibody, Demonstrates Potent Antitumor Activity in Models of Multiple Myeloma and Other CD38B Hematologic Malignancies," Clinical Cancer Research. vol. 20, No. 17, pp. 4574-4583 (2014).

Dennis, "Off by a Whisker," Nature, 442 (17): 749-741 (2006).

Depascalis, et al., "Grafting of 'Abbreviated' Complementarity-Determining Regions Containing Specificity-Determining Residues Essential for Ligand Contact to Engineer a Less Immunogenic Humanized Monoclonal Antibody," The Journal of Immunology, 169: 3076-3084 (2002).

De Haart, S.J. et al., "Accessory Cells of the Microenvironment Protect Multiple Myeloma from T-Cell Cytotoxicity through Cell Adhesion-Mediated Immune Resistance," Clinical Cancer Research, vol. 19; No. 20; 5591-5601 (2013).

De Weers, et al., "Daratumumab, a Novel Therapeutic Human CD38 Monoclonal Antibody, Induces Killing of Multiple Myeloma and Other Hematological Tumors," The Journal of Immunology, 186: 1840-1848 (Pre-published online Dec. 27, 2010).

De Weers, M. et al., "Humax-CD38, a New Human CD38 Monoclonal Antibody, Effectively Mediates Killing of Multiple Myeloma and Plasma Cell Leukemia Cells," abstract, Submitted for the 16$^{th}$ European Congress of Immunology—ECI2006, Paris, France, [Sep. 6-9, 2006].

De Weers et al., "HuMax-CD38, a new human CD38 monoclonal antibody, effectively mediates killing of multiple myeloma and plasma cell leukemia cells," The 23$^{rd}$ International Conference on 'Advances in the Application of Monoclonal Antibodies in Clinical Oncology, (Jun. 26-28, 2006), Royal Myconian Resort & Thalasso Spa Center, Mykonos, Greece (Abstract).

Dimopoulos, M.A. et al., "Daratumumab, Lenalidomide, and Dexamethasone for Multiple Myeloma," The New England Journal of Medicine, vol. 375; No. 14; 1319-1331 (2016).

Dimopoulos, M.A. et al., "Daratumumab plus lenalidomide and dexamethasone versus lenalidomide and dexamethasone in relapsed or refractory multiple myeloma: updated analysis of POLLUX," Haematologica, vol. 103; No. 12; 2088-2096 (2018).

Dispenzieri, A. et al., "Treatment of Immunoglobulin Light Chain Amyloidosis: Mayo Stratification of Myeloma and Risk-Adapted Therapy (mSMART) Consensus Statement," Mayo Clin Proc., vol. 90; No. 8; 1054-1081 (2015).

DMC recommends termination of study into daratumumab with atezolizumab to treat NSCLC, European Pharmaceutic Manufacturer[online](retrieved on Jul. 26, 2020), May 30, 2018, retrieved from the Internet<URL:https://www.epmmagazine.com/news/dmc-recommends-termination-of-study-into-daratumumab/>; 3 pages.

Dos Santos, et al., Anti-Leukemic Activity of Daratumumab in Acute Myeloid Leukemia Cells and Patient-Derived Xenografts, Blood, vol. 124, Abstract 2312, (2014).

Doshi, et al., "Daratumumab Treatment in Combination with Chop or R-Chop Results in the Inhibition or Regression of Tumors in Preclinical Models of Non-Hodgkins Lymphoma," Haematologica, The Hematology Journal, 99(1): 138 (2014).

Eldfors, et al., "Landscape of Mutations in Relapsed Acute Myeloid Leukemia," vol. 124: No. 21, p. 2367; (2014).

Ellis, et al., "Engineered Anti-CD38 Monoclonal Antibodies for Immunotherapy of Multiple Myeloma," The Journal of Immunology, 155: 925-937 (1995).

Engert, et al., "A Phase-I Study of an Anti-CD25 Ricin A-Chain Immunotoxin (RFT5-SMPT-dgA) in Patients with Refractory Hodgkin's Lymphoma," Blood, 89(2): 403-410 (1997).

Ettinger, R. et al., "Pathogenic mechanisms of IgE-mediated inflammation in self-destructive autoimmune responses," Autoimmunity, vol. 50; No. 1; 25-36 (2017).

Ferrero, et al., Characterization and phylogenetic epitope mapping of CD38 ADPR cyclase in the cynomolgus macaque, BMC Immunology, 5(21): 1-13 (2004).

Field-Smith, "Bortezomid (Velcade™) in the treatment of multiple myeloma," Therapeutic and Clinical Risk Management, 2(3): 271-279 (2006).

Flavell, et al., "Therapy of human T-cell acute lymphoblastic leukaemia with a combination of anti-CD7 and anti-CD38-SAPORIN immunotoxins is significantly better than therapy with each individual immunotoxin," Br. J. Cancer, vol. 84, No. 4, pp. 571-578, (2001).

Franco, et al., "The transmembrane glycoprotein CD38 is a catalytically active transporter responsible for generation and influx of the second messenger cyclic ADP-ribose across membranes," FASEB Journal, 12: 1507-1520 (1998).

Fujimori, et al., "A Modeling Analysis of Monoclonal Antibody Percolation Though Tumors: A Binding-Site Barrier," Journal of Nucleic Medicine, 31: 1191-1198 (1990).

Fujioka, Y. and Kurokawa, M., "Follicular lymphoma presenting with massive splenomegaly," International J Hematol, vol. 95; 3-4 (2012).

Funaro et al., "CD38 Functions Are Regulated Through an Internalization Step," Journal of Immunology, 160: 2238-2247 (1998).

Funaro, et al., "Human CD38: a versatile leukocyte molecule with emerging clinical prospectives," Fundamental and Clinical Immunology, 3(3): 101-113 (1995).

Funaro, et al., "Identification and characterization of an active soluble form of human CD38 in normal and pathological fluids," International Immunology, 8(11): 1643-1650 (1996).

Funaro, et al., "Involvement of the Multilineage CD38 Molecule in a Unique Pathway of Cell Activation and Proliferation," The Journal of Immunology, 145: 2390-2396 (1990).

Gallo, et al., "The human immunoglobulin loci introduced into mice: V(D) and J gene segment usage similar to that of adult humans," European Journal of Immunology, 30: 534-540 (2000).

Genmab "Humanx-CD38 Effective in Preclinical Studies," Genmab A/S, Stock Exchange Release 57/2005.

Genmab "Daratumumab Receives Breakthrough Therapy Designation from US Food and Drug Administration", Copenhagen, Denmark; May 1, 2013—Genmab A/S (OMX: GEN) disponible en: http://files.shareholder.com/downloads/AMDA-KPIBN/0x0x659093/64b187b8-830c-4252-acd6-8019b4199069/18%20Daratumumab%20breakthrough%20status_010513_uk.pdf, (May 1, 2013).

Genmab Announces Daratumumab and Ofatumumab Data to Be Presented at American Society of Hematology Annual Meeting (ASH), American Society of Hematology Annual Meeting and Exposition, San Francisco, California, Media Release 06; pp. 1-3 (Nov. 2014).

George, et al., "Differential Effects of Anti-B2-Glycoprotein I Antibodies on Endothelial Cells and on the Manifestations of Experimental Antiphospholipid Syndrome," Circulation, 97: 900-906 (1998).

Goldmacher, et al., "Anti-CD38-Blocked Ricin: An immunotoxin for the Treatment of Multiple Myeloma," The American Society of Hematology, 84(9): 3017-3025 (1994).

Goodwin, "Subcutaneous Daratumumab Potential Game Changer for Multiple Myeloma," Oncology Times, 2017 American Society of Hematology Annual Meeting, p. 49, (2017).

Gopalakrishnan, et al. "Daratumumab improves the anti-myeloma effect of newly emerging multidrug therapies," Blood and Lymphatic Cancer: Targets and Therapy, 3: 19-24 (2013).

Graeff, et al., "Enzymatic Synthesis and Characterizations of Cyclic GDp-ribose," The Journal of Biological Chemistry, 269(48): 30260-30267 (1994).

(56) References Cited

OTHER PUBLICATIONS

Green, "Antibody engineering via genetic engineering of the mouse: XenoMouse strains are a vehicle for the facile generation of therapeutic human monoclonal antibodies," Journal of Immunological Methods, 231: 11-23 (1999).
Green, et al., "Antigen-specific human monoclonal antibodies from mice engineered with hyman Ig heavy and light chain YACs," Nature Genetics, 7: 13-21 (1994).
Gupta, R. et al., "The Economic Impact of Childhood Food Allergy in the United States," JAMA Pediatrics, vol. 167; No. 11; 1026-1031 (2013).
Guse et al., "Regulation of calcium signaling in T lymphocytes by the second messenger cyclic ADP-ribose," Nature 398:70-73, (1999).
Haart, et al., "Sepantronium bromide (YM155) improves daratumumab-mediated cellular lysis of multiple myeloma cells by abrogation of bone marrow stromal cell-induced resistance," Haematologica, Letters to the Editor, vol. 101, No. 8, pp. e339-e343, (2016).
Hara-Yokoyama, "Alteration of enzymatic properties of cell-surface antigen CD38 by agonistic anti-CD38 antibodies that prolong B cell survival and induce activation," International Immunopharmacology, 8: 59-70 (2008).
Hartmann, Radioimmunotherapy of Nude Mice Bearing a Human Interleukin 2 Receptor α-expressing Lymphoma Utilizing the α-emitting Radionuclide-conjugated Monoclonal Antibody 212Bi-anti-Tac, Cancer Research, 54: 4362-4370 (1994).
Henry, et al., "the use of basiliximab in solid organ transplantation," Expert Opinion Pharmacotherapy, 3(10): 1657-1663 (2002).
Holgate, S.T., "New strategies with anti-IgE in allergic diseases," World Allergy Organization Journal, vol. 7; No. 17; 6 pages (2014).
Holm, et al., "Functional mapping and single chain construction of the anti-cytokeratin 8 monoclonal antibody TS1," Molecular Immunology, 44: 1075-1084 (2017).
Hoshino, et al., "Mapping of the Catalylic and Epitopic Sites of Human CD38/NAD+ Glycohydrolase to a Functional Domain in the Carboxyl Terminus1," The Journal of Immunology, 158: 741-747 (1997).
Howard, et al., "Formation and Hydrolysis of Cyclic ADP-Ribose Catalyzed by lymphocyte Antigen CD38," Science, 262(5136): 1056-1059 (1993).
Hu, Y., et al., "Immunophenotypic analysis of abnormal plasma cell clones in bone marrow of primary systemic light chain amyloidosis patients," Chin Med J., vol. 127; No. 15; 2765-2770; Abstract only (2014).
Hu, Y. et al., "The Significance of Abnormal Plasma Cell Clone in Bone Marrow of Primary Systemic Light Chain Amyloidosis Patients," Blood, vol. 122; p. 5342 (2013).
Ikehata, et al., "Autoantibodies against CD38 (ADP-ribosyl Cyclase/Cyclic ADP-ribose Hydrolase) that Impair Glucose-induced Insulin Secretion in Noninsulin-dependent Diabetes Patients," Journal of Clinical Investigations, 102(2): 395-401 (1998).
Inaba, H. et al., "Acute lymphoblastic leukaemia," Lancet, vol. 381; 27 pages (2013).
Jackisch, et al., "Subcutaneous versus intravenous formulation of trastuzumab for HER2-positive early breast cancer: updated results from the phase III HannaH study," Annals of Oncology, vol. 26, pp. 320-325, (2015).
Jackson, et al., "Isolation of a cDNA Encoding The Human CD38 (T10) molecule, A Cell Surface Glycoprotein With An Unusual Discontinuous Pattern of Expression During Lymphocyte Differentiation," The Journal of Immunology, 144(7): 2811-2815 (1990).
Jagannath, et al. Treatment (tx) journeys in newly diagnosed multiple myeloma (NDMM) patients (pts): Results from the Connect MM Registry. Multiple Myeloma Update from the American Society of Clinical Oncology. (ASCO) 41st Annual meeting, (Jun. 4, 2018).
Jakob, et al., "Stage-dependent Expression of CD7, CD45RO, CD45RA and CD25 on CD4-positive Peripheral Blood T-lymphocytes in Cutaneous T-cell Lymphoma," Acta Derm Venerology, 76: 34-36 (1996).
Jakobovits, "the long-awaited magic bullets: therapeutic human monoclonal antibodies from transgenic mice", Expert Opinion on Investigational Drugs, 7(4): 607-614 (1998).
Jang, et al., "The structural basis for DNA binding by an anti-DNA autoantibody," Molecular Immunology, 35: 1207-1217 (1998).
Johnson, et al., "Primary plasma cell leukemia: morphologic, immunophenotypic , and cytogenetic features of 4 cases treated with chemotherapy and stem cell transplantation," Annals of Diagnostic Pathology, 10: 263-268 (2006).
Johnson & Johnson, Janssen to Demonstrate Breadth of Oncology Portfolio with 42 Clinical Data Presentation at the 2014 American Society of Hematology (ASH) Annual Meeting, San Francisco, California (Nov. 2014).
Jones, et al., "Depletion of CD25+ regulatory calls results in suppression of melanoma growth and induction of autoreactivity in mice," Cancer Immunity, 2: 1 (2002). Abstract.
Jones, et al., "Replacing the complementarity-determining regions in a human antibody with those from a mouse," Nature, 321: 522-525 (1986).
Kaufman, G.P. et al., "Daratumumab yields rapid and deep hematologic responses in patients with heavily pretreated AL amyloidosis," Blood, vol. 130; No. 7; 900-902 (2017).
Kita et al., "Antitumor effects of YM155, a novel suppressant, against human aggressive non-Hodgkin Lymphoma," Leukemia Research, vol. 35, pp. 787-792, (2011).
Kita, A., et al., "Sepantronium Bromide (YM155) Enhances Response of Human B-Cell Non-Hodgkin Lymphoma to Rituximab," The Journal of Pharmacology and Experimental Therapeutics, vol. 343; No. 1; 178-183 (2012).
Konapleva, et al., "Ligation of Cell Surface CD38 Protein with Agonistic Monoclonal Antibody Induced a Cell Growth Signal in Myeloid Leukemia Cells," The Journal of Immunology, 161: 4702-4708 (1998).
Kong, S.Y., et al., "Daratumumab Directly Induces Human Multiple Myeloma Cell Death and Acts Synergistically with Conventional and Novel Anti-Myeloma Drugs," Blood, vol. 116; Abstract 3013 (2010).
Konopleva, et al., "CD38 in Hematopoietic Malignancies," Chemical Immunol. Basel Karger, 75: 189-206 (2000).
Kreitman, et al., Phase I Trial of Recombinant Immunotoxin Anti-Tac (Fv)-PE38 (LMB-2) in Patients with Hematologic Malignancies, Journal of Clinical Oncology, 18: 1622-1636 (2000).
Krejcik, J. et al., "Daratumumab depletes CD38+ immune regulatory cells, promotes T-cell expansion, and skews T-cell repertoire in multiple myeloma," Blood, vol. 128; No. 3; 384-394 (2016).
Krejcik, J. et al., Immunomodulatory Effects and Adaptive Immune Response to Daratumumab in Multiple Myeloma,: Blood, vol. 126; 3037; 7 pages (2015).
Kreuger, et al., "Successful in vivo blockade of CD25 (high-affinity interleukin 2 receptor) on T cells by administration of humanized anti-Tac antibody to patients with psoriasis," Journal of American Academy of Dermatology, 41(3): 448-458 (2000).
Kropff, et al., "Bortezomib in combination with dexamethoasone for relapsed multiple myeloma," Leukemia Research, 29: 587-590 (2005).
Kumar, S. et al., "Expression of CD52 on plasma cells in plasma cell proliferative disorders," Blood, vol. 102; No. 3; 1075-1077 (2003).
Kupiec-Weglinski, "CD25-Targeted Therapy Revisited," Transplantation, 69(3): 328-330 (2000).
Lakshman, A. et al., "Efficacy of daratumumab-based therapies in patients with relapsed, refractory multiple myeloma treated outside of clinical trials," Am J. Hematol., vol. 92; 1146-1155 (2017).
Lande, et al., "CD38 ligation plays a direct role in the induction of IL-1β, I-6, and IL-10 secretion in resting human monocytes," Cellular Immunology, 220: 30-38 (2002).
Laubach, J.P., "Daratumumab granted breakthrough drug status," Expert Opinion Investig. Drugs, vol. 23; No. 4; 445-452 (2014).
Laurie, et al., "The role of CD4+CD25+ immunoregulatory T cells in the induction of autoimmune gastritis," Immunology and Cell Biology, 80: 567-573 (2002).
Lazar, et al., "Transforming Growth Factor α: Mutation of Aspartic Acid 47 and Leucine 48 Results in Different Biological Activities," Molecular and Cellular Biology, 8(3): 1247-1252 (1988).

(56) References Cited

OTHER PUBLICATIONS

Leonard, et al., "Molecular cloning and expression of cDNAs for the human interleukin-2 receptor," Nature 311(18): 626-631 (1984).
Lepenies, B. and Jacobs, T., "The Role of Negative Costimulators During Parasitic Infections," Endocrine, Metabolic & Immune Disorders—Drug Targets, vol. 8; 279-288 (2008).
Leveque "Subcutaneous Administration of Anticancer Agents" Anticancer Research, Departments of Pharmacy, University Hospital, Strasbourg, France, vol. 34, pp. 1579-1586 (2014).
Li, et al., "Creation of Patient Derived AML Xenografts Displaying Distinct Phenotypes and Geneotypes," Blood, vol. 122: No. 21, p. 5018 (2013).
Lin, et al., "Structure-Function Relationships in Glucagon: Properties of Highly Purified Des-His1-, Monoiodi-, and [Des-Asn28, Thr29](homoserine lactone27)-glucagon," Biochemistry, 14(9): 1559-1563 (1975).
Lippincott-Schwartz, "Antibodies as cell Biological Tools," Current Protocols in Cell Biology, 16.0.1-16.0.2, (2002).
Liu et al., "Induction of Chemoresistance by All-Trans Retinoic Acid via a Noncanonical Signaling in Multiple Myeloma Cells," PLOS ONE, vol. 9, No. 1, p. Article No. e85571, Jan. 2014.
Lonberg, et al., "Antigen-specific human antibodies from mice comprising four distinct genetic modifications," Nature: 308: 856-859 (1994).
Lu et al., "Issues Related to Targeted Delivery of Proteins & Peptides," The AAPS Journal, vol. 8, No. 3, Article 55, pp. E466-E478, Jul. 21, 2006.
MacCallum, et al., "Antibody-antigen Interactions: Contact Analysis and Binding Site Topography," Journal of Molecular Biology, 262, 732-745 (1998).
Machida, H. et al., "Aggressive plasma cell leukemia with cleaved, multilobated and monocytoid nuclei," International Journal of Hematol., vol. 73; Suppl 1; 158; Abstract No. 411 (2001).
Mai, E. et al., "Phase III trial of bortezomib, cyclophosphamide and dexamethasone (VCD) versus bortezomib, doxorubicin and dexamethasone (Pad) in newly diagnosed myeloma," Leukemia, vol. 29; 1721-1729 (2015).
Malavasi, et al., "Human CD38: a glycoprotein in search of a function," Immunology Today, 15(3): 95-97 (1994).
Maloney, et al., "Antibody Therapy for Treatment of Multiple Myeloma," Semin Hematol. 36 (Suppl. 3): 30-33 (1999).
Manier, S. et al., "Bone Marrow Microenvironment in Multiple Myeloma Progession," Journal of Biomedicine and Biotechnology, vol. 2012; 5 pages (2012).
Matas-Cespedes, A. et al., "The human CD38 monoclonal antibody daratumumab shows anti-tumor activity and hampers leukemia-microenvironment interactions in chronic lympocytic leukemia," Clinical Cancer Research, vol. 23; No. 6; 1493-1505 (2017).
Mauri, C. and Menon, M., "The expanding family of regulatory B cells," International Immunology, vol. 27; No. 10; 479-486 (2015).
McCarthy, P.L., "Strategies for induction, autologous hematopoietic stem cell transplantation, consolidation, and maintenance for transplantation-eligible multiple myeloma patients", Hematology, vol. 2013, NI. 1, pp. 496-503 (Dec. 2013).
McKelvey, et al., "Hydroxyldaunomycian (Adriamycin) Combination Chemotherapy in Malignant Lymphoma," Cancer, vol. 38, No. 4, pp. 1485-1493 (Oct. 1976).
Merlini, G. and Bellotti, V., "Molecular Mechanisms of Amyloidosis," The New England Journal of Medicine, vol. 349; No. 6; 583-596 (2003).
Mills, et al., Characterization of Monoclonal Antibodies that Inhibit CD38 Adp-ribosyl Cyclase Activity, LSSURP HLB Program, Department of Pharmacology, University of Minnesota, 2007.
Mills, E.N.C. et al., "The prevalence, cost and basis of food allergy across Europe," Allergy, vol. 62; 717-722 (2007).
Mikhael et al., "Cyclophosphamide-Bortezomib-Dexamethasone (CYBORD) Produces Rapid and Complete Hematological Response in Patients with AL Amyloidosis," Blood 119:4391-94 (Year: 2012).
Mohammad et al., "The Addition of Bryostatin 1 to Cyclophosphamide, Doxorubicin, Vincristine, and Prednisone (CHOP) Chemotherapy Improves Response in a CHOP-resistant Human Diffuse Large Cell Lymphoma Xenograft Model," Clinical Cancer Research, vol. 6, 4950-4956 (Dec. 2000).
Morrison, et al., "Chimeric human antibody molecules: Mouse antigen-binding domains with human constant region domains," Proceedings of the National Academy of Science USA, vol. 81; 6851-6855 (1984).
Mrowietz, "Treatment of Severe Psoriasis with Anti-CD25 Monoclonal Antibodies," Arch. Dermatology, 136: 675-676 (2000).
Mukherjee, et al., "Production and Characterization of Protective Human Antibodies against Shiga Toxin 1," Infection and Immunity, 70(10): 5896-5899 (2012).
Muyldermans, "Single domain camel antibodies: current status," Reviews in molecular Biotechnology, 74: 277-302 (2001).
Muyldermans, et al., "Recognition of antigens by single-domain antibody fragments: the superfluous luxury of paired domains," Trends in Biochemical Sciences, 26(4): 230-235 (2001).
Najjar et al., "Abstract P227: Accumulation of MDSC Subsets in Renal Cell Carcinoma Correlates with Grade and Progression Free Survival, and is Associated with Intratumoral Expression of IL-1β, IL-8 and CXCL5," Journal for Immunotherapy of Cancer, Nov. 6, 2014, vol. 2, p. 110-112.
Nijhof, I.S. et al., Preclinical Evidence for the Therapeutic Potential of CD38-Targeted Immuno-Chemotherapy in Multiple Myeloma Patients Refractory to Lenalidomide and Bortezomib. Clin Cancer Res., vol. 21, No. 12, pp. 2802-2810 (2014).
Nijhof, et al.,"Modulation of CD 38 Expression Levels on Multiple Myeloma Tumor Cells By All-Trans Retinoic Acid Improves the Efficacy of the Anti-CD 38 Monoclonal Antibody Daratumumab," Blood, American Society of Hematology, US, vol. 124, No. 21, p. 2096, Dec. 6, 2014. (Abstract Only).
Nijhof, I.S. et al., Combination of the anti-CD38 monoclonal antibody daratumumab and all-trans retinoic acid (Abstract in Proceedings of the AACR Special Conference on Hematologic Malignancies: Translating Discoveries to Novel Therapies). Clin Cancer Res, Sep. 20, 2014, vol. 21, No. 17 Suppl, pages Abstract A12; Abstract.
Nijhof I.S. et al.: "Upregulation of CD38 expression on multiple myeloma cells by all-trans retinoic acid improves the efficacy of daratumumab", Leukemia, vol. 29, No. 10, ISSN 1476-5551, pp. 2039-2049 (2015).
Nikaido, et al., "Molecular cloning of cDNA encoding human interleukin-2 receptor," Nature, 311: 631-635 (1984).
Offidani et al., "An evidence-based review of ixazomib citrate and its potential in the treatment of newly diagnosed multiple myeloma," OncoTargets and Therapy, vol. 7, pp. 1793-1800, 2014.
Onizuka, et al., "Tumor Rejection by in Vivo Administration of Anti-CD25 (Interleukin-2 Receptor α Monoclonal Antibody," Cancer Research, 59: 3128-3133 (1999).
Orlowski, "The Ubiquitin Proteasome pathway from Bench to Bedside," American Society of Hematology, 220-225 (2005).
Ostberg, et al., "Human and humanized monoclonal antibodies: preclinical studies and clinical experience," Biochemical Society Transactions, 23: 1-6 (1995).
Padlan, et al., "Identification of specificity-determining resides in antibodies," FASEB Journal, 9: 135-139 (1995).
Palumbo, A. et al., "Daratumumab, Bortezomib, and Dexamethasone for Multiple Myeloma," The New England Journal of Medicine, vol. 375; No. 8; 754-766 (2016).
Palumbo, A. et al., "Daratumumab, Bortezomib, and Dexamethasone for Multiple Myeloma," The New England Journal of Medicine, vol. 375; No. 8; 754-766; Suppl. Material: the protocol; total pp. 119 (2016).
Park, S. et al., "Successful Treatment by Rituximab of an Ebv-Related Lymphoma after Autologous Transplantation for Angioimmunoblastic T-Cell Lymphoma," International Journal of Hematol., vol. 76; Suppl. 1; 118; Abstract No. P340 (2002).
Parren et al., "HuMax-CD38, a new human CD38 monoclonal antibody, effectively mediates killing of multiple myeloma and plasma cell leukemia cells," American Society of Hematology 47th annual meeting, Atlanta, Georgia, USA, Dec. 10-13, 2005 (Abstract).
Parren, et al., HuMax-CD38, Myconos, Jun. 26, 2006.
Parren, et al., HuMax-CD38, Torino, Jun. 8-10, 2006.

(56) References Cited

OTHER PUBLICATIONS

Pascual, et al., "Anti-interleukin-2 receptor antibodies: basiliximab and daclizumab," Nephrology Dial. Transplant, 16: 1756-1760 (2001).
Patel, J.P., "Prognostic Relevance of Integrated Genetic Profiling in Acute Myeloid Leukemia," The New England Journal of Medicine, vol. 366; No. 12; 1079-1089 (2012).
Patton, D.T. et al., "The PI3K p110δ Regulates Expression of CD38 on Regulatory T Cells," PLOS one, vol. 6; No. 3; e17359; 8 pages (2011).
Paul, M.D., "Fundamental Immunology," Chapter 9, Raven Press, New York, $3^{rd}$ ed., 292-295 (1993).
Peipp, et al., "Fully Human CD38 Antibodies Efficiently Trigger ADCC and CDC of Multiple Myeloma Cell Lines and Primary Tumor Cells (Poster)," Blood, vol. 106(11): 944A, $47^{th}$ Annual Meeting of the American Society of Hematology, 2005; published (Nov. 16, 2005).
Peipp, et al., Fully Human CD38 Antibodies Efficiently Trigger ADCC and CDC of Multiple Myeloma and Plasma Cell Leukemia Cells (Poster 2) Conference proceedings, poster presentation at the 2005 Annual Meeting of the American Society of Hematology, (Dec. 12, 2005).
Peipp, et al., $47^{th}$ Annual Meeting of the American Society of Hematology, Atlanta, GA, December 10-13 2005. (Meeting Abstract).
Peng, et al., "Oncolytic measles viruses displaying a single-chain antibody against CD38, a myeloma cell marker," Blood, 101, 2557-2562 (2003).
Phase ½ Dose Escalation and Efficacy Study of Anti-CD38 Monoclonal Antibody in Patients With Selected CD38+ Hematological Malignancies, First posted Mar. 10, 2010, ClinicalTrials.gov. identifier No. NCT01084252.
Prosniak, M. et al.: "Development of a Cocktail of Recombinant-Expressed Human Rabies Virus-Neutralizing Monoclonal Antibodies for Postexposure Prophylaxis of Rabies," The Journal of Infectious Diseases, vol. 187; 53-56 (2003).
Rai, S. et al., "Successful Allogeneic Hematopoietic Stem Cell Transplantation in a Young Patient with Richter Syndrome Presenting with Chronic Lymphocytic Leukemia and Diffuse Large B-Cell Lymphoma with Different Cell Origins," Intern Med, vol. 52; 273-276 (2013).
Richardson, et al., "Daratumumab," Drugs of the Future, 38(8): 545-554 (2013).
Rituxan Hycela Label, "Highlights of prescribing information. Rituxan Hycela™ (rituximab and hyaluronidase human) injection, for subcutaneous use," 32 pages (Jun. 2017).
Sachchithanantham, S. et al., "Use of Plasma Cell Immunophenotype as Prognostic Markers in Patients with Systemic AL Amyloidosis," Blood, vol. 122; p. 3120 (2013).
Sagaster, V. et al., "Bortezomib in relapsed multiple myeloma: response rates and duration of response are independent of a chromosome 13q-deletion," Leukemia, vol. 21; 164-168 (2007).
Saito, M. et al., "A Case of Retroperitoneal Extramedullary Plasmacytoma," Acta Urol. Jpn., vol. 49; 735-739 (2003).
Salar et al., "Comparison of Subcutaneous Versus Intravenous Administration of Rituximab As Maintenance Treatment for Follicular Lymphoma: Results From a Two-Stage, Phase IB Study," Journal of Clinical Oncology, vol. 32, No. 17, pp. 1782-1791, (Jul. 10, 2014).
Sanchez-Gonzalez et al., "Rituximab subcutaneous in B-Cell non-Hodgkin lymphoma: clinical experience in a single center," Leukemia & Lymphoma, vol. 59, No. 4, pp. 1019-1021 (2018).
San-Miguel, J. et al., "Efficacy by cytogenetic risk status for daratumumab in combination with lenalidomide and dexamethasone or bortezomib and dexamethasone in relapsed or refractory multiple myeloma," EHA22; EHA Learning Center; Abstract; 4 pages (2017).
San-Miguel, J., "New approaches to myeloma treatment in 2017," EHA Learning Center; Abstract; 4 pages (2017).
Schonland, S., et al., "Detection and Charaterization of Plasma Cell and B Cell Clones in Patients with Systemic Light Chain Amyloidosis Using Flow Cytometry," Blood, vol. 142, p. 2068 (2014).

Sher, T. et al., "First report of safety and efficacy of daratumumab in 2 cases of advanced immunoglobulin light chain amyloidosis," Blood, vol. 128; No. 15; 1987-1989 (2016).
Shields, et al., "High Resolution mapping of the binding site on human IgG1 for FcγRi, FcγRII, FcγRIII, and FcRn and design of IgGI variants with improved binding to the FcγR," J. Biol. Chem., vol. 276, No. 9, pp. 6591-6604, (2001).
Shpilberg, et al., "Subcutaneous administration of rituximab (MabThera) and trastuzumab (Herceptin) using hyaluronidase," British Journal of Cancer, vol. 109, pp. 1556-1561, 2013.
Shubinsky, et al., "The CD38 Lymphocyte Differentiation Marker: New Insight into Its Ectoenzymatic Activity and Its Role as a Signal Transducer," Immunity, 7: 315-324 (1997).
Sicherer, S.H. and Sampson, H.A., "Food allergy: Epidemiology, pathogenesis, diagnosis, and treatment," J. Allergy Clin Inmmunol, vol. 133; 291-307 (2014).
Skeel, Handbook of Cancer Gliemotherapy, $3^{rd}$ edition, Little, Brown & Co., pp. 330-350 (1991).
Smithson, G. et al., "TAK-079 is a high affinity monoclonal antibody that effectively mediates CD38+ cell depletion," Journal of Immunol., vol. 198; Suppl. 1; 224.20; Abstract (2017).
Sonneveld, P. and Annemiek Broijl, "Treatment of Relapsed and Refractory Multiple Myeloma," Review Article, Leaders in Hematology, review series, Haematologica, 101(4):396-406 (2016).
Spencer, A. et al., "Daratumumab plus bortezomib and dexamethasone versus bortezomib and dexamethasone in relapsed or refractory multiple myeloma: updated analysis of CASTOR," Haematologica, vol. 103; No. 12; 2079-2087 (2018).
Strome, S.E. et al., "A Mechanistic Perspective of Monoclonal Antibodies in Cancer Therapy Beyond Target-Related Effects," The Oncologist, vol. 12; 1084-1095 (2007).
Swaika, A. et al., "Current state of anti-PD-L1 and anti-PD-1 agents in cancer therapy," Molecular Immunology, vol. 67; 4-17 (2015).
Tabernero, et al., "Adult precursor B-ALL with BCR/ABL gene rearrangements displays a unique 19mmunophenotyped based on the pattern of CD10, CD34, CD13, and CD38 expression," Leukemia, vol. 15, No. 3, pp. 406-414, (2001).
Talmadge, J.E. and Gabrilovich, D.I, "History of myeloid-derived suppressor cells," Nature Reviews, vol. 13; 739-752 (2013).
Terhorst, et al., "Biochemical Studies of the Human Thymocyte Cell-Surface Antigens T6, T9 and T10," Cell, 23: 771-780 (1981).
The Cancer Genome Atlas Research Network et al., "Genomic and Epigenomic Landscapes of Adult De Novo Acute Myeloid Leukemia," N. Engl. J. Med, vol. 368; No. 22; 2059-2074 (2013).
Topalian, S.L., et al., "Immune Checkpoint Blockade: A Common Denominator Approach to Cancer Therapy," Cancer Cell, vol. 27; 450-461 (2015).
Tzartos, S.J., et al., "Epitope Mapping by Antibody Competition," Methods in Molecular Biology, vol. 66; 55-66 (1996).
Usmani, et al., "Clinical efficacy of daratumumab monotherapy in patients with heavily pretreated relapsed or refractory multiple myeloma," Blood, vol. 128, No. 1, pp. 37-44, (May 23, 2016).
Usmani, S.Z. et al., "Efficacy of Daratumumab, Lenalidomide, and Dexamethasone Versus Lenalidomide and Dexamethasone in Relapsed or Refractory Multiple Myeloma Patients with 1 to 3 Prior Lines of Therapy: Updated Analysis of Pollux," Blood, vol. 128; No. 22; 1151; 10 pages (2016).
Usmani, S.Z. et al., "Open-Label, Multicenter, Dose Escalation Phase 1b Study to Assess the Subcutaneous Delivery of Daratumumab in Patients (pts) with Relapsed or Refractory Multiple Myeloma," Blood, vol. 128; No. 22; 1149 (2016).
Usmani, S.Z. et al., "Subcutaneous delivery of daratumumab in relapsed or refractory multiple myeloma," Blood, vol. 134; No. 8; 668-677 (2019).
Vadjos, et al., "Comprehensive Functional Maps of the Antigen-binding Site of an Anti-ErbB2 Antibody Obtained with Shotgun Scanning Mutagenesis," Journal of Molecular Biology, 320: 415-428 (2002).
Van Bueren, et al., "Direct In Vitro Comparison of Daratumumab With Surrogate Analogs of Anti-CD38 Antibodies," New Evidence Oncology Issue, Apr. 2015 [retrieved on Feb. 3, 2016] Retrieved

(56) References Cited

OTHER PUBLICATIONS from the Internet: URL: Http:///www.newevidence.com/oncology/direct-in-vitro-comparison-of-daratumumab-with-surrogate-analogs-of-anti-cd38-antibodies>.

Van de Donk et al., "Monoclonal antibodies targeting CD38 in hematological malignancies and beyond," Immunological Reviews, vol. 270, pp. 95-112, (2016).

Venner et al., "Cyclophosphamide, bortezomib, and dexamethasone therapy in AL amyloidosis is associated with high clonal response rates and prolonged progression-free survival," Blood, vol. 119, No. 9, pp. 4387-4390, (2012).

Vorre, et al., "Multiple Daratumumab Abstracts to be Presented at EHA," ArrayDiagnostica, Abstract Only (2014).

Wagner, V., et al., "Preclinical Efficacy of Sepantronium Bromide (YM155) in multiple myeloma is conferred by down regulation of Mcl-1," Oncotarget, 5(21): 10237-10250 (2014).

Wagner et al., Survivin in Multiple Myeloma: Prognostic and Therapeutic Implications, vol. 118, Article 137, 2011 (Abstract Only).

Wang, L. et al., "VISTA, a novel mouse Ig superfamily ligand that negatively regulates T cell responses," J. Exp. Med., vol. 208; No. 3; 577-592 (2011).

WCJ van de Donk, "A Phase 1 and Phase 2 Study of Daratumumab in Combination With All-Trans Retinoic Acid in Relapsed/Refractory Multiple Myeloma," Clinical Trials.gov Identification No. NCT02751255; (First posted Apr. 26, 2016).

Wei, W. et al., "Roles and mechanisms of the CD38/cyclic adenosine diphosphate ribose/Ca2+ signaling pathway," World Journal of Biological Chemistry, vol. 5; No. 1; 58-67 (2014).

Weisel, K.C. et al., "Efficacy of daratumumab in combination with lenalidomide plus dexamethasone (DRd) or bortezomib plus dexamethasone (RVd) in relapsed or refractory multiple myeloma (RRMM) based on cytogenetic risk status," Journal of Clinical Oncology, vol. 35; No. 15; 8006; Abstract (2017).

Ye et al., "Abstract P240: Treg Increases HepG2 Cell Growth by RANK-RANKL pathway." Journal for Immunotherapy of Cancer, vol. 2; Suppl 3; P240 (Nov. 6, 2014).

International Preliminary Report on Patentability issued May 8, 2018 for International Application No. PCT/US2016/59893, entitled "Subcutaneous Formulations of Anti-CD38 Antibodies and Their Uses".

International Search Report and Written Opinion mailed Jan. 24, 2017 for International Application No. PCT/US2016/59893, entitled "Subcutaneous Formulations of Anti-CD38 Antibodies and Their Uses".

International Preliminary Report on Patentability issued Dec. 26, 2017 for International Application No. PCT/US2016/038702, entitled "Combination Therapies for Heme Malignancies With Anti-CD38 Antibodies and Survivin Inhibitors".

International Search Report and Written Opinion mailed Nov. 29, 2016 for International Application No. PCT/US2016/038702, entitled "Combination Therapies for Heme Malignancies With Anti-CD38 Antibodies and Survivin Inhibitors".

International Preliminary Report on Patentability issued Mar. 14, 2017 for International Application No. PCT/US2015/048899, entitled "Combination Therapies With Anti-CD38 Antibodies".

International Search Report and Written Opinion mailed Apr. 8, 2016 for International Application No. PCT/US2015/048899, entitled "Combination Therapies With Anti-CD38 Antibodies".

International Preliminary Report on Patentability issued Nov. 21, 2017 for International Application No. PCT/US2016/033544, entitled "Anti-CD38 Antibodies for Treatment of Light Chain Amyloidosis and Other CD38-Positive Hematological Malignancies".

International Search Report and Written Opinion mailed Oct. 24, 2016 for International Application No. PCT/US2016/033544, entitled "Anti-CD38 Antibodies for Treatment of Light Chain Amyloidosis and Other CD38-Positive Hematological Malignancies".

International Preliminary Report on Patentability issued Jun. 6, 2016 for International Application No. PCT/US2015/063371, entitled "Anti-CD38 Antibodies for Treatment of Acute Myeloid Leukemia".

International Search Report and Written Opinion mailed Feb. 19, 2016 for International Application No. PCT/US2015/063371, entitled "Anti-CD38 Antibodies for Treatment of Acute Myeloid Leukemia".

International Preliminary Report on Patentability issued Dec. 26, 2017 for International Application No. PCT/US2016/039165, entitled "Immune Modulation and Treatment of Solid Tumors With Antibodies That Specifically Bind CD38".

International Search Report and Written Opinion mailed Oct. 14, 2016 for International Application No. PCT/US2016/039165, entitled "Immune Modulation and Treatment of Solid Tumors With Antibodies That Specifically Bind CD38".

International Preliminary Report on Patentability issued Sep. 6, 2016 for International Application No. PCT/US2015/017425, entitled "Anti-CD38 Antibodies for Treatment of Acute Lymphoblastic Leukemia".

International Search Report and Written Opinion mailed Sep. 21, 2015 for International Application No. PCT/US2015/017425, entitled "Anti-CD38 Antibodies for Treatment of Acute Lymphoblastic Leukemia".

International Preliminary Report on Patentability issued Jan. 10, 2019 for International Application No. PCT/EP2017/066063, entitled "Treatment Of IgE-Mediated Diseases With Antibodies That Specifically Bind CD38".

International Search Report and Written Opinion mailed Sep. 25, 2017 for International Application No. PCT/EP2017/066063, entitled "Treatment Of IgE-Mediated Diseases With Antibodies That Specifically Bind CD38".

International Preliminary Report on Patentability mailed May 14, 2020 for International Application No. PCT/US2018/058561, entitled "Methods of Treating High Risk Multiple Myeloma".

International Search Report and Written Opinion mailed Feb. 12, 2019 for International Application No. PCT/US2018/058561, entitled "Methods of Treating High Risk Multiple Myeloma".

International Search Report and Written Opinion mailed Apr. 24, 2020 for International Application No. PCT/US2019/056838, entitled "Method of Providing Subcutaneous Administration of Anti-CD38 Antibodies".

International Preliminary Report on Patentability issued Sep. 6, 2016 for International Application No. PCT/US2015/017420, entitled "Combination Therapies With Anti-CD38 Antibodies".

International Search Report and Written Opinion mailed Jul. 8, 2015 for International Application No. PCT/US2015/017420, entitled "Combination Therapies With Anti-CD38 Antibodies".

Intellectual Property Office of Singapore Written Opinion dated Apr. 17, 2018 for Application No. 11201701867S, entitled "Combination Therapies with Anti-CD38 Antibodies".

Supplementary European Search Report dated Feb. 21, 2018 for European Application No. EP 15839752, entitled "Combination Therapies with Anti-CD38 Antibodies".

Non Final Office Action for U.S. Appl. No. 15/340,290 date mailed Nov. 20, 2017.

Final Office Action for U.S. Appl. No. 15/340,290 date mailed May 16, 2018.

Non Final Office Action for U.S. Appl. No. 15/340,290 date mailed Oct. 10, 2018.

Non Final Office Action for U.S. Appl. No. 15/366,474 date mailed Nov. 20, 2017.

Final Office Action for U.S. Appl. No. 15/366,474 date mailed May 16, 2018.

Applicant Initiated Interview for U.S. Appl. No. 15/366,474 date mailed Sep. 17, 2018.

Non Final Office Action for U.S. Appl. No. 15/366,474 date mailed Oct. 11, 2018.

Non Final Office Action for U.S. Appl. No. 15/189,577 date mailed Oct. 31, 2017.

Final Office Action for U.S. Appl. No. 15/189,577 date mailed Apr. 13, 2018.

(56) References Cited

OTHER PUBLICATIONS

Non Final Office Action for U.S. Appl. No. 15/189,577 date mailed Sep. 28, 2018.
Non Final Office Action for U.S. Appl. No. 14/847,428 date mailed Sep. 23, 2016.
Non Final Office Action for U.S. Appl. No. 15/386,391 date mailed Jun. 18, 2018.
Non Final Office Action for U.S. Appl. No. 15/160,476 date mailed Sep. 15, 2017.
Non Final Office Action for U.S. Appl. No. 15/160,476 date mailed Nov. 5, 2018.
Final Office Action for U.S. Appl. No. 15/160,476 date mailed Apr. 23, 2018.
Non Final Office Action for U.S. Appl. No. 14/956,890 date mailed Nov. 25, 2016.
Final Office Action for U.S. Appl. No. 14/956,890 date mailed Jul. 24, 2018.
Non Final Office Action for U.S. Appl. No. 15/340,214 date mailed May 16, 2018.
Non Final Office Action for U.S. Appl. No. 14/629,965 date mailed Dec. 21, 2015.
Final Office Action for U.S. Appl. No. 14/629,965 date mailed Apr. 29, 2016.
Notice of Allowance for U.S. Appl. No. 14/629,965 date mailed Apr. 13, 2017.
Non Final Office Action for U.S. Appl. No. 15/445,225 date mailed Jun. 29, 2018.
Final Office Action for U.S. Appl. No. 15/445,225 date mailed Dec. 17, 2018.
Non Final Office Action for U.S. Appl. No. 15/651,333 date mailed Sep. 27, 2018.
Final Office Action for U.S. Appl. No. 15/386,391 date mailed Dec. 28, 2018.
Final Office Action for U.S. Appl. No. 14/956,890 date mailed Jan. 14, 2019.
Notice of Allowance for U.S. Appl. No. 15/651,333 date mailed Feb. 21, 2019.
Notice of Allowance for U.S. Appl. No. 15/189,577 date mailed Mar. 5, 2019.
Final Office Action for U.S. Appl. No. 15/340,290 date mailed Mar. 11, 2019.
Notice of Allowance for U.S. Appl. No. 15/386,391 date mailed Mar. 29, 2019.
Notice of Allowance for U.S. Appl. No. 15/340,290 date mailed May 22, 2019.
Notice of Allowance for U.S. Appl. No. 15/651,333 date mailed May 31, 2019.
Final Office Action for U.S. Appl. No. 15/160,476 date mailed Jun. 14, 2019.
Notice of Allowance for U.S. Appl. No. 15/445,225 date mailed Jul. 29, 2019.
Notice of Allowance for U.S. Appl. No. 15/386,391 date mailed Jul. 30, 2019.
Non-Final Office Action for U.S. Appl. No. 14/956,890 date mailed Jul. 30, 2019.
Notice of Allowance for U.S. Appl. No. 15/189,577 date mailed Sep. 12, 2019.
Notice of Allowance for U.S. Appl. No. 15/651,333 date mailed Oct. 9, 2019.
Notice of Allowance for U.S. Appl. No. 15/386,391 date mailed Nov. 18, 2019.
Notice of Allowance for U.S. Appl. No. 15/445,225 date mailed Dec. 4, 2019.
Notice of Allowance for U.S. Appl. No. 15/189,577 date mailed Dec. 19, 2019.
Non Final Office Action for U.S. Appl. No. 15/160,476 date mailed Dec. 20, 2019.
Final Office Action for U.S. Appl. No. 14/956,890 date mailed Jan. 7, 2020.
Non-Final Office Action for U.S. Appl. No. 15/798,670 mailed Jan. 22, 2020.
English translation of Office Action for JP Application No. 2016-554350, mailed Nov. 27, 2018.
Notice of Allowance for U.S. Appl. No. 15/445,225 date mailed Mar. 25, 2020.
Notice of Allowance for U.S. Appl. No. 15/189,577 date mailed Mar. 31, 2020.
Notice of Allowance for U.S. Appl. No. 15/160,476 date mailed May 4, 2020.
Notice of Allowance for U.S. Appl. No. 16/380,994 date mailed May 12, 2020.
Notice of Allowance for U.S. Appl. No. 16/460,754 date mailed May 18, 2020.
Notice of Allowance for U.S. Appl. No. 15/445,225 date mailed Jul. 15, 2020.
Notice of Allowance for U.S. Appl. No. 14/956,890 date mailed Jul. 29, 2020.
Non-Final Office Action for U.S. Appl. No. 15/798,670 mailed Aug. 7, 2020.
Notice of Allowance for U.S. Appl. No. 16/380,994 date mailed Aug. 12, 2020.
Non-Final Office Action for U.S. Appl. No. 16/162,355 mailed Aug. 13, 2020.
Non-Final Office Action for U.S. Appl. No. 16/177,239 mailed Aug. 24, 2020.
Notice of Allowance for U.S. Appl. No. 16/460,754 date mailed Sep. 10, 2020.
Final Office Action for U.S. Appl. No. 15/798,670 mailed Dec. 16, 2020.
ASH Clinical News, "Is Daratumumab Plus Lenalidomide-Dexamethasone a New Standard for Transplant-Ineligible Myeloma," Dated Jan. 1, 2019, Retrieved from Internet URL: https://www.ashclinicalnews.org/on-location/ash-annual-meeting/daratumumab-plus-lenalidomid; Retrieved Oct. 28, 2022 (2 pages).
AstraZeneca 206162 Clinical Pharmacology Review 2014, (https://www.accessdata.fda.gov/drugsatfda_docs/nda/2014/206162Orig1s000ClinPharmR.pdf; Application No. 206162Orig1s000; 117 pages.
Avet-Loiseau, H. et al., "Evaluation of Minimal Residual Disease (MRD) in Relapsed/Refractory Multiple Myeloma (RRMM) Patients Treated with Daratumumab in Combination with Lenalidomide Plus Dexamethasone or Bortezomib Plus Dexamethasone," Blood, vol. 128; No. 22; 246; 7 pages (2016).
Bauer, Fromming, Fuhrer, "Lehrbuch der Pharmazeutischen Technologie"8th Edition, Wissenschaftliche Verlagsgesellschaft Stuttgart, Chapter 9; 238-243 (2006). (concise explanation met by submission of the enclosed Opponent's submission filed by Dr. Markus Breuer cited as Other Document 148).
Bittner, B. et al., "Development of a Subcutaneous Formulation for Trastuzumab—Nonclinical and Clinical Bridging Approach to the Approved Intravenous Dosing Regimen," Arzneimittelforschung, vol. 62; 401-409 (2012).
Bittner, B. et al., "Non-Clinical Pharmacokinetic /Pharmacodynamic and Early Clinical Studies Supporting Development of a Novel Subcutaneous Formulation for the Monoclonal Antibody Rituximab," Drug Res., vol. 64; 569-575 (2014).
Bittner, B. et al., "Subcutaneous Administration of Biotherapeutics: An Overview of Current Challenges and Opportunities," BioDrugs, vol. 32; 425-440 (2018).
Bookbinder, L.H. et al., "A recombinant human enzyme for enhanced interstitial transport of therapeutics," Journal of Controlled Release, vol. 114; 230-241 (2006).
CAS Registry Results, dated Oct. 9, 2020, Registry No. 757971-58-7, "36-482-Hyaluronoglucosaminidase PH20 (human)," 6 pages.
Chari, A., et al., "Subcutaneous Daratumumab (DARA) in Patients (Pts) With Relapsed or Refractory Multiple Myeloma (RRMM): Part 2 Update of the Open-label, Multicenter, Dose-escalation Phase 1b Study (PAVO)", Poster Presented at the Annual Meeting of the American Society of Clinical Oncology (ASCO); Jun. 5, 2018; Chicago, Illinois.
Chaulagain, C.P. et al., "Pre-clinical translational studies of daratumumab in patients with myeloma or AL amyloidosis undergoing autologous

(56) References Cited

OTHER PUBLICATIONS hematopoietic stem cell transplantation (SCT)," Journal of Clinical Oncology, May 20, 2015, vol. 33, No. 15 suppl., pp. 8587-8587.
CHMP Assessment Report for Herceptin (trastuzumab), 70 pages (2013).
CHMP Assessment Report for Mabthera (rituximab), 103 pages (2014).
Chung, C.H., "Managing Premedications and the Risk for Reactions to Infusional Monoclonal Antibody Therapy," The Oncologist, vol. 13; 725-732 (2008).
ClinicalTrials.gov, "Daratumumab (HuMax-CD38) Safety Study in Multiple Myeloma," Identifier: NCT00574288; Latest version posted: Apr. 27, 2018 (10 pages).
ClinicalTrials.gov, "An Investigational Immuno-Therapy Study to Determine the Safety and Effectiveness of Nivolumab and Daratumumab in Patients with Multiple Myeloma," Identifier: NCT01592370; Latest version posted: Jun. 18, 2021 (10 pages).
ClinicalTrials.gov, "History of Changes for Study: NCT02252172: Study Comparing Daratumumab, Lenalidomide, and Dexamethasone With Lenalidomide and Dexamethasone in Participants With Previously Untreated Multiple Myeloma," U.S. National Library of Medicine, ClinicalTrials.gov Archive, Oct. 17, 2017 (24 pages).
ClinicalTrials.gov, "History of Changes for Study: NCT02519452: A Study of Daratumumab With the Addition of Recombinant Human Hyaluronidase (rHuPH20) for the Treatment of Participants with Relapsed or Refractory Multiple Myeloma," U.S. National Library of Medicine, ClinicalTrials.gov Archive, Dec. 3, 2020 (12 pages).
ClinicalTrials.gov, "A Study of Daratumumab with the Addition of Recombinant Human Hyaluronidase (rHuPH20) for the Treatment of Participants with Relapsed or Refractory Multiple Myeloma," Identifier: NCT02519452; (5 pages).
Colson, K., "Treatment-related symptom management in patients with multiple myeloma: a review," Support Care Cancer, vol. 23; 1431-1445 (2015).
Common Terminology Criteria for Adverse Events (CTCAE), Version 4.03, U.S. Department of Health and Human Services, 4 pages (2010).
Complete Specification for Indian Application No. 4718/CHENP/2007; published on Jan. 11, 2008 (225 Pages).
Consolidated list of references from Opposition in parent patent EP No. 3370770, 4 pages; Feb. 24, 2022.
CureSearch for Children's Cancer, "Relapse of Recurrence," Retrieved from Internet URL: https://curesearch.org/Relapse-or-Recurrence, 3 pages; Retrieved on Oct. 27, 2022.
Darzalex, Highlights and Prescribing Information, FDA Label, 24 pages (2015).
Darzalex, Highlights and Prescribing Information, FDA Label, 32 pages (2018).
Davies, A. et al., "Pharmacokinetics and safety of subcutaneous rituximab in follicular lymphoma (SABRINA): stage 1 analysis of a randomised phase 3 study," The Lancet, vol. 15; 343-352 (2014).
Demarest, T.G. et al., "NAD+ Metabolism in Aging and Cancer," Annual Rev. Cancer Biol., vol. 3; 105-130 (2019).
Dimopoulos, M.A. et al., "Daratumumab, Lenalidomide, and Dexamethasone for Multiple Myeloma," The New England Journal of Medicine, vol. 375; No. 14; 1319-1331 (2016); Suppl. Material: the protocol; total pages 111 (2016).
Dimopoulos, M.A. et al., "Daratumumab plus pomalidomide and dexamethasone versus pomalidomide and dexamethasone alone in previously treated multiple myeloma (APOLLO): an open-label, randomised, phase 3 trial," Lancet Oncol, vol. 22; 801-812 (2021).
Doessegger, L. and Banholzer, M.L., "Clinical development methodology for infusion-related reactions with monoclonal antibodies," Clinical & Translational Immunology, vol. 4; e39; 9 pages (2015).
Drach, J. et al., "Retinoic Acid-induced Expression of CD38 Antigen in Myeloid Cells is Mediated through Retinoic Acid Receptor-$\alpha^1$," Cancer Research, vol. 54; 1746-1752 (1994).
Durie, B.G.M. et al., "International Uniform Response Criteria for Multiple Myeloma," Leukemia, vol. 20; 1467-1473 (2006).

European Medicines Agency, Summary of Product Characteristics for Rituximab; 153 pages; Oct. 30, 2009, https://www.ema.europa.eu/en/documents/product-information/mabthera-epar-product-information_en.pdf.
European Union Clinical Trials Register Clinical Trials Register, EudraCT No. 2014-002272-88; Title: "A Phase 3, Randomized, Controlled, Open-label Study of VELCADE (Bortezomlb) Melphalan-Prednisone (VMP) Compared to Daratumumab In Combination with VMP (D-VMP), In Subjects with Previously Untreated Multiple Myeloma who are Inellgible for High-dose Therapy," 6 pages (2015).
European Union Clinical Trials Register Clinical Trials Register, EudraCT No. 2014-002273-11; Title: "A Phase 3 Study Comparing Daratumumab, Lenalidomide, and Dexamethasone (DRd) vs Lenalidomide and Dexamethasone (Rd) In Subjects with Previously Untreated Multiple Myeloma who are Ineligible for High Dose Therapy," 7 pages (2015).
European Union Clinical Trials Register Clinical Trials Register, EudraCT No. 2013-005525-23; Title: "Phase 3 Study Comparing Daratumumab, Lenalidomide, and Dexamethasone (DRd) vs Lenalidomide and Dexamethasone (Rd) in Subjects with Relapsed or Refractory Multiple Mycloma," 7 pages (2014).
European Union Clinical Trials Register Clinical Trials Register, EudraCT No. 2014-000255-85; Title: "Phase 3 Study Comparing Daratumumab, Bortezomlb and Dexamethasone (DVd) vs Bortezomib and Dexamethasone (Vd) In Subjects With Relapsed or Refractory Multiple Myeloma," 6 pages (2014).
Facon, T. et al., "Phase 3 Randomized Study of Daratumumab Plus Lenalidomide and Dexamethasone (D-Rd) Versus Lenalidomide and Dexamethasone (Rd) in Patients with Newly Diagnosed Multiple Myeloma (NDMM) Ineligible for Transplant (MAIA)," Blood, vol. 132 (Suppl 1); 8 Pages (2018).
Faiman, B. et al., "Steroid-Associated Side Effects in Patents with Multiple Myeloma: Consensus Statement of the IMF Nurse Leadership Board," Clinical Journal of Oncology Nursing, vol. 12; No. 3; 53-63 (2008).
Frost, G.I., "Recombinant human hyaluronidase (rHuPH20): an enabling platform for subcutaneous drug and fluid administration," Expert Opinion Drug Deliv., vol. 4; No. 4; 427-440 (2007).
Gariani, K. et al., "Inhibiting poly ADP-ribosylation increases fatty acid oxidation and protects against fatty liver disease," Journal of Hepatology, vol. 66; 132-141 (2017).
Gay, F. and Palumbo, A., "Management of Older Patients with Multiple Myeloma," Blood Reviews, vol. 25; 65-73 (2011).
Goel, M. et al., "Plasticity within the Antigen-Combining Site May Manifest as Molecular Mimicry in the Humoral Immune Response," The Journal of Immunology, vol. 173; 7358-7367 (2004).
Haller, M.F., "Converting Intravenous Dosing to Subcutaneous Dosing," Pharmaceutical Technology, 118-132 (2007).
Halozyme, "Halozyme Therapeutics Reports Selection of First Product Candidate Under Janssen Collaboration," Press Release, 4 pages (2015).
Hamizi, S. et al., "Subcutancous trastuzumab: dcvclopmcnt of a new formulation for treatment of HER2-positive early breast cancer," OncoTargets and Therapy, vol. 6; 89-94 (2013).
Herceptin, Highlights and Prescribing Information, FDA Label, 33 pages (1998).
Highlights of Prescribing Information, Rituxan, 53 pages (1997).
Highlights of Prescribing Information, Rituxan (rituximab) injection, 44 pages (1997).
Hydase, Highlights and Prescribing Information, FDA Label, 6 pages (2005).
Hylenex, Highlights and Prescribing Information, FDA Label, 9 pages (2005).
Hyun, J. et al., "Capture and Release of Proteins on the Nanoscale by Stimuli-Responsive Elastin-Like Polypeptide "Switches"", J. Am. Chem. Soc., vol. 126; 7330-7335 (2004).
Jaccard, A. et al., "Efficacy of bortezomib, cyclophosphamide and dexamethasone in treatment-naïve patients with high-risk cardiac AL amyloidosis (Mayo Clinic stage III)," Hacmatologica, vol. 99; No. 9; 1479-1485 (2014).

(56) References Cited

OTHER PUBLICATIONS

Jackisch, C. et al., "Subcutaneous Administration of Monoclonal Antibodies in Oncology," Geburtsh Fraucnhclk, vol. 74; 343-349 (2014).

Janssen Initiates Rolling Submission of Biologic License Application (BLA) for daratumumab with U.S. FDA for the Treatment of Multiple Myeloma, News Release, 3 pages (2015).

Janssen to Demonstrate Breadth of Oncology Portfolio with 41 Clinical Data Presentations at the 2014 American Society of Hematology (ASH) Annual Meeting [online], Nov. 6, 2014, Internet :<URL: https://www.jnj.com/media-center/press-releases/janssen-to-demonstrate-breadth-of-oncology-portfolio-with-41-clinical-data-presentations-at-the-2014-american-socicty-of-hematology-ash-annual-meeting>; 8 pages.

Janssen Submits Marketing Authorisation Application for Daratumumab for European Patients with Heavily Pre-treated Multiple Myeloma, Jansscn-Cilag International NV; 7 pagcs (2015).

Jolles, S., "Hyaluronidase facilitated subcutaneous immunoglobulin in primary immunodeficiency," Immuno Targets and Therapy, vol. 2; 125-133 (2013).

Khagi, Y. and Mark, T., "Potential role of daratumumab in the treatment of multiple myeloma," Onco Targets and Therapy, 1095-1100 (2014).

Khan, T. and Salunke, D.M., "Adjustable Locks and Flexible Keys: Plasticity of Epitope-Paratope Interactions in Germline Antibodies," The Journal of Immunology, vol. 192; 5398-5405 (2014).

Kim, H. et al., "Overview of methods for comparing the efficacies of drugs in the absence of head-to-head clinical trial data," Br. J. Clin. Pharmacol., vol. 77; No. 1; 116-121 (2013).

Knowles, S.P. et al., "Safety of recombinant human hyaluronidase PH20 for subcutaneous drug delivery," Expert Opinion on Drug Delivery, vol. 18; No. 11; 1673-1685 (2021).

Kussic, P.H. ct al., "A Single Engineered Amino Acid Substitution Changes Antibody Finc Specificity," Journal of Immunology, vol. 152; 146-152 (1994).

Kyle, R.A. and Rajkumar, S.V., "Criteria for diagnosis, staging, risk stratification and response assessment of multiple myeloma," Leukemia, vol. 23; 3-9 (2009).

Kyle, R.A. et al., "Clinical Course and Prognosis of Smoldering (Asymptomatic) Multiple Myeloma," The New England Journal of Medicine, vol. 356; 2582-2590 (2007).

Kyle, R.A. et al., "Review of 1027 Patients with Newly Diagnosed Multiple Myeloma," May Clinic Proc., vol. 78; 21-33 (2003).

Laubach, J.P. et al., "The challenge of cross-trial comparisons using limited data," haematologica, vol. 99; e145; 2 pages (2014).

Laurini, J.A. et al., "Classification of non-Hodgkin lymphoma in Central and South America: a review of 1028 cases," Blood, vol. 120; vol. 24; 4795-4801 (2012).

Lefranc, M. et al., "IMGT unique numbering for immunoglobulin and T cell receptor variable domains and Ig superfamily V-like domains," Developmental & Comparative Immunology, vol. 27; 55-77 (2003).

Lokhorst, H.M. et al., "Targeting CD38 with Daratumumab Monotherapy in Multiple Myeloma," The New England Journal of Medicine, vol. 373; 1207-1219 (2015).

Lokhorst, H.M. et al., "Targeting CD38 with Daratumumab Monotherapy in Multiple Myeloma," The New England Journal of Medicine, vol. 373; 1207-1219 (2015); Supplemental Appendix.

Lonial, S. et al., "Phase II study of daratumumab (DARA) monotherapy in patients with greater than or equal to 3 lines of prior therapy or double refractory multiple myeloma (MM): 54767414MMY2002 (Sirius)," Journal of Clinical Oncology, vol. 33; No. 18_Suppl (2015).

Lonial, S. et al., "Monoclonal antibodies in the treatment of multiple myeloma: current status and future perspectives," Leukemia, vol. 30; 526-535 (2016).

Mahajan, S. et al., "The evolution of stem-cell transplantation in multiple myeloma," Therapeutic Advances in Hematology, vol. 9; No. 5; 123-133 (2018).

Mariuzza, R.A. eet al., "The Structural Basis of Antigen-Antibody Recognition, Ann. Rev. Biophys. Biophys. Chem.," vol. 16; 139-159 (1987).

Mateos, M. et al., "Daratumumab plus Bortezomib, Melphalan, and Prednisone for Untreated Myeloma," N England J Med, vol. 378; 518-528 (2018).

Maury, M. et al., "Spray-drying of proteins: effects of sorbitol and trehalose on aggregation and FT-IR amide I spectrum of an immunoglobulin G," European Journal of Pharmaccutics and Biopharmaceutics, vol. 59; 251-261 (2005).

McCudden, C. et al., "Monitoring multiple myeloma patients treated with daratumumab: teasing out monoclonal antibody interference," Clin Chem Lab Med, vol. 54; No. 6; 1095-1104 (2016).

Moreau, P. et al., "Rituximab in CD20 positive multiple myeloma," Leukemia, vol. 21; 835-836 (2007).

Moreau, P. et al., "Practical Considerations for the Use of Daratumumab, a Novel CD38 Monoclonal Antibody, in Myeloma," Drugs, vol. 76; 853-867 (2016).

Nahi, H. et al., "An open-label, dose escalation phase 1b study of subcutaneous daratumumab with recombinant human hyaluronidase in patients with relapsed or refractory multiple myeloma (PAVO)," Journal of Clinical Oncology, vol. 34; No. 15; 4 pages (2016).

Negrin, R., Patient education: Hematopoietic transplantation (bone marrow transplantation) (Beyond the Basics), Retrieved from Internet URL: https://www.uptodate.com/contents/hematopoietic-cell-transplantation-bone-marrow-transplantation-beyond-the-basics, 15 pages; Retrieved on Oct. 27, 2022.

Ocio, E.M. et al., "New drugs and novel mechanisms of action in multiple myeloma in 2013: a report from the International Myeloma Working Group (IMWG)," Leukemia, vol. 28; 525-542 (2014).

Ohaegbulam K C et al.: "Human cancer immunotherapy with antibodies to the PD-1 and PD-L1 pathway", Trends in Molecular Medicine, Jan. 2015; 21 (1): 24-33.

Ortolani, C., "CD38: Antigen: Flow Cytometry of Hematological Malignancies," Blackwell Publishing, 1st Edition, 68-70 (2011).

Palumbo, A. et al., "International Myeloma Working Group guidelines for the management of multiple myeloma patients ineligible for standard high-dose chemotherapy with autologous stem cell transplantation," Leukemia, vol. 23; 1716-1730 (2009).

Palumbo, A. and Anderson, K., "Multiple Myeloma," The New England Journal of Medicine, vol. 364; 1046-1060 (2011).

Panka, D.J. et al., "Variable region framework differences result in decreased or increased affinity of variant anti-digoxin antibodies," Proc. Natl. Acad. Sci., vol. 85, 3080-3084 (1988).

Patent Assignment Cover Sheet for U.S. Appl. No. 16/380,994, 6 pages; filed Sep. 11, 2019.

Phase 3 COLUMBIA study Investigating a Subcutaneous Formulation of DARZALEX (daratumumab) Showed Non-Inferiority to Intravenous Administration in Patients with Relapsed/Refractory Multiple Myeloma, Chicago, 7 pages (2019).

Phipps, C., et al., "Daratumumab and its potential in the treatment of multiple myeloma: overview of the preclinical and clinical development," Ther. Adv. Hematol., vol. 6; No. 3; 120-127 (2015).

Pivot, X. et al., "Patients' preferences for subcutaneous trastuzumab versus conventional intravenous infusion for the adjuvant treatment of HER2-positive carly breast cancer: final analysis of 488 patients in the international, randomized, two-cohort PrefHer study," Annals of Oncology, vol. 25; 1979-1987 (2014).

Poosarla, V.G. ct al., "Computational Dc Novo Design of Antibodies Binding to a Peptide With High Affinity," Biotechnology & Bioengineering, vol. 114; No. 6; 1331-1342 (2017).

Pre-Grant Notice of Opposition filed in Indian Application No. 201617029109, by Indian Pharmaceutical Alliance, dated Feb. 24, 2022 (30 pages).

Preliminary Opinion of the Opposition Division, as cited in EP Opposition against EP Patent No. 3370770; 13 pages; dated Aug. 8, 2022.

Pui, C. and Jeha, S., "New therapeutic strategies for the treatment of acute lymphoblastic leukemia," Nature Reviews, vol. 6; 149-165 (2007).

Rader, C. et al., "A phage display approach for rapid antibody humanization: Designed combinatorial V gene libraries," Proc. Natl. Acad. Sci, vol. 95; 8910-8915 (1998).

(56) References Cited

OTHER PUBLICATIONS

Raj, T.A. et al., "Vincristine sulfate liposomal injection for acute lymphoblastic leukemia," International Journal of Nanomedicine, vol. 8; 4361-4369 (2013).
Rajkumar, S.V. et al., "Consensus recommendations for the uniform reporting of clinical trials: Report of the International Myeloma Workshop Consensus Panel 1," Blood, vol. 117; No. 18; 4691-4695 (2011).
Rituxan (tituximab), Highlights of prescribing information. Rituxan (IV administered Rituximab; 35 pages (1997).
Rosengren, S. et al., Clinical Immunogenicity of rHuPH20, a Hyaluronidase Enabling Subcutaneous Drug Administration, The AAPS Journal, vol. 17; No. 5; 1144-1156 (2015).
Ruberg, E-M. and Frieβ, W., "Sensibel und stressanfallig," Pharmazeutische Zeitung, 156 JG, AUSG. 50; 15 pages (2011). (concise explanation met by submission of the enclosed Opponent's submission filed by Dr. Markus Breuer cited as Other Document 140).
Rudikoff, S. et al., "Single amino acid substitution altering antigen-binding specificity," Proc. Natl. Acad., col. 79; 1979-1983 (1982).
Ryan, et al., "Potentiation of Anti-Myeloma Activity of Daratumumab with Combination of Cyclophosphamide, Lenalidomide or Bortezomib via a Tumor Secretory Response That Greatly Augments Macrophage-Induced ADCP," Annual Meeting at the Haematology Association of Ireland, Oct. 15, 2016; 20 pages.
San-Miguel, J., et al., "Subcutaneous Daratumumab in Patients with Relapsed or Refractory Multiple Myeloma: Part 2 Update of the Open-label, Multicenter, Dose Escalation Phase 1b Study (PAVO)", Poster Presented at the 23rd European Hematology Association (EHA) Annual Congress; Jun. 14-17, 2018; Stockholm, Sweden.
Solal-Deligny, P., "Rituximab by subcutaneous route," Expert Rev. Hematol., vol. 8; No. 2; 147-153 (2015).
Sondergeld, P. et al., "Monclonal Antibodies in Myeloma," Clinical Advances in Hematology & Oncology, vol. 13; Issue 9; 599-609 (2015).
Strickley, R.G. and Lambert, W.J., "A review of formulations of commercially available antibodies," Journal of Pharmaceutical Sciences, vol. 110; 2590-2608 (2021).
Taussig, D.C. et al., "Anti-CD38 antibody-mediated clearance of human repopulating cells masks the heterogeneity of leukemia-initiating cells," Blood, vol. 112; No. 3; 568-575 (2008).
Thomas, D.A. et al., "Chemoimmunotherapy with Hyper-CVAD plus Rituximab for the Treatment of Adult Burkitt and Burkitt-Type Lymphoma or Acute Lymphoblastic Leukemia," The American Cancer Society, vol. 106; No. 7; 1569-1580 (2006).
Usmani, S.Z. et al., "Final analysis of the phase III non-inferiority COLUMBA study of subcutaneous versus intravenous daratumumab in patients with relapsed or refractory multiple myeloma," Haematologica, vol. 107; 2408-2417 (2022).
Wang, W. et al., "Antibody Structure, Instability, and Formulation," Journal of Pharmaceutical Sciences, vol. 96; 1-26 (2007).
Warne, N.W., "Development of high concentration protein biopharmaceuticals: The use of platform approaches in formulation development," European Journal of Pharmaceutics and Biopharmaceutics, vol. 78; 208-212 (2011).
Wasserman, R.L., "Progress in Gammaglobulin Therapy for Immunodeficiency: From Subcutaneous to Intravenous Infusions and Back Again," J. Clin. Immunol., vol. 32 ; 1153-1164 (2012).
Wasserman, R.L., "Overview of recombinant human hyaluronidase-facilitated subcutaneous infusion of IgG in primary immunodeficiencies," Immunotherapy, vol. 6; No. 5; 553-567 (2014).
WHO Drug Information, International Nonproprietary Names for Pharmaceutical Substances (INN), Proposed INN: List 101, vol. 23; No. 2; 64 pages (2009).
WHO Drug Information, International Nonproprietary Names for Pharmaceutical Substances (INN), Recommended INN: List 63, 40 pages (2010).
Wu, et al., An Analysis of the Sequences of the Variable Regions of Bence Jones Proteins and Myeloma Light Chains and Their Implications for Antibody Complementarity, Journal of Experimental Medicine, 132: 211-250 (1970).
Wunderlich, M. et al., "AML cells are differentially sensitive to chemotherapy treatment in a human xenograft model," eBlood, vol. 121; No. 12; e90-e97 (2013).
Yamamoto, H. et al., "A mammalian homolog of the zebrafish transmembrane protein 2 (TMEM2) is the long-sought-after cell-surface hyaluronidase," J. Biol. Chem., vol. 292; No. 18; 7304-7313 (2017).
Zadnikova, P. et al., "The Degradation of Hyaluronan in the skin," Biomolecules, vol. 12; 251, 17 pages (2022).
Zagouri, F. et al., "Emerging antibodies for the treatment of multiple myeloma," Expert Opinion on Emerging Drugs, vol. 21; No. 2; 225-237 (2016).
Zojer, N. et al., "Rituximab treatment provides no clinical benefit in patients with pretreated advanced multiple myeloma," Leukemia & Lymphoma, vol. 47; No. 6; 1103-1109 (2006).
International Preliminary Report on Patentability mailed Apr. 29, 2021 for International Application No. PCT/US2019/056838, entitled "Method of Providing Subcutaneous Administration of Anti-CD38 Antibodies".
International Preliminary Report on Patentability for International Application No. PCT/IB2020/051484, mailed Sep. 2, 2021.
International Search Report and Written Opinion for International Application No. PCT/IB2020/051484, mailed Jul. 2, 2020.
Decision Revoking the European Patent issued in EP Patent No. 3370770, mailed Apr. 20, 2023; 22 Pages.
Declaration of Professor Paul Anthony Dalby, in Opposition Proceedings against European Patent No. 3370770, 20 pages (Dated May 2022).
Declaration of Professor Christian Jackisch, in Opposition Proceedings against European Patent No. 3370770, 8 pages (Dated May 10, 2022).
Declaration of Professor Adrian Llewellyn Harris, in Opposition Proceedings against European Patent No. 3370770, 109 pages (Dated Dec. 20, 2022).
Declaration of Dr. Richard Senderoff, in Opposition Proceedings against European Patent No. 3370770, 28 pages (Dated Dec. 20, 2022).
Declaration of Professor Dr. Andreas Zimmer, in Opposition Proceedings against European Patent No. 3370770, 5 pages (Dated Jan. 9, 2023).
Second Declaration of Professor Christian Jackisch, in Opposition Proceedings against European Patent No. 3370770, 8 pages (Dated Jan. 6, 2023).
Notice of Opposition Dated Oct. 20, 2021 by Opponent König Szynka Tilmann von Renesse, filed in European Patent No. 3 370 770 B1.
Notice of Opposition Dated Oct. 19, 2021 by Opponent Patent Boutique LLP, filed in European Patent No. 3 370 770 B1.
Notice of Opposition Dated Oct. 20, 2021 by Opponent Dr. Markus Breuer, filed in European Patent No. 3 370 770 B1.
Notice of Opposition Dated Dec. 22, 2022 by Opponent Dr. Hans Ulrich Dorries, filed in European Patent No. 3 827 845 B1; 44 Pages.
Notice of Opposition Dated Dec. 27, 2022 by Opponent Konig Szynka Tilmann von Renesse, filed in European Patent No. 3 827 845 B1; 49 Pages.
Notice of Opposition Dated Dec. 28, 2022 by Opponent Michalski Huttermann & Partner, filed in European Patent No. 3 827 845 B1; 44 Pages.
Notice of Opposition Dated Dec. 29, 2022 by Opponent Patent Boutique LLP, filed in European Patent No. 3 827 845 B1; 49 Pages.
Notice of Opposition Dated Dec. 21, 2022 by Opponent Xbrane Biopharma AB, filed in European Patent No. 3 827 845 B1; 68 Pages.
Opponent's submission by Dr. Markus Breuer dated Oct. 4, 2022 filed in European Patent No. 3 370 770 B1.
Opponent's submission by Konig Szynka Tilmann von Renesse dated Jan. 11, 2023, filed in European Patent No. 3 370 770 B1; 27 Pages.

(56) References Cited

OTHER PUBLICATIONS

Opponent's submission by Dr. Markus Breuer dated Jan. 13, 2023, filed in European Patent No. 3 370 770 B1; 11 Pages.
Opponent's submission by Patent Boutique LLP dated Jan. 12, 2023, filed in European Patent No. 3 370 770 B1; 56 Pages.
Provision of the Minutes in Accordance with Rule 124(4) EPC regarding EP Patent No. 3370770, mailed Apr. 20, 2023, 14 pages.
Reply to Notice of Opposition, filed in European Patent No. 3 370 770 B1, entitled: "Subcutaneous Formulations Of Anti-CD38 Antibodies And Their Uses," 416 pages, dated May 12, 2022.
Reply to Notice of Opposition, filed in European Patent No. 3 370 770 B1, entitled: "Subcutaneous Formulations Of Anti-CD38 Antibodies And Their Uses," 19 pages, dated Jan. 13, 2023.
Non Final Office Action for U.S. Appl. No. 16/840,153 date mailed Aug. 16, 2022.
Applicant Initiated Interview Summary for U.S. Appl. No. 16/840,153 date mailed Jun. 8, 2022.
Non Final Office Action for U.S. Appl. No. 16/840,153 date mailed Mar. 22, 2022.
Applicant Initiated Interview Summary for U.S. Appl. No. 16/840,153 date mailed Apr. 6, 2022.
Notice of Allowance for U.S. Appl. No. 16/840,153 date mailed Dec. 21, 2022.
Non Final Office Action for U.S. Appl. No. 16/927,947 date mailed Mar. 7, 2023.
Applicant Initiated Interview Summary for U.S. Appl. No. 16/927,947 date mailed Apr. 19, 2023.
Non Final Office Action for U.S. Appl. No. 17/116,822 date mailed Mar. 8, 2023.
Applicant Initiated Interview Summary for U.S. Appl. No. 17/116,822 date mailed Apr. 19, 2023.
Notice of Allowance for U.S. Appl. No. 17/116,822 date mailed May 12, 2023.
Non Final Office Action for U.S. Appl. No. 17/116,835 date mailed Mar. 8, 2023.
Applicant Initiated Interview Summary for U.S. Appl. No. 17/116,835 date mailed Apr. 19, 2023.
Notice of Allowance for U.S. Appl. No. 17/116,835 date mailed May 11, 2023.
Non-Final Office Action for U.S. Appl. No. 17/005,039 date mailed Dec. 9, 2022.
Final Office Action for U.S. Appl. No. 17/005,039 date mailed Apr. 28, 2023.
Notice of Allowance for U.S. Appl. No. 16/162,355 mailed Apr. 9, 2021.
Non Final Office Action for U.S. Appl. No. 16/741,542 date mailed Jul. 12, 2022.
Notice of Allowance for U.S. Appl. No. 16/741,542 date mailed Nov. 2, 2022.
Non Final Office Action for U.S. Appl. No. 16/741,542 date mailed Mar. 17, 2023.
Notice of Allowance for U.S. Appl. No. 16/741,542 date mailed Apr. 10, 2023.
Non-Final Office Action for U.S. Appl. No. 16/312,133 mailed Oct. 28, 2021.
Notice of Allowance for U.S. Appl. No. 16/312,133 mailed Sep. 2, 2022.
Final Office Action for U.S. Appl. No. 16/312,133 mailed May 12, 2022.
Non-Final Office Action for U.S. Appl. No. 16/312,133 mailed Dec. 8, 2022.
Final Office Action for U.S. Appl. No. 15/798,670 mailed Aug. 10, 2021.
Non-Final Office Action for U.S. Appl. No. 15/798,670 mailed Apr. 2, 2021.
Non-Final Office Action for U.S. Appl. No. 15/798,670 mailed Feb. 4, 2022.
Non-Final Office Action for U.S. Appl. No. 16/177,239 mailed Sep. 21, 2021.
Final Office Action for U.S. Appl. No. 16/177,239 mailed Feb. 10, 2021.
Notice of Allowance for U.S. Appl. No. 16/177,239, mailed Oct. 13, 2022.
Final Office Action for U.S. Appl. No. 16/177,239 date mailed Mar. 4, 2022.
Notice of Allowance for U.S. Appl. No. 16/177,239 date mailed Feb. 3, 2023.
Notice of Allowability for U.S. Appl. No. 16/177,239, mailed Feb. 27, 2023.
Non-Final Office Action for U.S. Appl. No. 16/656,569 mailed Aug. 26, 2021.
Non Final Office Action for U.S. Appl. No. 17/015,017 date mailed Dec. 23, 2022.
Final Office Action for U.S. Appl. No. 17/015,017 date mailed Apr. 3, 2023.
Non Final Office Action for U.S. Appl. No. 17/674,397 date mailed Apr. 24, 2023.
Non Final Office Action for U.S. Appl. No. 16/797,301 date mailed Jul. 28, 2022.
Final Office Action for U.S. Appl. No. 16/797,301 date mailed Feb. 17, 2023.
Non Final Office Action for U.S. Appl. No. 17/475,975 date mailed Mar. 10, 2023.
Non Final Office Action for U.S. Appl. No. 16/830,585 date mailed Mar. 17, 2022.
Final Office Action for U.S. Appl. No. 16/830,585 date mailed Oct. 26, 2022.
Non Final Office Action for U.S. Appl. No. 16/830,763 date mailed Mar. 17, 2022.
Final Office Action for U.S. Appl. No. 16/830,763 date mailed Oct. 24, 2022..
Non Final Office Action for U.S. Appl. No. 16/830,810 date mailed Mar. 15, 2022.
Final Office Action for U.S. Appl. No. 16/830,810 date mailed Oct. 25, 2022.
Non Final Office Action for U.S. Appl. No. 16/830,909 date mailed Mar. 17, 2022.
Final Office Action for U.S. Appl. No. 16/830,909 date mailed Oct. 26, 2022.
BC Cancer Agency Cancer drug Manual, Oct. 1, 2013, "Hydroxyurea". http://www.bccancer.bc.ca/drug-database-site/Drug%20Index/Hydroxyurea_monograph_1Oct2013.pdf; Retrieved on Nov. 20, 2023; 7 pages (No Author given).
Child, J.A. et al, "High-Dose Chemotherapy with Hematopoietic Stem-Cell Rescue for Multiple Myeloma," N Engl J Med, vol. 348; 1875-1883 (2003).
City of Hope, "What's the Difference? Biosimilar and generic drug," City of Hope, retrieved from: https://www .cancercenter.com/community/blog/2018/12/whats-the-difference-biosimilar-and-generic-drugs; 3 Pages (Year: 2018).
ClinicalTrials.gov, "A Study to Evaluate Daratumumab in Transplant Eligible Participants with Previously Untreated Multiple Myeloma (Cassiopeia)," Identifier: NCT02541383; First Posted: Sep. 4, 2015 (29 pages).
ClinicalTrials.gov, "Safety and Efficacy Study of Eculizumab in Patients with Refractory Generalized Myasthenia Gravis," Identifier: NCT00727194; Latest version: Sep. 13, 2019 (6 pages).
Darzalex, Highlights and Prescribing Information, FDA Label, 11 pages (2017).
Davies, A. et al., "Pharmacokinetics and safety of subcutaneous rituximab in follicular lymphoma (SABRINA): stage 1 analysis of a randomised phase 3 study," The Lancet, vol. 15; 343-352 (2014); Supplemental Appendix (8 Pages).
Davis, T.A. et al., "Rituximab Anti-CD20 Monoclonal Antibody Therapy in Non-Hodgkin's Lymphoma: Safety and Efficacy of Re-Treatment," Journal of Clinical Oncology, vol. 18; No. 17; 3135-3143 (2000).
Freeley et al., "The 'Ins and Outs' of complement-driven immune responses", Immunol Rev., 274(1), pp. 16-32, Nov. 2016.

(56) References Cited

OTHER PUBLICATIONS

Karakasheva et al., "CD38-Expressing Myeloid-Derived Suppressor Cells Promote Tumor Growth in a Murine Model of Esophageal Cancer", Microenvironment and Immunol., 75(19), pp. 4074-4085, Oct. 1, 2015.
Kaufman, J.L. et al., "Bortezomib, Thalidomide, and Dexamethasone as Induction Therapy for Patients with Symptomatic Multiple Myeloma," Cancer, vol. 116; 3143-3151 (2010).
King, T. et al., "Best Practice for the Administration of Daratumumab in Multiple Myeloma: Australian Myeloma Nurse Expert Opinion," Asia Pac J Oncol Nurs, vol. 5; 270-284 (2018).
Kwan et al., "Complement regulation of T cell immunity", Immunol Res, 54(0), pp. 247-253, Dec. 2012.
Leukemia—Acute Myeloid—AML—Treatment Options. Cancer. Net, Nov. 19, 2013. archived by the Wayback Machine at https://web.archive.org/web/20131120003806/http://www.cancer.net/print/19072; Retrieved on Nov. 20, 2023; 6 pages (No Author Listed).
Matsuda, M. et al., "Phenotypic analysis of plasma cells in bone marrow using flow cytometry in AL amyloidosis," Amyloid, 10(2), 110-116 (2003).
McLaughlin, P. et al., "Pituximab Chimeric Anti-CD20 Monoclonal Antibody Therapy for Relapsed Indolent Lymphoma: Half of Patients Respond to a Four-Dose Treatment Program," Journal of Clinical Oncology, vol. 16; No. 8; 2825-2833 (1998).
Moreau, P. et al., "Multiple Myeloma: ESMO Clinical Practice Guidelines for diagnosis, treatment and follow up," Annals of Oncology, vol. 28; Suppl 4; iv52-iv61 (2017).
Multiple Myeloma Treatment Regiments (MMTR), Multiple Myeloma Treatment Regiments (Part 1 of 9), Haymarket Media, Inc., 9 Pages (2017).
Myeloma Australia, "Steroids," Treatment Fact Sheet, Myeloma Australia, retrieved from: https://myeloma.org.au/wp-content/uploads/2018/09/Steroid-FS-Sep18.pdf 2 Pages (2018).
Piro, L.D. et al., "Extended Rituximab )anti-CD20 monoclonal antibody) therapy for relapsed or refractory low-grade or follicular non-Hodgkins lymphoma," Annals of Oncology, vol. 10; 655-661 (1999).
Rituxan (tituximab), Highlights of prescribing information. Rituxan (IV administered Rituximab; 44 pages (1997); Revised 2014.
Van Beurden-Tan et al., "Systemic Literature Review and Network Meta-Analysis of Treatment Outcomes in Relapsed and/or Refractory Multiple Myeloma," Journal of Clinical Oncology, vol. 35; No. 12; 1312-1319 (2017).
Whatcott et al., "Targeting the tumor microenvironment in cancer: why hyaluronidase deserves a second look", Cancer Discov., 1(4), pp. 291-296, Sep. 2011.
Declaration of Professor Paul Anthony Dalby, in Opposition Proceedings against European Patent No. 3827845, 20 pages (Dated Jul. 19, 2023).
Declaration of Peter Hellemans, in Opposition Proceedings against European Patent No. 3827845, 5 pages (Dated Jul. 21, 2023).
Declaration of Tara Masterson, in Opposition Proceedings against European Patent No. 3827845, 4 pages (Dated Jul. 2023).
Declaration of Professor Christian Jackisch, in Opposition Proceedings against European Patent No. 3827845, 11 pages (Dated Jul. 19, 2023).
Reply of the Patentee to the Notices of Opposition in European Patent No. 3 827 845 B1, Jul. 23, 2023 (203 pages).
Notice of Allowance for U.S. Appl. No. 16/927,947 date mailed Jun. 22, 2023.
Non-Final Office Action for U.S. Appl. No. 17/005,039 date mailed Sep. 1, 2023.
Non Final Office Action for U.S. Appl. No. 17/015,017 date mailed Aug. 18, 2023.
Non Final Office Action for U.S. Appl. No. 17/002,860 date mailed Jun. 27, 2023.
Non Final Office Action for U.S. Appl. No. 17/691,050 date mailed Oct. 3, 2023.
Final Office Action for U.S. Appl. No. 17/674,397 date mailed Oct. 18, 2023.
Non Final Office Action for U.S. Appl. No. 16/797,301 date mailed Sep. 22, 2023.
Caraccioio, D. et al., "Exploiting MYC-induced PARPness to target genomic instability in multiple myeloma," Haematologica, vol. 106; No. 1; 185-195 (2021).
CAS Registry Results, Registry No. 945721-28-8, "Daratumumab," 3 pages (2024).
Cavo, M. et al., "Bortezomib-thalidomide-dexamethasone is superior to thalidomide-dexamethasone as consolidation therapy after autologous hematopoietic stem cell transplantation in patients with newly diagnosed multiple myeloma," Blood, vol. 120; No. 1; 9-19 (2012).
CHMP Assessment Report for HyQvia, 68 pages (2013).
ClinicalTrials.gov, "Daratumumab, Thalidomide and Dexamethasone in Relapse and/or Refractory Myeloma," Identifier: NCT03143036; Last Update: Jun. 7, 2018 (15 pages).
Consolidated list of references from Opposition in patent EP No. 3827845, 6 pages; Jul. 24, 2023.
Consolidated list of references from Opposition in patent EP No. 3370770, 4 pages; 2023.
Dakhil, S. et al., "Phase III safety study of rituximab administered as a 90-minute infusion in patients with previously untreated diffuse large B-cell and follicular lymphoma," Leukemia & Lymphoma, vol. 55; No. 10; 2335-2340 (2014).
Genmab, "Genmab Announces Positive Topline Results in Phase III CASSIOPEIA Study of Daratumumab in Front Line Multiple Myeloma," Genmab News, 4 Pages (2018).
Highlights of Prescribing Information, Darzalex, 27 pages (2015); Revised Nov. 2016.
Kumar, S.K. et al., "Treating Multiple Myeloma Patients with Oral Therapies," Clinical Lymphoma, Myeloma & Leukemia, vol. 17; No. 5; 243-251 (2017).
Lokhorst, H.M., "Dose-Dependent efficacy of daratumumab (DARA) as monotherapy in patients with relapsed or refractory multiple myeloma (RR MM)," Journal of Clinical Oncology, vol. 32; No. 15; 4 pages (2014).
Lonial, S. et al., "Phase II study of daratumumab (DARA) monotherapy in patients with greater than or equal to 3 lines of prior therapy or double refractory multiple myeloma (MM): 54767414MMY2002 (Sirius)," Identifier: NCT01985126; Presented at ASC Annual Meeting (2015).
Morcos, P.N. et al., "Pharmacokinetics and pharmacodynamics of single subcutaneous doses of tocilizumab administered with or without rHuPH20," International Journal of Clinical Pharmacology and Therapeutics, vol. 15, No. Jul. 2013; 537-548 (2013).
Moreau, P. et al., "An Open-Label, Multicenter, Phase 1b Study of Daratumumab in Combination with Backbone Regimens in Patients with Multiple Myeloma," Blood, vol. 124; No. 21; 176 (2014).
Palumbo, A. et al., "Melphalan 200 mg/m2 versus melphalan 100 mg/m2 in newly diagnosed myeloma patients: a prospective, multicenter phase 3 study," Blood, vol. 115; No. 10; 1873-1879 (2010).
Quartino, A.L. et al., "Population pharmacokinetic and exposure-response analysis for trastuzumab administered using a subcutaneous "manual syringe" injection or intravenously in women with HER2-positive early breast cancer," Cancer Chemother Pharmacol, vol. 77; 77-88 (2016).
Rajkumar, S.V. et al., "Multiple Myeloma: 2018 update on Diagnosis, Risk-stratification and Management," Am J. Hematol, vol. 93; No. 8; 981-1114 (2019).
Rituxan (tituximab), Highlights of prescribing information. Rituxan (IV administered Rituximab; 53 pages (1997); Revised 2021.
Wasserman, R.L. et al., "Recombinant human hyaluronidase-facilitated subcutaneous infusion of human immunoglobulins for primary immunodeficiency," J Allergy Clin Immunol, vol. 130; 951-957 (2012).
Wynne, C. et al., "Comparison of Subcutaneous and Intravenous Administration of Trastuzumab: A Phase I/Ib Trial in Healthy Male Volunteers and Patients with HER2-Positive Breast Cancer," The Journal of Clinical Pharmcology, vol. 53; No. 2; 192-201 (2012).
Annex to Form 2300—Notice of Opposition, filed on behalf of Konig Szynka Tilmann von Renesse, filed in Opposition for EP Patent 3370770, 39 pages (2024).

(56) References Cited

OTHER PUBLICATIONS

Second Declaration of Professor Adrian Llewellyn Harris, in Opposition Proceedings against European Patent No. 3370770, 5 pages (Dated Jan. 3, 2024).
Declaration of Peter Hellemans, in Opposition Proceedings against European Patent No. 3370770, 5 pages (Dated Aug. 24, 2023).
Declaration of Tara Masterson, in Opposition Proceedings against European Patent No. 3370770, 4 pages (Dated Aug. 2023).
Opponent's submission by Dr. Markus Breuer dated Jan. 15, 2024, filed in European Patent No. 3 370 770 B1; 53 Pages.
Opponents Submission by Dr. Markus Breuer to Comments on Proprietor's Submission , filed in EP Opposition for EP Patent 3370770, 17 pages; dated Oct. 4, 2022.
Representation for Indian Pharmaceutical Alliance in Opposition of Patent for IN Application No. 201617029321, dated May 5, 2022 (29 pages).
Reply of the Patentee, Janssen Biotech, Inc., to the Notices of Opposition in European Patent No. 3370770, Aug. 2023 (63 pages).
Response to Patentee's Statement of Grounds of Appeal, filed by Patent Boutique LLP in European Patent No. 3370770 , dated Jan. 12, 2024 (74 pages).
Response to Patentee's Statement of Grounds of Appeal, filed on behalf of Konig Szynka Tilmann von Renesse in European Patent No. 3370770 , dated Jan. 15, 2024 (106 pages).
Response to Summons to Attend Oral Proceedings in Opposition against EP 3770770, filed on behalf of Dr. Markus Breuer, 11 pages; filed on Jan. 13, 2023.
Final Office Action for U.S. Appl. No. 17/005,039 date mailed Dec. 22, 2023.
Non-Final Office Action for U.S. Appl. No. 17/329,057 mailed Dec. 12, 2023.
Notice of Allowance for U.S. Appl. No. 17/015,017 date mailed Nov. 29, 2023.
Final Office Action for U.S. Appl. No. 17/002,860 date mailed Nov. 30, 2023.
Final Office Action for U.S. Appl. No. 17/691,050 date mailed Mar. 8, 2024.
Non Final Office Action for U.S. Appl. No. 17/005,825 date mailed Feb. 28, 2024.
Non Final Office Action for U.S. Appl. No. 17/674,397 date mailed Mar. 1, 2024.
Final Office Action for U.S. Appl. No. 16/797,301 date mailed Jan. 29, 2024.

* cited by examiner

*$P \ll 0.01$ for *CD38* compared to all others, paired t test (mean+/-SD), (N=16).

SEQUENCE LISTING

```
<160> NUMBER OF SEQ ID NOS: 22

<210> SEQ ID NO 1
<211> LENGTH: 300
<212> TYPE: PRT
<213> ORGANISM: Homo sapiens

<400> SEQUENCE: 1

Met Ala Asn Cys Glu Phe Ser Pro Val Ser Gly Asp Lys Pro Cys Cys
1               5                   10                  15

Arg Leu Ser Arg Arg Ala Gln Leu Cys Leu Gly Val Ser Ile Leu Val
            20                  25                  30

Leu Ile Leu Val Val Val Leu Ala Val Val Val Pro Arg Trp Arg Gln
        35                  40                  45

Gln Trp Ser Gly Pro Gly Thr Thr Lys Arg Phe Pro Glu Thr Val Leu
    50                  55                  60

Ala Arg Cys Val Lys Tyr Thr Glu Ile His Pro Glu Met Arg His Val
65                  70                  75                  80

Asp Cys Gln Ser Val Trp Asp Ala Phe Lys Gly Ala Phe Ile Ser Lys
                85                  90                  95

His Pro Cys Asn Ile Thr Glu Glu Asp Tyr Gln Pro Leu Met Lys Leu
            100                 105                 110

Gly Thr Gln Thr Val Pro Cys Asn Lys Ile Leu Leu Trp Ser Arg Ile
        115                 120                 125

Lys Asp Leu Ala His Gln Phe Thr Gln Val Gln Arg Asp Met Phe Thr
    130                 135                 140

Leu Glu Asp Thr Leu Leu Gly Tyr Leu Ala Asp Asp Leu Thr Trp Cys
145                 150                 155                 160
```

```
Gly Glu Phe Asn Thr Ser Lys Ile Asn Tyr Gln Ser Cys Pro Asp Trp
                165                 170                 175

Arg Lys Asp Cys Ser Asn Asn Pro Val Ser Val Phe Trp Lys Thr Val
            180                 185                 190

Ser Arg Arg Phe Ala Glu Ala Ala Cys Asp Val Val His Val Met Leu
        195                 200                 205

Asn Gly Ser Arg Ser Lys Ile Phe Asp Lys Asn Ser Thr Phe Gly Ser
    210                 215                 220

Val Glu Val His Asn Leu Gln Pro Glu Lys Val Gln Thr Leu Glu Ala
225                 230                 235                 240

Trp Val Ile His Gly Gly Arg Glu Asp Ser Arg Asp Leu Cys Gln Asp
                245                 250                 255

Pro Thr Ile Lys Glu Leu Glu Ser Ile Ile Ser Lys Arg Asn Ile Gln
            260                 265                 270

Phe Ser Cys Lys Asn Ile Tyr Arg Pro Asp Lys Phe Leu Gln Cys Val
        275                 280                 285

Lys Asn Pro Glu Asp Ser Ser Cys Thr Ser Glu Ile
    290                 295                 300

<210> SEQ ID NO 2
<211> LENGTH: 14
<212> TYPE: PRT
<213> ORGANISM: Homo sapiens

<400> SEQUENCE: 2

Ser Lys Arg Asn Ile Gln Phe Ser Cys Lys Asn Ile Tyr Arg
1               5                   10

<210> SEQ ID NO 3
<211> LENGTH: 14
<212> TYPE: PRT
<213> ORGANISM: Homo sapiens

<400> SEQUENCE: 3

Glu Lys Val Gln Thr Leu Glu Ala Trp Val Ile His Gly Gly
1               5                   10

<210> SEQ ID NO 4
<211> LENGTH: 122
<212> TYPE: PRT
<213> ORGANISM: Artificial Sequence
<220> FEATURE:
<223> OTHER INFORMATION: antibody VH

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Asn Ser Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Thr Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Asp Lys Ile Leu Trp Phe Gly Glu Pro Val Phe Asp Tyr Trp
```

```
                 100             105             110
Gly Gln Gly Thr Leu Val Thr Val Ser Ser
        115             120

<210> SEQ ID NO 5
<211> LENGTH: 107
<212> TYPE: PRT
<213> ORGANISM: Artificial Sequence
<220> FEATURE:
<223> OTHER INFORMATION: antibody VL

<400> SEQUENCE: 5

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys
            100                 105

<210> SEQ ID NO 6
<211> LENGTH: 5
<212> TYPE: PRT
<213> ORGANISM: Artificial Sequence
<220> FEATURE:
<223> OTHER INFORMATION: Antibody HCDR1

<400> SEQUENCE: 6

Ser Phe Ala Met Ser
1               5

<210> SEQ ID NO 7
<211> LENGTH: 17
<212> TYPE: PRT
<213> ORGANISM: Artificial Sequence
<220> FEATURE:
<223> OTHER INFORMATION: Antibody HCDR2

<400> SEQUENCE: 7

Ala Ile Ser Gly Ser Gly Gly Thr Tyr Tyr Ala Asp Ser Val Lys
1               5                   10                  15

Gly

<210> SEQ ID NO 8
<211> LENGTH: 13
<212> TYPE: PRT
<213> ORGANISM: Artificial Sequence
<220> FEATURE:
<223> OTHER INFORMATION: mAb HCDR3

<400> SEQUENCE: 8

Asp Lys Ile Leu Trp Phe Gly Glu Pro Val Phe Asp Tyr
1               5                   10

<210> SEQ ID NO 9
```

```
<211> LENGTH: 11
<212> TYPE: PRT
<213> ORGANISM: Artificial Sequence
<220> FEATURE:
<223> OTHER INFORMATION: Antibody LCDR1

<400> SEQUENCE: 9

Arg Ala Ser Gln Ser Val Ser Ser Tyr Leu Ala
1               5                   10

<210> SEQ ID NO 10
<211> LENGTH: 7
<212> TYPE: PRT
<213> ORGANISM: Artificial Sequence
<220> FEATURE:
<223> OTHER INFORMATION: Antibody LCDR2

<400> SEQUENCE: 10

Asp Ala Ser Asn Arg Ala Thr
1               5

<210> SEQ ID NO 11
<211> LENGTH: 10
<212> TYPE: PRT
<213> ORGANISM: Artificial Sequence
<220> FEATURE:
<223> OTHER INFORMATION: Antibody LCDR3

<400> SEQUENCE: 11

Gln Gln Arg Ser Asn Trp Pro Pro Thr Phe
1               5                   10

<210> SEQ ID NO 12
<211> LENGTH: 452
<212> TYPE: PRT
<213> ORGANISM: Artificial Sequence
<220> FEATURE:
<223> OTHER INFORMATION: Antibody HC

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Asn Ser Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Asp Lys Ile Leu Trp Phe Gly Glu Pro Val Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175
```

Ala Val Leu Gln Ser Ser Gly Leu Tyr Ser Leu Ser Ser Val Val Thr
            180                 185                 190

Val Pro Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 13
<211> LENGTH: 214
<212> TYPE: PRT
<213> ORGANISM: Artificial Sequence
<220> FEATURE:
<223> OTHER INFORMATION: Antibody LC

<400> SEQUENCE: 13

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

```
Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

```
<210> SEQ ID NO 14
<211> LENGTH: 122
<212> TYPE: PRT
<213> ORGANISM: Artificial Sequence
<220> FEATURE:
<223> OTHER INFORMATION: mAb 003 VH

<400> SEQUENCE: 14

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Phe Ser Trp Val Arg Gln Ala Pro Gly Gln Gly Leu Glu Trp Met
        35                  40                  45

Gly Arg Val Ile Pro Phe Leu Gly Ile Ala Asn Ser Ala Gln Lys Phe
    50                  55                  60

Gln Gly Arg Val Thr Ile Thr Ala Asp Lys Ser Thr Ser Thr Ala Tyr
65                  70                  75                  80

Met Asp Leu Ser Ser Leu Arg Ser Glu Asp Thr Ala Val Tyr Tyr Cys
                85                  90                  95

Ala Arg Asp Asp Ile Ala Ala Leu Gly Pro Phe Asp Tyr Trp Gly Gln
            100                 105                 110

Gly Thr Leu Val Thr Val Ser Ser Ala Ser
        115                 120
```

```
<210> SEQ ID NO 15
<211> LENGTH: 107
<212> TYPE: PRT
<213> ORGANISM: Artificial Sequence
<220> FEATURE:
<223> OTHER INFORMATION: mAb 003 VL

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
```

```
            35                  40                  45
Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Arg
                85                  90                  95

Thr Phe Gly Gln Gly Thr Lys Val Glu Ile Lys
            100                 105
```

<210> SEQ ID NO 16
<211> LENGTH: 122
<212> TYPE: PRT
<213> ORGANISM: Artificial Sequence
<220> FEATURE:
<223> OTHER INFORMATION: mAb 024 Vh

<400> SEQUENCE: 16

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
            20                  25                  30

Trp Ile Gly Trp Val Arg Gln Met Pro Gly Lys Gly Leu Glu Trp Met
        35                  40                  45

Gly Ile Ile Tyr Pro His Asp Ser Asp Ala Arg Tyr Ser Pro Ser Phe
    50                  55                  60

Gln Gly Gln Val Thr Phe Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Val Gly Trp Gly Ser Arg Tyr Trp Tyr Phe Asp Leu Trp
            100                 105                 110

Gly Arg Gly Thr Leu Val Thr Val Ser Ser
        115                 120
```

<210> SEQ ID NO 17
<211> LENGTH: 107
<212> TYPE: PRT
<213> ORGANISM: Artificial Sequence
<220> FEATURE:
<223> OTHER INFORMATION: mAb 024 VL

<400> SEQUENCE: 17

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys
            100                 105
```

<210> SEQ ID NO 18
<211> LENGTH: 120
<212> TYPE: PRT
<213> ORGANISM: Artificial Sequence
<220> FEATURE:
<223> OTHER INFORMATION: MOR202VH

<400> SEQUENCE: 18

```
Gln Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Asn Trp Val Arg Gln Ala Pro Gly Lys Gly Leu Glu Trp Val
        35                  40                  45

Ser Gly Ile Ser Gly Asp Pro Ser Asn Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Pro Leu Val Tyr Thr Gly Phe Ala Tyr Trp Gly Gln
            100                 105                 110

Gly Thr Leu Val Thr Val Ser Ser
        115                 120
```

<210> SEQ ID NO 19
<211> LENGTH: 109
<212> TYPE: PRT
<213> ORGANISM: Artificial Sequence
<220> FEATURE:
<223> OTHER INFORMATION: MOR202VL

<400> SEQUENCE: 19

```
Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Arg His Tyr Tyr Val
            20                  25                  30

Tyr Trp Tyr Gln Gln Lys Pro Gly Gln Ala Pro Val Leu Val Ile Tyr
        35                  40                  45

Gly Asp Ser Lys Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Tyr Thr Gly Gly Ala Ser Leu
                85                  90                  95

Val Phe Gly Gly Gly Thr Lys Leu Thr Val Leu Gly Gln
            100                 105
```

<210> SEQ ID NO 20
<211> LENGTH: 120
<212> TYPE: PRT
<213> ORGANISM: Artificial Sequence
<220> FEATURE:
<223> OTHER INFORMATION: Isatuximab VH

<400> SEQUENCE: 20

```
Gln Val Gln Leu Val Gln Ser Gly Ala Glu Val Ala Lys Pro Gly Thr
1               5                   10                  15

Ser Val Lys Leu Ser Cys Lys Ala Ser Gly Tyr Thr Phe Thr Asp Tyr
```

```
                    20                  25                  30

Trp Met Gln Trp Val Lys Gln Arg Pro Gly Gln Gly Leu Glu Trp Ile
             35                  40                  45

Gly Thr Ile Tyr Pro Gly Asp Gly Asp Thr Gly Tyr Ala Gln Lys Phe
         50                  55                  60

Gln Gly Lys Ala Thr Leu Thr Ala Asp Lys Ser Ser Lys Thr Val Tyr
 65                  70                  75                  80

Met His Leu Ser Ser Leu Ala Ser Glu Asp Ser Ala Val Tyr Tyr Cys
                 85                  90                  95

Ala Arg Gly Asp Tyr Tyr Gly Ser Asn Ser Leu Asp Tyr Trp Gly Gln
            100                 105                 110

Gly Thr Ser Val Thr Val Ser Ser
            115                 120

<210> SEQ ID NO 21
<211> LENGTH: 107
<212> TYPE: PRT
<213> ORGANISM: Artificial Sequence
<220> FEATURE:
<223> OTHER INFORMATION: Isatuximab VL

<400> SEQUENCE: 21

Asp Ile Val Met Thr Gln Ser His Leu Ser Met Ser Thr Ser Leu Gly
 1               5                  10                  15

Asp Pro Val Ser Ile Thr Cys Lys Ala Ser Gln Asp Val Ser Thr Val
                 20                  25                  30

Val Ala Trp Tyr Gln Gln Lys Pro Gly Gln Ser Pro Arg Arg Leu Ile
             35                  40                  45

Tyr Ser Ala Ser Tyr Arg Tyr Ile Gly Val Pro Asp Arg Phe Thr Gly
         50                  55                  60

Ser Gly Ala Gly Thr Asp Phe Thr Phe Thr Ile Ser Ser Val Gln Ala
 65                  70                  75                  80

Glu Asp Leu Ala Val Tyr Tyr Cys Gln Gln His Tyr Ser Pro Pro Tyr
                 85                  90                  95

Thr Phe Gly Gly Gly Thr Lys Leu Glu Ile Lys
            100                 105

<210> SEQ ID NO 22
<211> LENGTH: 509
<212> TYPE: PRT
<213> ORGANISM: Homo sapiens

<400> SEQUENCE: 22

Met Gly Val Leu Lys Phe Lys His Ile Phe Phe Arg Ser Phe Val Lys
 1               5                  10                  15

Ser Ser Gly Val Ser Gln Ile Val Phe Thr Phe Leu Leu Ile Pro Cys
                 20                  25                  30

Cys Leu Thr Leu Asn Phe Arg Ala Pro Pro Val Ile Pro Asn Val Pro
             35                  40                  45

Phe Leu Trp Ala Trp Asn Ala Pro Ser Glu Phe Cys Leu Gly Lys Phe
         50                  55                  60

Asp Glu Pro Leu Asp Met Ser Leu Phe Ser Phe Ile Gly Ser Pro Arg
 65                  70                  75                  80

Ile Asn Ala Thr Gly Gln Gly Val Thr Ile Phe Tyr Val Asp Arg Leu
                 85                  90                  95

Gly Tyr Tyr Pro Tyr Ile Asp Ser Ile Thr Gly Val Thr Val Asn Gly
            100                 105                 110
```

-continued

Gly Ile Pro Gln Lys Ile Ser Leu Gln Asp His Leu Asp Lys Ala Lys
                115                 120                 125

Lys Asp Ile Thr Phe Tyr Met Pro Val Asp Asn Leu Gly Met Ala Val
130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
                180                 185                 190

Glu Lys Ala Gly Lys Asp Phe Leu Val Glu Thr Ile Lys Leu Gly Lys
                195                 200                 205

Leu Leu Arg Pro Asn His Leu Trp Gly Tyr Tyr Leu Phe Pro Asp Cys
                210                 215                 220

Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
                260                 265                 270

Ala Ala Thr Leu Tyr Val Arg Asn Arg Val Arg Glu Ala Ile Arg Val
                275                 280                 285

Ser Lys Ile Pro Asp Ala Lys Ser Pro Leu Pro Val Phe Ala Tyr Thr
                290                 295                 300

Arg Ile Val Phe Thr Asp Gln Val Leu Lys Phe Leu Ser Gln Asp Glu
305                 310                 315                 320

Leu Val Tyr Thr Phe Gly Glu Thr Val Ala Leu Gly Ala Ser Gly Ile
                325                 330                 335

Val Ile Trp Gly Thr Leu Ser Ile Met Arg Ser Met Lys Ser Cys Leu
                340                 345                 350

Leu Leu Asp Asn Tyr Met Glu Thr Ile Leu Asn Pro Tyr Ile Ile Asn
                355                 360                 365

Val Thr Leu Ala Ala Lys Met Cys Ser Gln Val Leu Cys Gln Glu Gln
370                 375                 380

Gly Val Cys Ile Arg Lys Asn Trp Asn Ser Ser Asp Tyr Leu His Leu
385                 390                 395                 400

Asn Pro Asp Asn Phe Ala Ile Gln Leu Glu Lys Gly Gly Lys Phe Thr
                405                 410                 415

Val Arg Gly Lys Pro Thr Leu Glu Asp Leu Glu Gln Phe Ser Glu Lys
                420                 425                 430

Phe Tyr Cys Ser Cys Tyr Ser Thr Leu Ser Cys Lys Glu Lys Ala Asp
                435                 440                 445

Val Lys Asp Thr Asp Ala Val Asp Val Cys Ile Ala Asp Gly Val Cys
                450                 455                 460

Ile Asp Ala Phe Leu Lys Pro Pro Met Glu Thr Glu Pro Gln Ile
465                 470                 475                 480

Phe Tyr Asn Ala Ser Pro Ser Thr Leu Ser Ala Thr Met Phe Ile Val
                485                 490                 495

Ser Ile Leu Phe Leu Ile Ile Ser Ser Val Ala Ser Leu
                500                 505

ANTI-CD38 ANTIBODIES FOR TREATMENT OF LIGHT CHAIN AMYLOIDOSIS AND OTHER CD38-POSITIVE HEMATOLOGICAL MALIGNANCIES

RELATED APPLICATIONS

This application is a continuation of U.S. application Ser. No. 15/160,476, filed May 20, 2016, which claims the benefit of U.S. Provisional Application No. 62/164,206, filed on May 20, 2015 and claims the benefit of U.S. Provisional Application No. 62/214,586, filed on Sep. 4, 2015. The entire teachings of the above applications are incorporated herein by reference.

INCORPORATION BY REFERENCE OF MATERIAL IN ASCII TEXT FILE

This application incorporates by reference the Sequence Listing contained in the following ASCII text file being submitted concurrently herewith:
  a) File name: 01482017042_SequenceListing.txt; created Aug. 5, 2020, 26 KB in size.

FIELD OF THE INVENTION

The present invention relates to methods of treatment of light chain amyloidosis and other CD38-positive hematological malignancies.

BACKGROUND

B-cell malignancies include B-cell chronic lymphocytic leukemia, mantle cell lymphoma, Burkitt lymphoma, follicular lymphoma, diffuse large B-cell lymphoma, multiple myeloma, Hodgkin's lymphoma, hairy cell leukemia, primary effusion lymphoma and AIDS-related Non-Hodgkin's Lymphoma. B-cell malignancies comprise more than 85% of diagnosed lymphomas.

Multiple myeloma (MM) is characterized by the latent accumulation of secretory plasma cells in bone marrow with a low proliferative index and an extended life span. The disease ultimately attacks bones and bone marrow, resulting in multiple tumors and lesions throughout the skeletal system. Approximately 1% of all cancers and slightly more than 10% of all hematologic malignancies can be attributed to multiple myeloma. Incidence of multiple myeloma increases in the aging population, with the median age at time of diagnosis being about 61 years.

Light chain amyloidosis (AL) (also called systemic amyloidosis) is a clonal plasma cell disorder in which fragments of misfolded immunoglobulin light chains are deposited in tissues. Monoclonal plasma cells in the bone marrow produce the misfolded immunoglobulin light chains that accumulate in tissues and cause toxicity in vital organs leading to organ failure and death (Comenzo et al., Leukemia 26:2317-25, 2012). The clinical features depend on the organs involved; amyloidosis frequently manifests in kidneys, heart, skin, nervous system and in soft tissues, such as the tongue (Merlini and Belotti, NEJM, 349:583-596, 2003), resulting in albuminuria and renal failure, heart failure, arrhythmias, risk of sudden cardiac death, hepatomegaly, bloating, early satiety, paresthesias, dysthesias, orthostatic hypotension, constipation, or diarrhea (Chaulagain and Comenzo; Curr Hematol Malig Rep 8:291-8, 2013).

CD38 is a type II membrane protein having function in receptor-mediated adhesion and signaling as well as mediating calcium mobilization via its ecto-enzymatic activity, catalyzing formation of cyclic ADP-ribose (cADPR) from $NAD^+$ and also hydrolyzing cADPR into ADP-ribose (ADPR). CD38 mediates cytokine secretion and activation and proliferation of lymphocytes (Funaro et al., J Immunology 145:2390-6, 1990; Guse et al., Nature 398:70-3, 1999), and via its NAD glycohydrolase activity regulates extracellular $NAD^+$ levels which have been implicated in modulating the regulatory T-cell compartment (Adriouch et al., 14:1284-92, 2012; Chiarugi et al., Nature Reviews 12:741-52, 2012).

CD38 is expressed on multiple myeloma malignant plasma cells, and is implicated in various hematological malignancies.

Current treatments for light chain amyloidosis and multiple myeloma include various chemotherapeutic agents with or without autologous stem cell transplantation. However, both diseases remain largely incurable. Thus, there is a need for additional therapeutics for multiple myeloma and light chain amyloidosis.

SUMMARY

The invention provides for a method of treating a patient having a CD38-positive hematological malignancy, comprising administering to the patient in need thereof an anti-CD38 antibody for a time sufficient to treat the CD38-positive hematological malignancy, wherein the patient is undergoing hematopoietic stem cell transplantation (HSCT).

The invention also provides for a method of treating a patient having light chain amyloidosis (AL), comprising administering to the patient in need thereof an anti-CD38 antibody for a time sufficient to treat AL.

The invention also provides for a method of treating a patient having light chain amyloidosis (AL), comprising administering to the patient in need thereof an anti-CD38 antibody for a time sufficient to treat AL, wherein the patient is undergoing hematopoietic stem cell transplantation (HSCT).

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION

Figure 1:
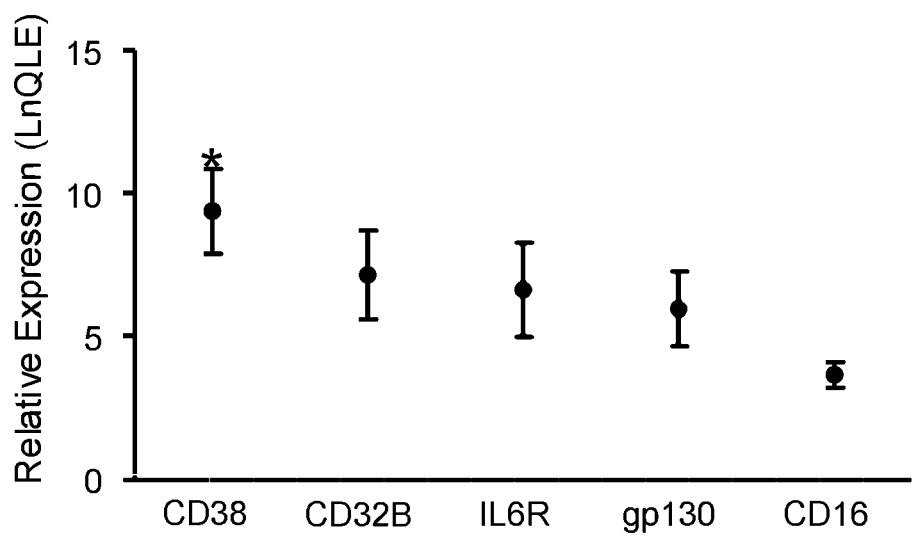
FIG. 1 shows the relative expression of CD38, CD32B, IL6R, gp130 and CD16 in transcriptional profiles of $CD138^+$ clonal plasma cells of newly diagnosed patients with AL (n=16 AL patients, GEO GSE24128). LnQLE: natural log of the quantitative level of expression.

A description of example embodiments follows.

"CD38" refers to the human CD38 protein (synonyms: ADP-ribosyl cyclase 1, cADPr hydrolase 1, cyclic ADP-ribose hydrolase 1). Human CD38 has an amino acid sequence shown in GenBank accession number NP_001766 and in SEQ ID NO: 1. it is well known that CD38 is a single pass type II membrane protein with amino acid residues 1-21 representing the cytosolic domain, amino acid residues 22-42 representing the transmembrane domain, and residues 43-300 representing the extracellular domain of CD38.

```
                                                    SEQ ID NO: 1
MANCEFSPVSGDKPCCRLSRRAQLCLGVSILVLILVVVLAVVVPRWRQQWS

GPGTTKRFPETVLARCVKYTEIHPEMRHVDCQSVWDAFKGAFISKHPCNIT

EEDYQPLMKLGTQTVPCNKILLWSRIKDLAHQFTQVQRDMFTLEDTLLGYL

ADDLTWCGEFNTSKINYQSCPDWRKDCSNNPVSVFWKTVSRRFAEAACDVV

HVMLNGSRSKIFDKNSTFGSVEVHNLQPEKVQTLEAWVIHGGREDSRDLCQ

DPTIKELESIISKRNIQFSCKNIYRPDKFLQCVKNPEDSSCTSEI
```

"Antibodies" as used herein is meant in a broad sense and includes immunoglobulin molecules including monoclonal antibodies including murine, human, human-adapted, humanized and chimeric monoclonal antibodies, antibody fragments, bispecific or multispecific antibodies, dimeric, tetrameric or multimeric antibodies, and single chain antibodies.

Immunoglobulins can be assigned to five major classes, namely IgA, IgD, IgE, IgG and IgM, depending on the heavy chain constant domain amino acid sequence. IgA and IgG are further sub-classified as the isotypes $IgA_1$, $IgA_2$, $IgG_1$, $IgG_2$, $IgG_3$ and $IgG_4$. Antibody light chains of any vertebrate species can be assigned to one of two clearly distinct types, namely kappa (κ) and lambda (λ), based on the amino acid sequences of their constant domains.

"Antibody fragments" refers to a portion of an immunoglobulin molecule that retains the heavy chain and/or the light chain antigen binding site, such as heavy chain complementarity determining regions (HCDR) 1, 2 and 3, light chain complementarity determining regions (LCDR) 1, 2 and 3, a heavy chain variable region (VH), or a light chain variable region (VL). Antibody fragments include a Fab fragment, a monovalent fragment consisting of the VL, VH, CL and CHI domains; a F(ab)$_2$ fragment, a bivalent fragment comprising two Fab fragments linked by a disulfide bridge at the hinge region; a Fd fragment consisting of the VH and CHI domains; a Fv fragment consisting of the VL and VH domains of a single arm of an antibody; a domain antibody (dAb) fragment (Ward et al., Nature 341:544-6, 1989), which consists of a VH domain. VH and VL domains can be engineered and linked together via a synthetic linker to form various types of single chain antibody designs in which the VH/VL domains pair intramolecularly, or intermolecularly in those cases in which the VH and VL domains are expressed by separate single chain antibody constructs, to form a monovalent antigen binding site, such as single chain Fv (scFv) or diabody; described for example in Intl. Pat. Publ. Nos. WO1998/44001, WO1988/01649, WO1994/13804, and WO1992/01047. These antibody fragments are obtained using known techniques known to those of skill in the art, and the fragments are screened for utility in the same manner as are full length antibodies.

"Isolated antibody" refers to an antibody or antibody fragment that is substantially free of other antibodies having different antigenic specificities (e.g., an isolated antibody specifically binding CD38 is substantially free of antibodies that specifically bind antigens other than human CD38). An isolated antibody that specifically binds CD38, however, can have cross-reactivity to other antigens, such as orthologs of human CD38, such as *Macaca fascicularis* (cynomolgus) CD38. Moreover, an isolated antibody may be substantially free of other cellular material and/or chemicals.

An antibody variable region consists of a "framework" region interrupted by three "antigen binding sites". The antigen binding sites are defined using various terms: Complementarity Determining Regions (CDRs), three in the VH (HCDR1, HCDR2, HCDR3) and three in the VL (LCDR1, LCDR2, LCDR3) are based on sequence variability (Wu and Kabat J Exp Med 132:211-50, 1970; Kabat et al Sequences of Proteins of Immunological Interest, 5th Ed. Public Health Service, National Institutes of Health, Bethesda, Md., 1991); "Hypervariable regions", "HVR", or "HV", three in the VH (H1, H2, H3) and three in the VL (L1, L2, L3) refer to the regions of an antibody variable domains which are hypervariable in structure as defined by Chothia and Lesk (Chothia and Lesk Mol Biol 196:901-17, 1987). Other terms include "IMGT-CDRs" (Lefranc et al., Dev Comparat Immunol 27:55-77, 2003) and "Specificity Determining Residue Usage" (SDRU) (Almagro, Mol Recognit 17:132-43, 2004). The International ImMunoGeneTics (IMGT) database (www_imgt_org) provides a standardized numbering and definition of antigen-binding sites. The correspondence between CDRs, HVs and IMGT delineations is described in Lefranc et al., Dev Comparat Immunol 27:55-77, 2003.

"Chothia residues" as used herein are the antibody VL and VH residues numbered according to Al-Lazikani (Al-Lazikani et al., J Mol Biol 273:927-48, 1997).

"Framework" or "framework sequences" are the remaining sequences of a variable region other than those defined to be antigen binding sites. Because the antigen binding sites can be defined by various terms as described above, the exact amino acid sequence of a framework depends on how the antigen-binding site was defined.

"Humanized antibody" refers to an antibody in which the antigen binding sites are derived from non-human species and the variable region frameworks are derived from human immunoglobulin sequences. Humanized antibodies may include substitutions in the framework regions so that the framework may not be an exact copy of expressed human immunoglobulin or germline gene sequences.

"Human-adapted" antibodies or "human framework adapted (HFA)" antibodies refers to humanized antibodies adapted according to methods described in U.S. Pat. Publ. No. US2009/0118127. Human-adapted antibodies are humanized by selecting the acceptor human frameworks based on the maximum CDR and FR similarities, length compatibilities and sequence similarities of CDR1 and CDR2 loops and a portion of light chain CDR3 loops.

"Human antibody" refers to an antibody having heavy and light chain variable regions in which both the framework and the antigen binding sites are derived from sequences of human origin. If the antibody contains a constant region, the constant region also is derived from sequences of human origin.

A human antibody comprises heavy and/or light chain variable regions that are "derived from" sequences of human origin wherein the variable regions of the antibody are obtained from a system that uses human germline immunoglobulin or rearranged immunoglobulin genes. Such systems include human immunoglobulin gene libraries displayed on phage, and transgenic non-human animals such as mice or rat carrying human immunoglobulin loci as described herein. A "human antibody" may contain amino acid differences when compared to the human germline or rearranged immunoglobulin sequences due to for example naturally occurring somatic mutations or intentional introduction of substitutions in the framework or antigen binding sites. Typically, a human antibody is at least about 80%, 81%, 82%, 83%, 84%, 85%, 86%, 87%, 88%, 89%, 90%, 91%, 92%, 93%, 94%, 95%, 96%, 97%, 98%, 99% or 100% identical in amino acid sequence to an amino acid sequence encoded by a human germline or rearranged immunoglobulin gene. In some cases, "human antibody" may contain consensus framework sequences derived from human framework sequence analyses, for example as described in Knappik et al., J Mol Biol 296:57-86, 2000, or synthetic HCDR3 incorporated into human immunoglobulin gene libraries displayed on phage, for example as described in Shi et al., J Mol Biol 397:385-96, 2010 and Intl. Pat. Publ. No. WO2009/085462). Antibodies in which antigen binding sites are derived from a non-human species are not included in the definition of human antibody.

Isolated humanized antibodies may be synthetic. Human antibodies, while derived from human immunoglobulin sequences, may be generated using systems such as phage display incorporating synthetic CDRs and/or synthetic frameworks, or can be subjected to in vitro mutagenesis to improve antibody properties, resulting in antibodies that do not naturally exist within the human antibody germline repertoire in vivo.

"Recombinant antibody" includes all antibodies that are prepared, expressed, created or isolated by recombinant means, such as antibodies isolated from an animal (for example a mouse or a rat) that is transgenic or transchromosomal for human immunoglobulin genes or a hybridoma prepared therefrom, antibodies isolated from a host cell transformed to express the antibody, antibodies isolated from a recombinant, combinatorial antibody library, and antibodies prepared, expressed, created or isolated by any other means that involve splicing of human immunoglobulin gene sequences to other DNA sequences, or antibodies that are generated in vitro using Fab arm exchange such as bispecific antibodies.

"Monoclonal antibody" refers to a preparation of antibody molecules of single molecular composition. A monoclonal antibody composition displays a single binding specificity and affinity for a particular epitope, or in a case of a bispecific monoclonal antibody, a dual binding specificity to two distinct epitopes. "Monoclonal antibody" therefore refers to an antibody population with single amino acid composition in each heavy and each light chain, except for possible well known alterations such as removal of C-terminal lysine from the antibody heavy chain. Monoclonal antibodies may have heterogeneous glycosylation within the antibody population. Monoclonal antibody may be monospecific or multispecific, or monovalent, bivalent or multivalent. A bispecific antibody is included in the term monoclonal antibody.

"Epitope" refers to a portion of an antigen to which an antibody specifically binds. Epitopes usually consist of chemically active (such as polar, non-polar or hydrophobic) surface groupings of moieties such as amino acids or polysaccharide side chains and can have specific three-dimensional structural characteristics, as well as specific charge characteristics. An epitope can be composed of contiguous and/or noncontiguous amino acids that form a conformational spatial unit. For a noncontiguous epitope, amino acids from differing portions of the linear sequence of the antigen come in close proximity in 3-dimensional space through the folding of the protein molecule.

"Variant" refers to a polypeptide or a polynucleotide that differs from a reference polypeptide or a reference polynucleotide by one or more modifications for example, substitutions, insertions or deletions.

"In combination with" means that two or more therapeutics can be administered to a subject together in a mixture, concurrently as single agents or sequentially as single agents in any order.

"Treat" or "treatment" refers to therapeutic treatment wherein the object is to slow down (lessen) an undesired physiological change or disease, or to provide a beneficial or desired clinical outcome during treatment. Beneficial or desired clinical outcomes include alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if a subject was not receiving treatment. Those in need of treatment include those subjects already with the undesired physiological change or diseases well as those subjects prone to have the physiological change or disease.

"Inhibits growth" (e.g. referring to cells, such as tumor cells) refers to a measurable decrease in the cell growth in vitro or in vivo when the cell is contacted with a therapeutic or a combination of therapeutics or drugs, when compared to the growth of the same cell grown in appropriate control conditions well known to the skilled in the art. Inhibition of growth of a cell in vitro or in vivo may be at least about 10%, 20%, 30%, 40%, 50%, 60%, 70%, 80%, 90%, 99%, or 100%. Inhibition of cell growth can occur by a variety of mechanisms, for example by antibody-dependent cell-mediated cytotoxicity (ADCC), antibody-dependent cellular phagocytosis (ADCP), complement dependent cytotoxicity (CDC), apoptosis, necrosis, or by inhibition of cell proliferation.

"Therapeutically effective amount" refers to an amount effective, at dosages and for periods of time necessary, to achieve a desired therapeutic result. A therapeutically effective amount may vary according to factors such as the disease state, age, sex, and weight of the individual, and the ability of a therapeutic or a combination of therapeutics to elicit a desired response in the individual. Exemplary indicators of an effective amount of a therapeutic or combination of therapeutics include, for example, improved well-being of the patient, reduction of a tumor burden, arrested or slowed growth of a tumor, and/or absence of metastasis of cancer cells to other locations in the body.

"Patient" includes any human or nonhuman animal. "Nonhuman animal" includes all vertebrates, e.g., mammals and non-mammals, such as nonhuman primates, sheep, dogs, cats, horses, cows chickens, amphibians, reptiles, etc. The terms "patient" and "subject" are used interchangeably herein.

The invention provides for a method of treating patients having a CD38-positive hematological malignancy undergoing hematopoietic stem cell transplantation with an anti-CD38 antibody that does not kill (e.g. mediate killing of) CD34$^+$ hematopoietic stem cells within the transplant, which cells are also CD38 positive. The invention also provides for a method for treating patients having light chain amyloidosis. The invention is based, at least in part, on the discovery that an anti-CD38 antibody DARZALEX™ (daratumumab) is effective in killing AL plasma cells, but does not kill CD38$^+$CD34$^+$ hematopoietic stem cells isolated from patients having light chain amyloidosis or multiple myeloma, allowing combination treatment with DARZALEX™ (daratumumab) and hematopoietic stem cell transplantation.

The methods of the invention may be used to treat an animal patient belonging to any classification. Examples of such animals include mammals such as humans, rodents, dogs, cats and farm animals.

The invention provides for a method of treating a patient having a CD38-positive hematological malignancy, comprising administering to the patient in need thereof an anti-CD38 antibody for a time sufficient to treat the CD38-positive hematological malignancy, wherein the patient is undergoing hematopoietic stem cell transplantation (HSCT).

"CD38-positive hematological malignancy" refers to a hematological malignancy characterized by the presence of tumor cells expressing CD38 including leukemias, lymphomas, myeloma and plasma cell disorders. Examples of CD38-positive hematological malignancies include precursor B-cell lymphoblastic leukemia/lymphoma and B-cell non-Hodgkin's lymphoma, acute promyelocytic leukemia, acute lymphoblastic leukemia and mature B-cell neoplasms, such as B-cell chronic lymphocytic leukemia (CLL)/small lymphocytic lymphoma (SLL), B-cell acute lymphocytic leukemia, B-cell prolymphocytic leukemia, lymphoplasmacytic lymphoma, mantle cell lymphoma (MCL), follicular lymphoma (FL), including low-grade, intermediate-grade and high-grade FL, cutaneous follicle center lymphoma, marginal zone B-cell lymphoma (MALT type, nodal and splenic type), hairy cell leukemia, diffuse large B-cell lymphoma (DLBCL), Burkitt's lymphoma (BL), plasmacytoma, multiple myeloma (MM), plasma cell leukemia, post-transplant lymphoproliferative disorder, Waldenstrom's macroglobulinemia, plasma cell leukemias, anaplastic large-cell lymphoma (ALCL) and light chain amyloidosis (AL).

"Plasma cell disorder" as used herein refers to disorders characterized by clonal plasma cells, and includes multiple myeloma, light chain amyloidosis and Waldenstrom's macroglobulinemia. Light chain amyloidosis and Waldenstrom's macrogloblinemia can arise independently from multiple myeloma. They may also present simultaneously with multiple myeloma, and develop either before or after the development of multiple myeloma.

The definitions "CD-38 positive hematological malignancy" and "plasma cell disorders" may thus be partially overlapping.

In some embodiments, the CD38-positive hematological malignancy is light chain amyloidosis (AL).

In some embodiments, the CD38-positive hematological malignancy is multiple myeloma (MM).

In some embodiments, the CD38-positive hematological malignancy is Waldenstrom's macroglobulinemia.

In some embodiments, the CD38-positive hematological malignancy is diffuse large B-cell lymphoma (DLBCL).

In some embodiments, the CD38-positive hematological malignancy is non-Hodgkin's lymphoma.

In some embodiments, the CD38-positive hematological malignancy is acute lymphoblastic leukemia (ALL).

In some embodiments, the CD38-positive hematological malignancy is follicular lymphoma (FL).

In some embodiments, the CD38-positive hematological malignancy is Burkitt's lymphoma (BL).

In some embodiments, the CD38-positive hematological malignancy is mantle cell lymphoma (MCL).

In some embodiments, the CD38-positive hematological malignancy is a plasma cell disorder.

In some embodiments, the CD38-positive hematological malignancy is light chain amyloidosis (AL), multiple myeloma (MM), acute lymphoblastic leukemia (ALL), non-Hodgkin's lymphoma, diffuse large B-cell lymphoma (DLBCL), Burkitt's lymphoma (BL), follicular lymphoma (FL) or mantle-cell lymphoma (MCL).

Exemplary B-cell non-Hodgkin's lymphomas are lymphomatoid granulomatosis, primary effusion lymphoma, intravascular large B-cell lymphoma, mediastinal large B-cell lymphoma, heavy chain diseases (including γ, μ, and a disease), lymphomas induced by therapy with immunosuppressive agents, such as cyclosporine-induced lymphoma, and methotrexate-induced lymphoma.

In some embodiments, the disorder involving cells expressing CD38 is Hodgkin's lymphoma.

Other examples of disorders involving cells expressing CD38 include malignancies derived from T and NK cells including mature T cell and NK cell neoplasms including T-cell prolymphocytic leukemia, T-cell large granular lymphocytic leukemia, aggressive NK cell leukemia, adult T-cell leukemia/lymphoma, extranodal NK/T cell lymphoma, nasal type, 78 enteropathy-type T-cell lymphoma, hepatosplenic T-cell lymphoma, subcutaneous panniculitis-like T-cell lymphoma, blastic NK cell lymphoma, Mycosis Fungoides/Sezary Syndrome, primary cutaneous CD30 positive T-cell lymphoproliferative disorders (primary cutaneous anaplastic large cell lymphoma C-ALCL, lymphomatoid papulosis, borderline lesions), angioimmunoblastic T-cell lymphoma, peripheral T-cell lymphoma unspecified, and anaplastic large cell lymphoma.

Examples of malignancies derived from myeloid cells include acute myeloid leukemia, including acute promyelocytic leukemia, and chronic myeloproliferative diseases, including chronic myeloid leukemia.

The invention also provides for a method of treating a patient having light chain amyloidosis (AL), comprising administering to the patient in need thereof an anti-CD38 antibody for a time sufficient to treat AL The invention also provides for a method of treating a patient having light chain amyloidosis, comprising administering to the patient in need thereof an anti-CD38 antibody for a time sufficient to treat the light chain amyloidosis, wherein the patient is undergoing hematopoietic stem cell transplantation (HSCT).

The invention also provides for a method of treating a patient having multiple myeloma, comprising administering to the patient in need thereof an anti-CD38 antibody for a time sufficient to treat the multiple myeloma, wherein the patient is undergoing hematopoietic stem cell transplantation (HSCT).

In some embodiments, the anti-CD38 antibody competes for binding to CD38 with an antibody comprising a heavy chain variable region (VH) of SEQ ID NO: 4 and a light chain variable region (VL) of SEQ ID NO: 5.

In some embodiments, the anti-CD38 antibody binds at least to the region SKRNIQFSCKNIYR (SEQ ID NO: 2) and the region EKVQTLEAWVIHGG (SEQ ID NO: 3) of human CD38 (SEQ ID NO: 1).

In some embodiments, the anti-CD38 antibody comprises a heavy chain complementarity determining region (HCDR) 1, a HCDR2 and a HCDR3 of SEQ ID NOs: 6, 7 and 8, respectively.

In some embodiments, the anti-CD38 antibody comprises a light chain complementarity determining region (LCDR) 1, a LCDR2 and a LCDR3 of SEQ ID NOs: 9, 10 and 11, respectively.

In some embodiments, the anti-CD38 antibody comprises the HCDR1, the HCDR2 and the HCDR3 of SEQ ID NOs: 6, 7 and 8, respectively, and the LCDR1, the LCDR2 and the LCDR3 of SEQ ID NOs: 9, 10 and 11, respectively.

In some embodiments, the anti-CD38 antibody comprises a heavy chain variable region (VH) amino acid sequence that is 95%, 96%, 97%, 98%, 99% or 100% identical to that of SEQ ID NO: 4 and a light chain variable region (VL) amino acid sequence that is 95%, 96%, 97%, 98%, 99% or 100% identical to that of SEQ ID NO: 5.

In some embodiments, the anti-CD38 antibody comprises the VH of SEQ ID NO: 4 and the VL of SEQ ID NO: 5.

In some embodiments, the anti-CD38 antibody comprises a heavy chain comprising an amino acid sequence that is 95%, 96%, 97%, 98%, 99% or 100% identical to that of SEQ ID NO: 12 and a light chain comprising an amino acid sequence that is 95%, 96%, 97%, 98%, 99% or 100% identical to that of SEQ ID NO: 13.

In some embodiments, the anti-CD38 antibody comprises the heavy chain of SEQ ID NO: 12 and the light chain of SEQ ID NO: 13.

The epitope of the antibody includes some or all of the residues having the sequences shown in SEQ ID NO: 2 or SEQ ID NO: 3. In some embodiments, the antibody epitope comprises at least one amino acid in the region SKRNIQFSCKNIYR (SEQ ID NO: 2) and at least one amino acid in the region EKVQTLEAWVIHGG (SEQ ID NO: 3) of human CD38 (SEQ ID NO: 1). In some embodiments, the antibody epitope comprises at least two amino acids in the region SKRNIQFSCKNIYR (SEQ ID NO: 2) and at least two amino acids in the region EKVQTLEAWVIHGG (SEQ ID NO: 3) of human CD38 (SEQ ID NO: 1). In some embodiments, the antibody epitope comprises at least three amino acids in the region SKRNIQFSCKNIYR (SEQ ID NO: 2) and at least three amino acids in the region EKVQTLEAWVIHGG (SEQ ID NO: 3) of human CD38 (SEQ ID NO: 1).

An exemplary antibody that binds to the region SKRNIQFSCKNIYR (SEQ ID NO: 2) and the region EKVQTLEAWVIHGG (SEQ ID NO: 3) of human CD38 (SEQ ID NO: 1) is DARZALEX™ (daratumumab).

An exemplary anti-CD38 antibody that may be used in the methods of the invention is DARZALEX™ (daratumumab). DARZALEX™ (daratumumab) comprises the heavy chain variable region (VH) and the light chain variable region (VL) amino acid sequences shown in SEQ ID NO: 4 and 5, respectively, heavy chain CDRs HCDR1, HCDR2 and HCDR3 of SEQ ID NOs: 6, 7 and 8, respectively, and light chain CDRs LCDR1, LCDR2 and LCDR3 of SEQ ID NOs: 9, 10 and 11, respectively, and is of IgG1/κ subtype and described in U.S. Pat. No. 7,829,693. DARZALEX™ (daratumumab) heavy chain amino acid sequence is shown in SEQ ID NO: 12 and light chain amino acid sequence shown in SEQ ID NO: 13.

Antibodies may be evaluated for their competition with a reference antibody, for example DARZALEX™ (DARZALEX™ (daratumumab)) having the VH of SEQ ID NO: 4 and the VL of SEQ ID NO: 5 for binding to CD38 using well known in vitro methods. In an exemplary method, CHO cells recombinantly expressing CD38 may be incubated with an unlabeled reference antibody for 15 min at 4° C., followed by incubation with an excess of a fluorescently labeled test antibody for 45 min at 4° C. After washing in PBS/BSA, fluorescence may be measured by flow cytometry using standard methods. In another exemplary method, the extracellular domain of CD38 may be coated on the surface of an ELISA plate. Excess of an unlabeled reference antibody may be added for about 15 minutes and subsequently a biotinylated test antibody may be added. After washes in PBS/Tween, binding of the biotinylated test antibody may be detected using horseradish peroxidase (HRP)-conjugated streptavidine and the signal detected using standard methods. It is readily apparent that in the competition assays, the reference antibody may be labelled and the test antibody unlabeled. The test antibody competes with the reference antibody when the reference antibody inhibits binding of the test antibody, or the test antibody inhibits binding of the reference antibody to CD38 by at least 80%, for example 81%, 82%, 83%, 84%, 85%, 86%, 87%, 88%, 89%, 90%, 91%, 92%, 93%, 94%, 95%, 96%, 97%, 98%, 99% or 100%. The epitope of the test antibody may further be defined for example by peptide mapping or hydrogen/deuterium protection assays using known methods, or by crystal structure determination.

Antibodies binding to the region SKRNIQFSCKNIYR (SEQ ID NO: 2) and the region EKVQTLEAWVIHGG (SEQ ID NO: 3) of human CD38 (SEQ ID NO: 1). may be generated for example by immunizing mice with peptides having the amino acid sequences shown in SEQ ID NOs: 2 and 3 using standard methods and as described herein, and characterizing the obtained antibodies for binding to the peptides using for example ELISA or mutagenesis studies.

```
                                               SEQ ID NO: 2
SKRNIQFSCKNIYR

SEQ ID NO: 3
EKVQTLEAWVIHGG

SEQ ID NO: 4
EVQLLESGGGLVQPGGSLRLSCAVSGFTFNSFAMSWVRQAPGKGLEWVSA

ISGSGGGTYYADSVKGRFTISRDNSKNTLYLQMNSLRAEDTAVYFCAKDK

ILWFGEPVFDYWGQGTLVTVSS

SEQ ID NO: 5
EIVLTQSPATLSLSPGERATLSCRASQSVSSYLAWYQQKPGQAPRLLIYD

ASNRATGIPARFSGSGSGTDFTLTISSLEPEDFAVYYCQQRSNWPPTFGQ

GTKVEIK

SEQ ID NO: 6
SFAMS

SEQ ID NO: 7
AISGSGGGTYYADSVKG

SEQ ID NO: 8
DKILWFGEPVFDY

SEQ ID NO: 9
RASQSVSSYLA

SEQ ID NO: 10
DASNRAT

SEQ ID NO: 11
QQRSNWPPTF

SEQ ID NO: 12
EVQLLESGGGLVQPGGSLRLSCAVSGFTFNSFAMSWVRQAPGKGLEWVSA

ISGSGGGTYYADSVKGRFTISRDNSKNTLYLQMNSLRAEDTAVYFCAKDK

ILWFGEPVFDYWGQGTLVTVSSASTKGPSVFPLAPSSKSTSGGTAALGCL

VKDYFPEPVTVSWNSGALTSGVHTFPAVLQSSGLYSLSSVVTVPSSSLGT

QTYICNVNHKPSNTKVDKRVEPKSCDKTHTCPPCPAPELLGGPSVFLFPP

KPKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPRE

PQVYTLPPSREEMTKNQVSLTCLVKGFYPSDIAVEWESNGQPENNYKTTP

PVLDSDGSFFLYSKLTVDKSRWQQGNVFSCSVMHEALHNHYTQKSLSLSP

GK

SEQ ID NO: 13
EIVLTQSPATLSLSPGERATLSCRASQSVSSYLAWYQQKPGQAPRLLIYD

ASNRATGIPARFSGSGSGTDFTLTISSLEPEDFAVYYCQQRSNWPPTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC
```

Other exemplary anti-CD38 antibodies that may be used in the methods of the invention are:

mAb003 comprising the VH and VL sequences of SEQ ID NOs: 14 and 15, respectively and described in U.S. Pat. No. 7,829,693. The VH and the VL of mAb003 may be expressed as IgG1/κ.

```
                                               SEQ ID NO: 14
QVQLVQSGAEVKKPGSSVKVSCKASGGTFSSYAFSWVRQAPGQGLEWMGR

VIPFLGIANSAQKFQGRVTITADKSTSTAYMDLSSLRSEDTAVYYCARDD

IAALGPFDYWGQGTLVTVSSAS

SEQ ID NO: 15
DIQMTQSPSSLSASVGDRVTITCRASQGISSWLAWYQQKPEKAPKSLIYA

ASSLQSGVPSRFSGSGSGTDFTLTISSLQPEDFATYYCQQYNSYPRTFGQ

GTKVEIK;
``` mAb024 comprising the VH and VL sequences of SEQ ID NOs: 16 and 17, respectively, described in U.S. Pat. No. 7,829,693. The VH and the VL of mAb024 may be expressed as IgG1/κ.

SEQ ID NO: 16
EVQLVQSGAEVKKPGESLKISCKGSGYSFSNYWIGWVRQMPGKGLEWMGI

IYPHDSDARYSPSFQGQVTFSADKSISTAYLQWSSLKASDTAMYYCARHV

GWGSRYWYFDLWGRGTLVTVSS

SEQ ID NO: 17
EIVLTQSPATLSLSPGERATLSCRASQSVSSYLAWYQQKPGQAPRLLIYD

ASNRATGIPARFSGSGSGTDFTLTISSLEPEDFAVYYCQQRSNWPPTFGQ

GTKVEIK;

MOR-202 (MOR-03087) comprising the VH and VL sequences of SEQ ID NOs: 18 and 19, respectively, described in U.S. Pat. No. 8,088,896. The VH and the VL of MOR-202 may be expressed as IgG1/κ.

SEQ ID NO: 18
QVQLVESGGGLVQPGGSLRLSCAASGFTFSSYYMNWVRQAPGKGLEWVSG

ISGDPSNTYYADSVKGRFTISRDNSKNTLYLQMNSLRAEDTAVYYCARDL

PLVYTGFAYWGQGTLVTVSS

SEQ ID NO: 19
DIELTQPPSVSVAPGQTARISCSGDNLRHYYVYWYQQKPGQAPVLVIYGD

SKRPSGIPERFSGSNSGNTATLTISGTQAEDEADYYCQTYTGGASLVFGG

GTKLTVLGQ;

Isatuximab; comprising the VH and VL sequences of SEQ ID NOs: X and X, respectively, described in U.S. Pat. No. 8,153,765. The VH and the VL of Isatuximab may be expressed as IgG1/κ.

SEQ ID NO 20:
QVQLVQSGAEVAKPGTSVKLSCKASGYTFTDYWMQWVKQRPGQGLEWIGT

IYPGDGDTGYAQKFQGKATLTADKSSKTVYMHLSSLASEDSAVYYCARGD

YYGSNSLDYWGQGTSVTVSS

SEQ ID NO: 21:
DIVMTQSHLSMSTSLGDPVSITCKASQDVSTVVAWYQQKPGQSPRRLIYS

ASYRYIGVPDRFTGSGAGTDFTFTISSVQAEDLAVYYCQQHYSPPYTFGG

GTKLEIK

Other exemplary anti-CD38 antibodies that may be used in the methods of the invention include those described in Int. Pat. Publ. No. WO05/103083, Intl. Pat. Publ. No. WO06/125640, Intl. Pat. Publ. No. WO07/042309, Intl. Pat. Publ. No. WO08/047242 or Intl. Pat. Publ. No. WO14/178820.

In some embodiments, AL is cardiac stage I, cardiac stage II or cardiac stage III.

In some embodiments, AL is relapsed or refractory.

AL diagnosis is performed by a physician according to guidelines available for example at National Comprehensive Cancer Network (www_nccn.org/professionals/physician_gls/_f_guidelines_asp#site). AL patients present damage in various organ systems due to accumulation of light chains and their misfolded intermediates as amyloid fibers in vital organs, causing organ dysfunction and mortality. Patients may have multiple organ systems affected at diagnosis; about one third of patients have more than 3 organs affected at diagnosis (Chaulagain and Comenzo Curr Hematol Malig Rep 8:291-8, 2013). AL prognosis involves cardiac staging as cardiac damage appears to be present in all AL patients at diagnosis even if the patient is asymptomatic (Palladini et al., Blood 116:3426-30, 2010; Kristen et al., Blood 116: 2455-61, 2010). Based on the presence of one, two or both cardiac biomarkers N-terminal prohormone of brain natriuretic peptide (NT-proBNP) and troponin T, AL patients may be classified to cardiac stage I, II or III, see e.g. Comenzo et al., Leukemia 26:2317-25, 2012.

Current treatment options for AL are directed towards killing the light chain immunoglobulin secreting plasma cells, and include a combination of agents such as Velcade® (bortezomib), cyclophosphamide such as Cytoxan® or Neosar®, Alkeran® (melphalan), Thalomid® (thalidomide), Revlimid® (lenalidomide), or Pomalyst® (pomalidomide) as well as steroids (dexamethasone), interferon alpha (IFN-α) and stem cell transplantation. High-dose Alkeran® (melphalan) may be used with stem cell transplantation (see for example Anderson et al., Systemic light chain amyloidosis, NCCN Clinical Practice Guidelines in Oncology Version 1.2015, NCCN.org. 2014). NINLARO® (ixazomib), a proteasome inhibitor, is being evaluated for treatment of AL. NEOD001, a monoclonal antibody targeting AL amyloid protein is being evaluated for treatment of AL.

In some embodiments, MM is relapsed or refractory.

Currently available therapies for MM include chemotherapy, stem cell transplantation, Thalomid® (thalidomide), Revlimid® (lenalidomide), Velcade® (bortezomib), Kyprolis® (carfilzomib), Farydak® (panobinostat), Aredia® (pamidronate), and Zometa® (zoledronic acid). Current treatment protocols, which include a combination of chemotherapeutic agents such as Oncovin® (vincristine), BiCNU® (BCNU, carmustine), Alkeran® (melphalan), cyclophosphamide, Adriamycin® (doxorubicin), and prednisone or dexamethasone, yield a complete remission rate of only about 5%, and median survival is approximately 36-48 months from the time of diagnosis. Further, the investigational agent ixazomib has achieved positive results from a key clinical trial in relapsed multiple myeloma patients. Recent advances using high dose chemotherapy followed by autologous bone marrow or peripheral blood mononuclear cell transplantation have increased the complete remission rate and remission duration, yet overall survival has only been slightly prolonged, and no evidence for a cure has been obtained. Ultimately, all MM patients relapse, even under maintenance therapy with interferon-alpha (IFN-α) alone or in combination with steroids.

Various qualitative and/or quantitative methods may be used to determine relapse or refractory nature of the disease. Symptoms that may be associated with relapse or resistance are, for example, a decline or plateau of the well-being of the patient or re-establishment or worsening of various symptoms associated with hematological malignancy, and/or the spread of cancerous cells in the body from one location to other organs, tissues or cells. The symptoms associated with hematological malignancy may vary according to the type of cancer. For example, symptoms associated with AL may include increased fatigue, purpura, enlarged tongue, diarrhea or edema, proteinurea, or increased plasma free light chain.

In some embodiments, the HSCT is allogeneic, autologous or syngeneic, i.e. the donor is a twin. Autologous HSCT comprises the extraction of HSC from the subject and freezing of the harvested HSC. After myeloablation, the subject's stored HSC are transplanted into the subject.

Allogeneic HSCT involves HSC obtained from an allogeneic HSC donor who has an HLA type that matches the subject.

"Hematopoietic stem cell transplantation" as used herein is the transplantation of blood stem cells derived from the bone marrow (in this case known as bone marrow transplantation), blood (such as peripheral blood and umbilical cord blood), or amniotic fluid.

"Undergoing hematopoietic stem cell transplantation" as used herein means that the patient did already receive, is receiving or will receive HSCT.

In some embodiments, the patient has completed chemotherapy and/or radiation therapy prior to HSCT.

Patients may be treated with chemotherapy and/or radiation therapy prior to HSCT (so-called pre-transplant preparation) to eradicate some or all of the patient's hematopoietic cells prior to transplant. The patient may also be treated with immunosuppressants in case of allogeneic HSCT. An exemplary pre-transplant preparation therapy is high-dose melphalan (see for example Skinner et al., Ann Intern Med 140:85-93, 2004; Gertz et al., Bone Marrow Transplant 34: 1025-31, 2004; Perfetti et al., Haematologica 91:1635-43, 2006). The radiation therapy which may be employed in pre-transplant treatment may be carried out according to commonly known protocols in this field. Radiation therapy may also be provided simultaneously, sequentially or separately with the anti-CD38 antibody.

DARZALEX™ (daratumumab) may not mediate killing CD38$^+$CD34$^+$ stem cells within the transplant and hence is a suitable therapy to combine with HSCT. Antibodies competing with daratumumab, and/or antibodies binding the same epitope as DARZALEX™ (daratumumab) may also not kill CD38$^+$CD34$^+$ stem cells.

Other exemplary antibodies that can be used in the methods of the invention disclosed herein may not kill CD38$^+$CD34$^+$ stem cells within the transplant and hence are suitable therapies to combine with HSCT. Inability of the antibodies to kill CD38$^+$CD34$^+$ stem cells within the transplant can be assessed using the methods described herein.

Anti-CD38 antibodies used in the methods of the invention may also be selected de novo from, e.g., a phage display library, where the phage is engineered to express human immunoglobulins or portions thereof such as Fabs, single chain antibodies (scFv), or unpaired or paired antibody variable regions (Knappik et al., J Mol Biol 296:57-86, 2000; Krebs et al., J Immunol Meth 254:67-84, 2001; Vaughan et al., Nature Biotechnology 14:309-314, 1996; Sheets et al., PITAS (USA) 95:6157-6162, 1998; Hoogenboom and Winter, J Mol Biol 227:381, 1991; Marks et al., J Mol Biol 222:581, 1991). CD38 binding variable domains may be isolated from e.g., phage display libraries expressing antibody heavy and light chain variable regions as fusion proteins with bacteriophage pIX coat protein as described in Shi et al., J. Mol. Biol. 397:385-96, 2010 and Intl. Pat. Publ. No. WO09/085462). The antibody libraries may be screened for binding to human CD38 extracellular domain, obtained positive clones further characterized, Fabs isolated from the clone lysates, and subsequently cloned as full length antibodies. Such phage display methods for isolating human antibodies are established in the art. See for example: U.S. Pat. Nos. 5,223,409; 5,403,484; and 5,571,698, 5,427,908, 5,580,717, 5,969,108, 6,172,197, 5,885,793; 6,521,404; 6,544,731; 6,555,313; 6,582,915; and 6,593,081.

In some embodiments described herein, the anti-CD38 antibody does not mediate killing CD34-positive hematopoietic progenitor cells by complement dependent cytotoxicity (CDC).

"Does not kill" or "does not mediate killing of" refers to the inability of the anti-CD38 antibody to induce cell killing when compared to an appropriate control, such as an isotype control. The anti-CD38 antibody "does not kill" when the measured killing of cells in the presence of DARZALEX™ (daratumumab) is not statistically significant when compared to the killing of cells in the presence of an isotype control. Isotype control is a well-known term.

CD34-positive hematopoietic progenitor cell killing by CDC may be measured in fresh or frozen isolated CD34$^+$ cells by incubating the cells in 10% serum with complement and 500 ng/ml anti-CD38 antibody, followed by assaying the degree of colony formation of the cells plated in semisolid medium according to known methods. For example, BFU-E and CFU-GM formation may be assessed after 14 days in culture using commercial reagents such as MethoCult™ by Stem Cell Technologies.

The Fc portion of the antibody may mediate antibody effector functions such as antibody-dependent cell-mediated cytotoxicity (ADCC), antibody-dependent cellular phagocytosis (ADCP) or complement dependent cytotoxicity (CDC). Such function may be mediated by binding of an Fc effector domain(s) to an Fc receptor on an immune cell with phagocytic or lytic activity or by binding of an Fc effector domain(s) to components of the complement system. Typically, the effect(s) mediated by the Fc-binding cells or complement components result in inhibition and/or depletion of target cells, for example CD38-expressing cells. Human IgG isotypes IgG1, IgG2, IgG3 and IgG4 exhibit differential capacity for effector functions. ADCC may be mediated by IgG1 and IgG3, ADCP may be mediated by IgG1, IgG2, IgG3 and IgG4, and CDC may be mediated by IgG1 and IgG3.

In some embodiments, the anti-CD38 antibody is of IgG1, IgG2, IgG3 or IgG4 isotype.

In some embodiments, the anti-CD38 antibody induces killing of CD38 expressing plasma cells in vitro by antibody-dependent cell-mediated cytotoxicity (ADCC), antibody-dependent cellular phagocytosis (ADCP), complement dependent cytotoxicity (CDC), apoptosis, or in vitro modulation of CD38 enzymatic activity.

In some embodiments, the anti-CD38 antibody induces killing of CD38 expressing cells in vitro by ADCC, ADCP or CDC.

In some embodiments, the anti-CD38 antibody induces killing of CD38 expressing cells in vitro by ADCC.

In some embodiments, the anti-CD38 antibody induces killing of CD38 expressing cells in vitro by ADCP.

In some embodiments, the anti-CD38 antibody induces killing of CD38 expressing cells in vitro by CDC.

"Antibody-dependent cellular cytotoxicity", "antibody-dependent cell-mediated cytotoxicity" or "ADCC" is a mechanism for inducing cell death that depends upon the interaction of antibody-coated target cells with effector cells possessing lytic activity, such as natural killer cells, monocytes, macrophages and neutrophils via Fc gamma receptors (FcγR) expressed on effector cells. For example, NK cells express FcγRIIIa, whereas monocytes express FcγRT, FcγRII and FcγRIIIa. Death of the antibody-coated target cell, such as CD38-expressing cells, occurs as a result of effector cell activity through the secretion of membrane pore-forming proteins and proteases. To assess ADCC activity of an anti-CD38 antibody, the antibody may be added to CD38-expressing cells in combination with immune effector cells, which may be activated by the antigen antibody complexes resulting in cytolysis of the target cell. Cytolysis is generally detected by the release of label (e.g. radioactive substrates, fluorescent dyes or natural intracellular proteins) from the lysed cells. Exemplary effector cells for such assays include peripheral blood mononuclear cells (PBMC) and NK cells. Exemplary target cells include Daudi cells (ATCC® CCL-213™) or B cell leukemia or lymphoma tumor cells expressing CD38. In an exemplary assay, target cells are labeled with 20 µCi of $^{51}$Cr for 2 hours and washed extensively. Cell concentration of the target cells can be adjusted to 1×10$^6$ cells/ml, and anti-CD38 antibodies at various concentrations are added. Assays are started by adding Daudi cells at an effector:target cell ratio of 40:1. After incubation for 3 hr at 37° C., assays are stopped by centrifugation, and $^{51}$Cr release from lysed cells are measured in a scintillation counter. Percentage of cellular cytotoxicity may be calculated as % maximal lysis which may be induced by adding 3% perchloric acid to target cells. Anti-CD38 antibodies used in the methods of the invention may induce ADCC by about 20%, 25%, 30%, 35%, 40%, 45%, 50%, 55%, 60%, 65%, 70%, 75%, 80%, 85%, 90%, 95% or 100% of control (cell lysis induced by 3% perchloric acid).

"Antibody-dependent cellular phagocytosis" ("ADCP") refers to a mechanism of elimination of antibody-coated target cells by internalization by phagocytic cells, such as macrophages or dendritic cells. ADCP may be evaluated by using monocyte-derived macrophages as effector cells and Daudi cells (ATCC® CCL-213™) or B cell leukemia or lymphoma tumor cells expressing CD38 as target cells engineered to express GFP or other labeled molecule. Effector:target cell ratio may be for example 4:1. Effector cells may be incubated with target cells for 4 hours with or without anti-CD38 antibody. After incubation, cells may be detached using accutase. Macrophages can be identified with anti-CD11b and anti-CD14 antibodies coupled to a fluorescent label, and percent phagocytosis can be determined based on % GFP fluorescent in the CD11$^+$CD14$^+$ macrophages using standard methods. Anti-CD38 antibodies used in the methods of the invention may induce ADCP by about 20%, 25%, 30%, 35%, 40%, 45%, 50%, 55%, 60%, 65%, 70%, 75%, 80%, 85%, 90%, 95% or 100%.

"Complement-dependent cytotoxicity", or "CDC", refers to a mechanism for inducing cell death in which an Fc effector domain of a target-bound antibody binds and activates complement component C1q which in turn activates the complement cascade leading to target cell death. Activation of complement may also result in deposition of complement components on the target cell surface that facilitate ADCC by binding complement receptors (e.g., CR3) on leukocytes. CDC of CD38-expressing cells can be measured for example by plating Daudi cells at 1×10$^5$ cells/well (50 µl/well) in RPMI-B (RPMI supplemented with 1% BSA), adding 50 µl anti-CD38 antibodies to the wells at final concentration between 0-100 µg/ml, incubating the reaction for 15 min at room temperature, adding 11 µl of pooled human serum to the wells, and incubation the reaction for 45 min at 37° C. Percentage (%) lysed cells may be detected as % propidium iodide stained cells in FACS assay using standard methods. Anti-CD38 antibodies used in the methods of the invention may induce CDC by about 20%, 25%, 30%, 35%, 40%, 45%, 50%, 55%, 60%, 65%, 70%, 75%, 80%, 85%, 90%, 95% or 100%.

The ability of monoclonal antibodies to induce ADCC can be enhanced by engineering their oligosaccharide component. Human IgG1 or IgG3 are N-glycosylated at Asn297 with the majority of the glycans in the well-known biantennary G0, G0F, G1, G1F, G2 or G2F forms. Antibodies produced by non-engineered CHO cells typically have a glycan fucose content of about at least 85%. The removal of the core fucose from the biantennary complex-type oligosaccharides attached to the Fc regions enhances the ADCC of antibodies via improved FcγRIIIa binding without altering antigen binding or CDC activity. Such mAbs can be achieved using different methods reported to lead to the successful expression of relatively high defucosylated antibodies bearing the biantennary complex-type of Fc oligosaccharides such as control of culture osmolality (Konno et al., Cytotechnology 64:249-65, 2012), application of a variant CHO line Lec13 as the host cell line (Shields et al., J Biol Chem 277:26733-40, 2002), application of a variant CHO line EB66 as the host cell line (Olivier et al., MAbs 2(4), 2010; Epub ahead of print; PMID:20562582), application of a rat hybridoma cell line YB2/0 as the host cell line (Shinkawa et al., J Biol Chem 278:3466-73, 2003), introduction of small interfering RNA specifically against the α 1,6-fucosyltrasferase (FUT8) gene (Mori et al., Biotechnol Bioeng 88:901-8, 2004), or coexpression of β-1,4-N-acetylglucosaminyltransferase III and Golgi α-mannosidase II or a potent alpha-mannosidase I inhibitor, kifunensine (Ferrara et al., J Biol Chem 281:5032-6, 2006; Ferrara et al., Biotechnol Bioeng 93:851-61, 2006; Xhou et al., Biotechnol Bioeng 99:652-65, 2008). ADCC elicited by anti-CD38 antibodies used in the methods of the invention, and in some embodiments of each and every one of the numbered embodiments listed below, may also be enhanced by certain substitutions in the antibody Fc. Exemplary substitutions are for example substitutions at amino acid positions 256, 290, 298, 312, 356, 330, 333, 334, 360, 378 or 430 (residue numbering according to the EU index) as described in U.S. Pat. No. 6,737,056. CDC elicited by anti-CD38 antibodies used in the methods of the invention, and in some embodiments of each and every one of the numbered embodiments listed below, may also be enhanced by certain substitutions in the antibody Fc. Exemplary substitutions are, for example, substitutions at amino acid positions 423, 268, 267 and/or 113 (residue numbering according to the EU index) as described in Moore et al., Mabs 2:181-9, 2010.

In some embodiments, the anti-CD38 antibody comprises a substitution in the antibody Fc.

In some embodiments, the anti-CD38 antibody comprises a substitution in the antibody Fc at amino acid positions 256, 290, 298, 312, 356, 330, 333, 334, 360, 378 and/or 430 (residue numbering according to the EU index).

In some embodiments, the anti-CD38 antibody comprises a substitution in the antibody Fc at amino acid position 113, 267, 268 and/or 423 (residue numbering according to the EU index).

In some embodiments, the anti-CD38 antibody comprises has a biantennary glycan structure with fucose content of about between 0% to about 15%, for example 15%, 14%, 13%, 12%, 11% 10%, 9%, 8%, 7%, 6%, 5%, 4%, 3%, 2%, 1% or 0%.

In some embodiments, the anti-CD38 antibody comprises has a biantennary glycan structure with fucose content of about 50%, 40%, 45%, 40%, 35%, 30%, 25%, 20%, 15%, 14%, 13%, 12%, 11%, 10%, 9%, 8%, 7%, 6%, 5%, 4%, 3%, 2%, 1% or 0%

Substitutions in the Fc and reduced fucose content may enhance the ADCC activity of the anti-CD38 antibody.

"Fucose content" means the amount of the fucose monosaccharide within the sugar chain at Asn297. The relative amount of fucose is the percentage of fucose-containing structures related to all glycostructures. These may be characterized and quantified by multiple methods, for example: 1) using MALDI-TOF of N-glycosidase F treated sample (e.g. complex, hybrid and oligo- and high-mannose structures) as described in Intl. Pat. Publ. No. WO2008/077546; 2) by enzymatic release of the Asn297 glycans with subsequent derivatization and detection/quantitation by HPLC (UPLC) with fluorescence detection and/or HPLC-MS (UPLC-MS); 3) intact protein analysis of the native or reduced mAb, with or without treatment of the Asn297 glycans with Endo S or other enzyme that cleaves between the first and the second GlcNAc monosaccharides, leaving the fucose attached to the first GlcNAc; 4) digestion of the mAb to constituent peptides by enzymatic digestion (e.g., trypsin or endopeptidase Lys-C), and subsequent separation, detection and quantitation by HPLC-MS (UPLC-MS) or 5) separation of the mAb oligosaccharides from the mAb protein by specific enzymatic deglycosylation with PNGase F at Asn 297. The oligosaccharides released can be labeled with a fluorophore, separated and identified by various complementary techniques which allow: fine characterization of the glycan structures by matrix-assisted laser desorption ionization (MALDI) mass spectrometry by comparison of the experimental masses with the theoretical masses, determination of the degree of sialylation by ion exchange HPLC (GlycoSep C), separation and quantification of the oligosacharride forms according to hydrophilicity criteria by normal-phase HPLC (GlycoSep N), and separation and quantification of the oligosaccharides by high performance capillary electrophoresis-laser induced fluorescence (HPCE-LIF).

"Low fucose" or "low fucose content" as used in the application refers to antibodies with fucose content of about 0%-15%.

"Normal fucose" or 'normal fucose content" as used herein refers to antibodies with fucose content of about over 50%, typically about over 60%, 70%, 80% or over 85%.

The anti-CD38 antibody used in the methods of the invention may induce killing of CD38-expressing cells by apoptosis in vitro. Methods for evaluating apoptosis are well known, and include for example annexin IV staining using standard methods. The anti-CD38 antibody in the methods of the invention may induce apoptosis in about 20%, 25%, 30%, 35%, 40%, 45%, 50%, 55%, 60%, 65%, 70%, 75%, 80%, 85%, 90%, 95% or 100% of cells.

The anti-CD38 antibody used in the methods of the invention may induce in vitro killing of CD38-expressing cells by modulation of CD38 enzymatic activity. CD38 is a multifunctional ectoenzme with ADP-ribosyl cyclase 1 activity catalyzing the formation of cyclic ADP-ribose (cADPR) and ADPR from $NAD^+$, and also functions to hydrolyze $NAD^+$ and cADPR to ADPR. CD38 also catalyzes the exchange of the nicotinamide group of $NADP^+$ with nicotinic acid under acidic conditions, to yield $NAADP^+$ (nicotinic acid-adenine dinucleotide phosphate). Modulation of the enzymatic activity of human CD38 with anti-CD38 antibodies used in the methods of the invention may be measured in an assay described in Graeff et al., J. Biol. Chem. 269:30260-7, 1994). For example, substrate $NGD^+$ may be incubated with CD38, and the modulation of the production of cyclic GDP-ribose (cGDPR) may be monitored spectrophotometrically at excitation at 340 nM and emission at 410 nM at different time points after addition of the antibody at various concentrations. Inhibition of the synthesis of cADPR may be determined according to the HPLC method described in Munshi et al., J. Biol. Chem. 275: 21566-71, 2000. The anti-CD38 antibodies used in the methods of the invention may inhibit CD38 enzymatic activity by at least about 20%, 25%, 30%, 35%, 40%, 45%, 50%, 55%, 60%, 65%, 70%, 75%, 80%, 85%, 90%, 95% or 100%.

Antibodies that are substantially identical to the antibody comprising the VH of SEQ ID NO: 4 and the VL of SEQ ID NO: 5 may be used in the methods of the invention. The term "substantially identical" means that the antibody VH or VL amino acid sequences being compared are identical or have "insubstantial differences". Insubstantial differences are substitutions of 1, 2, 3, 4, 5, 6, 7, 8, 9, 10, 11, 12, 13, 14, or 15 amino acids in the antibody VL and/or VL that do not adversely affect antibody properties. Percent identity may be determined for example by pairwise alignment using the default settings of the AlignX module of Vector NTI v.9.0.0 (Invitrogen, Carlsbad, CA). The protein sequences of the present invention may be used as a query sequence to perform a search against public or patent databases to, for example, identify related sequences. Exemplary programs used to perform such searches are the XBLAST or BLASTP programs (www_ncbi_nlm/nih_gov), or the GenomeQuest™ (GenomeQuest, Westborough, MA) suite using the default settings. Exemplary substitutions that may be made to the antibodies that specifically bind CD38 used in the methods of the invention are for example conservative substitutions with an amino acid having similar charge, hydrophobic, or stereochemical characteristics. Conservative substitutions may also be made to improve antibody properties, for example stability or affinity, or to improve antibody effector functions. 1, 2, 3, 4, 5, 6, 7, 8, 9, 10, 11, 12, 13, 14, or 15 amino acid substitutions may be made for example to the VH and/or the VL of the anti-CD38. Furthermore, any native residue in the heavy or light chain may also be substituted with alanine, as has been previously described for alanine scanning mutagenesis (MacLennan et al., Acta Physiol Scand Suppl 643:55-67, 1998; Sasaki et al., Adv Biophys 35:1-24, 1998). Desired amino acid substitutions may be determined by those skilled in the art at the time such substitutions are desired. Amino acid substitutions may be done for example by PCR mutagenesis (U.S. Pat. No. 4,683,195). Libraries of variants may be generated using well known methods, for example using random (NNK) or non-random codons, for example DVK codons, which encode 11 amino acids (Ala, Cys, Asp, Glu, Gly, Lys, Asn, Arg, Ser, Tyr, Trp) and screening the libraries for variants with desired properties. The generated variants may be tested for their binding to CD38, their ability to induce ADCC, ADCP or apoptosis, or modulate CD38 enzymatic activity in vitro using methods described herein.

"Conservative modifications" refer to amino acid modifications that do not significantly affect or alter the binding characteristics of the antibody containing the amino acid sequences. Conservative modifications include amino acid substitutions, additions and deletions. Conservative substitutions are those in which the amino acid is replaced with an amino acid residue having a similar side chain. The families of amino acid residues having similar side chains are well defined and include amino acids with acidic side chains (e.g., aspartic acid, glutamic acid), basic side chains (e.g., lysine, arginine, histidine), nonpolar side chains (e.g., alanine, valine, leucine, isoleucine, proline, phenylalanine, methionine), uncharged polar side chains (e.g., glycine, asparagine, glutamine, cysteine, serine, threonine, tyrosine, tryptophan), aromatic side chains (e.g., phenylalanine, tryptophan, histidine, tyrosine), aliphatic side chains (e.g., glycine, alanine, valine, leucine, isoleucine, serine, threonine), amide (e.g., asparagine, glutamine), beta-branched side chains (e.g., threonine, valine, isoleucine) and sulfur-containing side chains (cysteine, methionine). Furthermore, any native residue in the polypeptide may also be substituted with alanine, as has been previously described for alanine scanning mutagenesis (MacLennan et al., (1988) *Acta Physiol Scand Suppl* 643:55-67; Sasaki et al., (1988) *Adv Biophys* 35:1-24). Amino acid substitutions to the antibodies of the invention may be made by known methods for example by PCR mutagenesis (U.S. Pat. No. 4,683,195). Alternatively, libraries of variants may be generated for example using random (NNK) or non-random codons, for example DVK codons, which encode 11 amino acids (Ala, Cys, Asp, Glu, Gly, Lys, Asn, Arg, Ser, Tyr, Trp). The resulting antibody variants may be tested for their characteristics using assays described herein.

In some embodiments, the antibody may bind CD38 with a dissociation constant ($K_D$) of less than about $1\times10^{-7}$ M, $1\times10^{-8}$ M, $1\times10^{-9}$ M, $1\times10^{-10}$ M, $1\times10^{-11}$ M, $1\times10^{-12}$ M, $1\times10^{-13}$ M, $1\times10^{-14}$ M or $1\times10^{-15}$, as determined by surface plasmon resonance or the Kinexa method, as practiced by those of skill in the art. In some embodiments, the antibody binds human CD38 with a $K_D$ of less than about $1\times10^{-8}$ M. In some embodiments, the antibody binds human CD38 with a $K_D$ of less than about $1\times10^{-9}$ M.

KinExA instrumentation, ELISA or competitive binding assays known to those skilled in the art. The measured affinity of a particular antibody/CD38 interaction may vary if measured under different conditions (e.g., osmolarity, pH). Thus, measurements of affinity and other binding parameters (e.g., $K_D$, $K_{on}$, $K_{off}$) are typically made with standardized conditions and a standardized buffer, such as the buffer described herein. Skilled in the art will appreciate that the internal error for affinity measurements for example using Biacore 3000 or ProteOn (measured as standard deviation, SD) may typically be within 5-33% for measurements within the typical limits of detection. Therefore the term "about" in the context of $K_D$ reflects the typical standard deviation in the assay. For example, the typical SD for a $K_D$ of $1\times10^{-9}$ M is up to $\pm0.33\times10^{-9}$ M.

In some embodiments, the anti-CD38 antibody is a bispecific antibody. The VL and/or the VH regions of the existing anti-CD38 antibodies or the VL and VH regions identified de novo as described above may be engineered into bispecific full length antibodies. Such bispecific antibodies may be made by modulating the CH3 interactions between the monospecific antibody heavy chains to form bispecific antibodies using technologies such as those described in U.S. Pat. No. 7,695,936; Intl. Pat. Publ. No. WO04/111233; U.S. Pat. Publ. No. US2010/0015133; U.S. Pat. Publ. No. US2007/0287170; Intl. Pat. Publ. No. WO2008/119353; U.S. Pat. Publ. No. US2009/0182127; U.S. Pat. Publ. No. US2010/0286374; U.S. Pat. Publ. No. US2011/0123532; Intl. Pat. Publ. No. WO2011/131746; Int. Pat. Publ. No. WO2011/143545; or U.S. Pat. Publ. No. US2012/0149876. Additional bispecific structures into which the VL and/or VH regions of the antibodies of the invention may be incorporated are for example Dual Variable Domain Immunoglobulins (Inlt. Pat. Publ. No. WO2009/134776), or structures that include various dimerization domains to connect the two antibody arms with different specificity, such as leucine zipper or collagen dimerization domains (Int. Pat. Publ. No. WO2012/022811, U.S. Pat. Nos. 5,932,448; 6,833,441).

For example, bispecific antibodies may be generated in vitro in a cell-free environment by introducing asymmetrical mutations in the CH3 regions of two monospecific homodimeric antibodies and forming the bispecific heterodimeric antibody from two parent monospecific homodimeric antibodies in reducing conditions to allow disulfide bond isomerization according to methods described in Intl. Pat. Publ. No. WO2011/131746. In the methods, the first monospecific bivalent antibody (e.g., anti-CD38 antibody) and the second monospecific bivalent antibody are engineered to have certain substitutions at the CH3 domain that promote heterodimer stability; the antibodies are incubated together under reducing conditions sufficient to allow the cysteines in the hinge region to undergo disulfide bond isomerization; thereby generating the bispecific antibody by Fab arm exchange. The incubation conditions may optimally be restored to non-reducing. Exemplary reducing agents that may be used are 2-mercaptoethylamine (2-MEA), dithiothreitol (DTT), dithioerythritol (DTE), glutathione, tris(2-carboxyethyl)phosphine (TCEP), L-cysteine and beta-mercaptoethanol, preferably a reducing agent selected from the group consisting of: 2-mercaptoethylamine, dithiothreitol and tris(2-carboxyethyl)phosphine. For example, incubation for at least 90 min at a temperature of at least 20° C. in the presence of at least 25 mM 2-MEA or in the presence of at least 0.5 mM dithiothreitol at a pH of from 5-8, for example at pH of 7.0 or at pH of 7.4 may be used.

Exemplary CH3 mutations that may be used in a first heavy chain and in a second heavy chain of the bispecific antibody are K409R and/or F405L.

In some embodiments, the anti-CD38 antibody is conjugated to a toxin. Conjugation methods and suitable toxins are well known.

In some embodiments, the subject having AL is homozygous for phenylalanine at position 158 of CD16 (FcγRIIIa-158F/F genotype) or heterozygous for valine and pheynylalanine at position 158 of CD16 (FcγRIIIa-158F/V genotype). CD16 is also known as the Fc gamma receptor IIIa (FcγRIIIa) or the low affinity immunoglobulin gamma Fc region receptor III-A isoform. Valine/phenylalanine (V/F) polymorphism at FcγRIIIa protein residue position 158 has been shown to affect FcγRIIIa affinity to human IgG. Receptor with FcγRIIIa-158F/F or FcγRIIIa-158F/V polymorphisms demonstrates reduced Fc engagement and therefore reduced ADCC when compared to the FcγRIIIa-158V/V. The lack of or low amount of fucose on human N-linked oligosaccharides improves the ability of the antibodies to induce ADCC due to improved binding of the antibodies to human FcγRIIIa (CD16) (Shields et al., J Biol Chem 277: 26733-40, 2002). Patients can be analyzed for their FcγRIIIa polymorphism using routine methods.

The invention also provides for a method of treating a subject having AL, comprising administering to the patient in need thereof an anti-CD38 antibody that binds to the region SKRNIQFSCKNIYR (SEQ ID NO: 2) and the region EKVQTLEAWVIHGG (SEQ ID NO: 3) of human CD38 (SEQ ID NO: 1), wherein the anti-CD38 antibody induces in vitro killing of CD38-expressing pathogenic plasma cells by antibody-dependent cell-mediated cytotoxicity (ADCC), antibody-dependent cellular phagocytosis (ADCP), complement dependent cytotoxicity (CDC), apoptosis, or in vitro modulation of CD38 enzymatic activity, wherein the subject is homozygous for valine at position 158 of CD16.

The invention also provides for a method of treating a subject having AL, comprising administering to the patient in need thereof an anti-CD38 antibody that binds to the region SKRNIQFSCKNIYR (SEQ ID NO: 2) and the region EKVQTLEAWVIHGG (SEQ ID NO: 3) of human CD38 (SEQ ID NO: 1), wherein the anti-CD38 antibody induces in vitro killing of CD38-expressing pathogenic plasma cells by antibody-dependent cell-mediated cytotoxicity (ADCC), antibody-dependent cellular phagocytosis (ADCP), complement dependent cytotoxicity (CDC), apoptosis, or in vitro modulation of CD38 enzymatic activity, wherein the subject is homozygous for phenylalanine at position 158 of CD16 or heterozygous for valine and pheynylalanine at position 158 of CD16.

The invention also provides for a method of treating a patient having AL, comprising administering to the patient in need thereof an anti-CD38 antibody that competes for binding to CD38 with an antibody comprising a heavy chain variable region (VH) of SEQ ID NO: 4 and a light chain variable region (VL) of SEQ ID NO: 5, wherein the anti-CD38 antibody induces in vitro killing of CD38-positive pathogenic plasma cells by antibody-dependent cell-mediated cytotoxicity (ADCC), antibody-dependent cellular phagocytosis (ADCP), complement dependent cytotoxicity (CDC), apoptosis, or in vitro modulation of CD38 enzymatic activity, wherein the patient is homozygous for valine at position 158 of CD16.

The invention also provides for a method of treating a patient having AL, comprising administering to the patient in need thereof an anti-CD38 antibody that competes for binding to CD38 with an antibody comprising a heavy chain variable region (VH) of SEQ ID NO: 4 and a light chain variable region (VL) of SEQ ID NO: 5, wherein the anti-CD38 antibody induces in vitro killing of CD38-positive pathogenic plasma cells by antibody-dependent cell-mediated cytotoxicity (ADCC), antibody-dependent cellular phagocytosis (ADCP), complement dependent cytotoxicity (CDC), apoptosis, or in vitro modulation of CD38 enzymatic activity, wherein the patient is homozygous for phenylalanine at position 158 of CD16 or heterozygous for valine and pheynylalanine at position 158 of CD16.

The invention also provides for the method of treating a patient having AL, comprising
- determining that the patient is homozygous or heterozygous for valine at position 158 of CD16; and
- administering to the patient an anti-CD38 antibody that competes for binding to CD38 with an antibody comprising a heavy chain variable region (VH) of SEQ ID NO: 4 and a light chain variable region (VL) of SEQ ID NO: 5; comprises the heavy chain complementarity determining regions (HCDR) 1 (HCDR1), 2 (HCDR2) and 3 (HCDR3) sequences of SEQ ID NOs: 6, 7 and 8, respectively, and the light chain complementarity determining regions (LCDR) 1 (LCDR1), 2 (LCDR2) and 3 (LCDR3) sequences of SEQ ID NOs: 9, 10 and 11, respectively; or comprises the heavy chain variable region (VH) of SEQ ID NO: 4 and the light chain variable region (VL) of SEQ ID NO: 5 for a time sufficient to treat the patient.

In some embodiments, the determining that the patient is homozygous or heterozygous for valine at position 158 of CD16 is done by polymerase chain reaction (PCR) and sequencing.

Administration/Pharmaceutical Compositions

In the methods of the invention, the anti-CD38 antibody may be provided in suitable pharmaceutical compositions comprising the anti-CD38 antibody and a pharmaceutically acceptable carrier. The carrier may be diluent, adjuvant, excipient, or vehicle with which the anti-CD38 antibody is administered. Such vehicles may be liquids, such as water and oils, including those of petroleum, animal, vegetable or synthetic origin, such as peanut oil, soybean oil, mineral oil, sesame oil and the like. For example, 0.4% saline and 0.3% glycine can be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc.

The concentration of the anti-CD38 antibody in such pharmaceutical formulation may vary widely, i.e., from less than about 0.5%, usually to at least about 1% to as much as 15 or 20%, 25%, 30%, 35%, 40%, 45% or 50% by weight and will be selected primarily based on required dose, fluid volumes, viscosities, etc., according to the particular mode of administration selected. Suitable vehicles and formulations, inclusive of other human proteins, e.g., human serum albumin, are described, for example, in e.g. Remington: The Science and Practice of Pharmacy, 21st Edition, Troy, D. B. ed., Lipincott Williams and Wilkins, Philadelphia, PA 2006, Part 5, Pharmaceutical Manufacturing pp 691-1092, see especially pp. 958-989.

The mode of administration of the anti-CD38 antibody may be any suitable route such as parenteral administration, e.g., intradermal, intramuscular, intraperitoneal, intravenous or subcutaneous, pulmonary, transmucosal (oral, intranasal, intravaginal, rectal) or other means appreciated by the skilled artisan, as well known in the art.

The anti-CD38 antibody in the methods of the invention may be administered to a patient by any suitable route, for example parentally by intravenous (i.v) infusion or bolus injection, intramuscularly or subcutaneously or intraperitoneally. i.v. infusion may be given over for example 15, 30, 60, 90, 120, 180, or 240 minutes, or from 1, 2, 3, 4, 5, 6, 7, 8, 9, 10, 11 or 12 hours.

The dose of the anti-CD38 antibody given to a patient is sufficient to alleviate or at least partially arrest the disease being treated ("therapeutically effective amount") and may be sometimes 0.005 mg to about 100 mg/kg, e.g. about 0.05 mg to about 30 mg/kg or about 5 mg to about 25 mg/kg, or about 4 mg/kg, about 8 mg/kg, about 16 mg/kg or about 24 mg/kg, or for example about 1, 2, 3, 4, 5, 6, 7, 8, 9 or 10 mg/kg, but may even higher, for example about 15, 16, 17, 18, 19, 20, 21, 22, 23, 24, 25, 30, 40, 50, 60, 70, 80, 90 or 100 mg/kg.

A fixed unit dose may also be given, for example, 50, 100, 200, 500 or 1000 mg, or the dose may be based on the patient's surface area, e.g., 500, 400, 300, 250, 200, or 100 mg/m$^2$. Usually between 1 and 8 doses, (e.g., 1, 2, 3, 4, 5, 6, 7 or 8) may be administered to treat AL, but 9, 10, 11, 12, 13, 14, 15, 16, 17, 18, 19, 20 or more doses may be given.

The administration of the anti-CD38 antibody in the methods of the invention may be repeated after one day, two days, three days, four days, five days, six days, one week, two weeks, three weeks, one month, five weeks, six weeks, seven weeks, two months, three months, four months, five months, six months or longer. Repeated courses of treatment are also possible, as is chronic administration. The repeated administration may be at the same dose or at a different dose. For example, the anti-CD38 antibody may be administered at 8 mg/kg or at 16 mg/kg at weekly interval for 8 weeks, followed by administration at 8 mg/kg or at 16 mg/kg every two weeks for an additional 16 weeks, followed by administration at 8 mg/kg or at 16 mg/kg every four weeks by intravenous infusion.

In some embodiments, the anti-CD38 antibody is administered at 16 mg/kg once a week for 8 weeks, followed by administration at 16 mg/kg once every two weeks for 16 weeks, followed by administration at 16 mg/kg once every four weeks until discontinuation.

In some embodiments, the anti-CD38 antibody is administered at 8 mg/kg once a week for 8 weeks, followed by administration at 8 mg/kg once every two weeks for 16 weeks, followed by administration at 8 mg/kg once every four weeks until discontinuation.

In some embodiments, the anti-CD38 antibody is administered at 16 mg/kg once a week for 4 weeks, followed by administration at 16 mg/kg once every two weeks for 16 weeks, followed by administration at 16 mg/kg once every four weeks until discontinuation.

In some embodiments, the anti-CD38 antibody is administered at 8 mg/kg once a week for 4 weeks, followed by administration at 8 mg/kg once every two weeks for 16 weeks, followed by administration at 8 mg/kg once every four weeks until discontinuation.

The anti-CD38 antibody may be administered as maintenance therapy, such as, e.g., once a week for a period of 6 months or more.

For example, the anti-CD38 antibody may be provided as a daily dosage in an amount of about 0.1-100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses of every 24, 12, 8, 6, 4, or 2 hours, or any combination thereof.

The anti-CD38 antibody may also be administered prophylactically in order to reduce the risk of developing cancer, delay the onset of the occurrence of an event in cancer progression, and/or reduce the risk of recurrence when a cancer is in remission. This may be especially useful in patients wherein it is difficult to locate a tumor that is known to be present due to other biological factors.

The anti-CD38 antibody may be lyophilized for storage and reconstituted in a suitable carrier prior to use. This technique has been shown to be effective with conventional protein preparations and well known lyophilization and reconstitution techniques can be employed.

Subcutaneous Administration of Pharmaceutical Compositions Comprising an Antibody That Specifically Binds CD38 and a Hyaluronidase The anti-CD38 antibody may be administered as a pharmaceutical composition comprising the anti-CD38 antibody and a hyaluronidase subcutaneously.

The concentration of the anti-CD38 antibody in the pharmaceutical composition administered subcutaneously may be about 20 mg/ml.

The pharmaceutical composition administered subcutaneously may comprise between about 1,200 mg-1,800 mg of the anti-CD38 antibody.

The pharmaceutical composition administered subcutaneously may comprise about 1,200 mg of the anti-CD38 antibody.

The pharmaceutical composition administered subcutaneously may comprise about 1,600 mg of the anti-CD38 antibody.

The pharmaceutical composition administered subcutaneously may comprise about 1,800 mg of the anti-CD38 antibody.

The pharmaceutical composition administered subcutaneously may comprise between about 30,000 U-45,000 U of the hyaluronidase.

The pharmaceutical composition administered subcutaneously may comprise about 1,200 mg of the anti-CD38 antibody and about 30,000 U of the hyaluronidase.

The pharmaceutical composition administered subcutaneously may comprise about 1,800 mg of the anti-CD38 antibody and about 45,000 U of the hyaluronidase.

The pharmaceutical composition administered subcutaneously may comprise about 1,600 mg of the anti-CD38 antibody and about 30,000 U of the hyaluronidase.

The pharmaceutical composition administered subcutaneously may comprise about 1,600 mg of the anti-CD38 antibody and about 45,000 U of the hyaluronidase.

The pharmaceutical composition administered subcutaneously may comprise the hyaluronidase rHuPH20 having the amino acid sequence of SEQ ID NO: 22.

rHuPH20 is a recombinant hyaluronidase (HYLENEX® recombinant) and is described in Int. Pat. Publ. No. WO2004/078140.

Hyaluronidase is an enzyme that degrades hyaluronic acid (EC 3.2.1.35) and lowers the viscosity of hyaluronan in the extracellular matrix, thereby increasing tissue permeability.

SEQ ID NO: 22
MGVLKFKHIFFRSFVKSSGVSQIVFTFLLIPCCLTLNFRAPPVIPNVPFL

WAWNAPSEFCLGKFDEPLDMSLFSFIGSPRINATGQGVTIFYVDRLGYYP

YIDSITGVTVNGGIPQKISLQDHLDKAKKDITFYMPVDNLGMAVIDWEEW

RPTWARNWKPKDVYKNRSIELVQQQNVQLSLTEATEKAKQEFEKAGKDFL

VETIKLGKLLRPNHLWGYYLFPDCYNEIHYKKPGYNGSCFNVEIKRNDDL

SWLWNESTALYPSIYLNTQQSPVAATLYVRNRVREAIRVSKIPDAKSPLP

VFAYTRIVFTDQVLKFLSQDELVYTFGETVALGASGIVIWGTLSIMRSMK

SCLLLDNYMETILNPYIINVTLAAKMCSQVLCQEQGVCIRKNWNSSDYLH

LNPDNFAIQLEKGGKFTVRGKPTLEDLEQFSEKFYCSCYSTLSCKEKADV

KDTDAVDVCIADGVCIDAFLKPPMETEEPQIFYNASPSTLSATMFIVSIL

FLIISSVASL

The administration of the pharmaceutical composition comprising the anti-CD38 antibody and the hyaluronidase may be repeated after one day, two days, three days, four days, five days, six days, one week, two weeks, three weeks, four weeks, five weeks, six weeks, seven weeks, two months, three months, four months, five months, six months or longer. Repeated courses of treatment are also possible, as is chronic administration. The repeated administration may be at the same dose or at a different dose. For example, the pharmaceutical composition comprising the anti-CD38 antibody and the hyaluronidase may be administered once weekly for eight weeks, followed by once in two weeks for 16 weeks, followed by once in four weeks. The pharmaceutical compositions to be administered may comprise about 1,200 mg of the anti-CD38 antibody and about 30,000 U of hyaluronidase, wherein the concentration of the antibody that specifically binds CD38 in the pharmaceutical composition is about 20 mg/ml. The pharmaceutical compositions to be administered may comprise about 1,800 mg of the anti-CD38 antibody and about 45,000 U of hyaluronidase. The pharmaceutical compositions to be administered may comprise about 1,600 mg of the anti-CD38 antibody and about 30,000 U of hyaluronidase. The pharmaceutical compositions to be administered may comprise about 1,600 mg of the anti-CD38 antibody and about 45,000 U of hyaluronidase.

The pharmaceutical composition comprising the anti-CD38 antibody and the hyaluronidase may be administered subcutaneously to the abdominal region.

The pharmaceutical composition comprising the anti-CD38 antibody and the hyaluronidase may be administered in a total volume of about 80 ml, 90 ml, 100 ml, 110 ml or 120 ml.

For administration, 20 mg/ml of the anti-CD38 antibody in 25 mM sodium acetate, 60 mM sodium chloride, 140 mM D-mannitol, 0.04% polysorbate 20, pH 5.5 may be mixed with rHuPH20, 1.0 mg/mL (75-150 kU/mL) in 10 mM L-Histidine, 130 mM NaCl, 10 mM L-Methionine, 0.02% Polysorbate 80, pH 6.5 prior to administration of the mixture to a subject.

Combination Therapies

The anti-CD38 antibody may be administered in combination with a second therapeutic agent.

The invention also provides for a method of treating light chain amyloidosis (AL), comprising administering to a patient in need thereof an anti-CD38 antibody in combination with a proteasome inhibitor for a time sufficient to treat AL.

The invention also provides for a method of treating light chain amyloidosis (AL), comprising administering to a patient in need thereof an anti-CD38 antibody in combination with a proteasome inhibitor and a corticosteroid for a time sufficient to treat AL.

The invention also provides for a method of treating light chain amyloidosis (AL), comprising administering to a patient in need thereof an anti-CD38 antibody in combination with a proteasome inhibitor, a corticosteroid and a cyclophosphamide for a time sufficient to treat AL.

In some embodiments, the second therapeutic agent is a proteasome inhibitor.

In some embodiments, the proteasome inhibitor is Velcade® (bortezomib), or vinca alkaloids, for example vincristine or an anthracycline, such as doxorubicin.

In some embodiments, the second therapeutic agent is a corticosteroid.

In some embodiments, the corticosteroid is dexamethasone.

In some embodiments, the corticosteroid is prednisone.

In some embodiments, the second therapeutic agent is a cyclophosphamide.

In some embodiments, the second therapeutic agent is a glutamic acid derivative.

In some embodiments, the glutamic acid derivative is Thalomid® (thalidomide), Revlimid® (lenalidomide), Actimid® (CC4047).

In some embodiments, the second therapeutic agent is Velcade® (bortezomib), cyclophosphamide such as Cytoxan® or Neosar®, Alkeran® (melphalan), Thalomid® (thalidomide), Revlimid® (lenalidomide), or Pomalyst® (pomalidomide), a corticosteroid (dexamethasone), interferon alpha (IFN-α), stem cell transplantation, Ninlaro® (ixazomib) or NEOD001.

Bortezomib may be administered at 1.3 mg/m$^2$ SQ twice weekly or once weekly

Cyclophosphamide may be administered IV (intermittent therapy) 40-50 mg/kg (400-1800 mg/m$^2$) divided over 2-5 days; may be repeated at intervals of 2-4 weeks; IV (continuous daily therapy): 60-120 mg/m$^2$/day (1-2.5 mg/kg/day);

PO (intermittent therapy): 400-1000 mg/m$^2$ divided over 4-5 days or

PO (continuous daily therapy): 50-100 mg/m$^2$/day or 1-5 mg/kg/day.

Dexamethasone may be administered 40 mg/week, or 20 mg pre- and post-dose with the anti-CD38 antibody.

Melphalan may be administered 9 mg/m$^2$, orally, once daily on Days 1 to 4 of each cycle up to Cycle 9.

Thalidomide may be administered 200 mg orally once daily.

Lenalidomide may be administered 25 mg/day orally on days 1-21 for each cycle.

Pomalidomide may be administered 4 mg orally on days 1-21 of repeated 28-day cycle.

Ixazomib may be administered at 24 mg/kg IV every 28 days.

The invention also provides for a method of treating light chain amyloidosis (AL), comprising administering to a patient in need thereof an anti-CD38 antibody comprising the HCDR1, the HCDR2 and the HCDR3 of SEQ ID NOs: 6, 7 and 8, respectively and the LCDR1, the LCDR3 and the LCDR3 of SEQ ID NOs: 9, 10 and 11, respectively, in combination with bortezomib for a time sufficient to treat AL.

The invention also provides for a method of treating light chain amyloidosis (AL), comprising administering to a patient in need thereof an anti-CD38 antibody comprising the HCDR1, the HCDR2 and the HCDR3 of SEQ ID NOs: 6, 7 and 8, respectively and the LCDR1, the LCDR3 and the LCDR3 of SEQ ID NOs: 9, 10 and 11, respectively, in combination with bortezomib and cyclophosphamide for a time sufficient to treat AL.

The invention also provides for a method of treating light chain amyloidosis (AL), comprising administering to a patient in need thereof an anti-CD38 antibody comprising the HCDR1, the HCDR2 and the HCDR3 of SEQ ID NOs: 6, 7 and 8, respectively and the LCDR1, the LCDR3 and the LCDR3 of SEQ ID NOs: 9, 10 and 11, respectively, in combination with bortezomib, cyclophosphamide and a corticosteroid for a time sufficient to treat AL.

The invention also provides for a method of treating light chain amyloidosis (AL), comprising administering to a patient in need thereof an anti-CD38 antibody comprising the HCDR1, the HCDR2 and the HCDR3 of SEQ ID NOs: 6, 7 and 8, respectively and the LCDR1, the LCDR3 and the LCDR3 of SEQ ID NOs: 9, 10 and 11, respectively, in combination with bortezomib, cyclophosphamide and dexamethasone for a time sufficient to treat AL.

The invention also provides for a method of treating light chain amyloidosis (AL), comprising administering to a patient in need thereof an anti-CD38 antibody comprising the HCDR1, the HCDR2 and the HCDR3 of SEQ ID NOs: 6, 7 and 8, respectively and the LCDR1, the LCDR3 and the LCDR3 of SEQ ID NOs: 9, 10 and 11, respectively, in combination with bortezomib and a corticosteroid for a time sufficient to treat AL.

The invention also provides for a method of treating light chain amyloidosis (AL), comprising administering to a patient in need thereof an anti-CD38 antibody comprising the HCDR1, the HCDR2 and the HCDR3 of SEQ ID NOs: 6, 7 and 8, respectively and the LCDR1, the LCDR3 and the LCDR3 of SEQ ID NOs: 9, 10 and 11, respectively, in combination with bortezomib and dexamethasone for a time sufficient to treat AL.

The invention also provides for a method of treating light chain amyloidosis (AL), comprising administering to a patient in need thereof an anti-CD38 antibody comprising the HCDR1, the HCDR2 and the HCDR3 of SEQ ID NOs: 6, 7 and 8, respectively and the LCDR1, the LCDR3 and the LCDR3 of SEQ ID NOs: 9, 10 and 11, respectively, in combination with melphalan for a time sufficient to treat AL.

The invention also provides for a method of treating light chain amyloidosis (AL), comprising administering to a patient in need thereof an anti-CD38 antibody comprising the HCDR1, the HCDR2 and the HCDR3 of SEQ ID NOs: 6, 7 and 8, respectively and the LCDR1, the LCDR3 and the LCDR3 of SEQ ID NOs: 9, 10 and 11, respectively, in combination with bortezomib and melphalan for a time sufficient to treat AL.

The invention also provides for a method of treating light chain amyloidosis (AL), comprising administering to a patient in need thereof an anti-CD38 antibody comprising the HCDR1, the HCDR2 and the HCDR3 of SEQ ID NOs: 6, 7 and 8, respectively and the LCDR1, the LCDR3 and the LCDR3 of SEQ ID NOs: 9, 10 and 11, respectively, in combination with bortezomib, melphalan and a corticosteroid for a time sufficient to treat AL.

The invention also provides for a method of treating light chain amyloidosis (AL), comprising administering to a patient in need thereof an anti-CD38 antibody comprising the HCDR1, the HCDR2 and the HCDR3 of SEQ ID NOs: 6, 7 and 8, respectively and the LCDR1, the LCDR3 and the LCDR3 of SEQ ID NOs: 9, 10 and 11, respectively, in combination with bortezomib, melphalan and dexamethasone for a time sufficient to treat AL.

The invention also provides for a method of treating light chain amyloidosis (AL), comprising administering to a patient in need thereof an anti-CD38 antibody comprising the HCDR1, the HCDR2 and the HCDR3 of SEQ ID NOs: 6, 7 and 8, respectively and the LCDR1, the LCDR3 and the LCDR3 of SEQ ID NOs: 9, 10 and 11, respectively, in combination with IFN-α for a time sufficient to treat AL.

The invention also provides for a method of treating light chain amyloidosis (AL), comprising administering to a patient in need thereof an anti-CD38 antibody comprising the HCDR1, the HCDR2 and the HCDR3 of SEQ ID NOs: 6, 7 and 8, respectively and the LCDR1, the LCDR3 and the LCDR3 of SEQ ID NOs: 9, 10 and 11, respectively, in combination with IFN-α and a corticosteroid for a time sufficient to treat AL.

The invention also provides for a method of treating light chain amyloidosis (AL), comprising administering to a patient in need thereof an anti-CD38 antibody comprising the HCDR1, the HCDR2 and the HCDR3 of SEQ ID NOs: 6, 7 and 8, respectively and the LCDR1, the LCDR3 and the LCDR3 of SEQ ID NOs: 9, 10 and 11, respectively, in combination with IFN-α and dexamethasone for a time sufficient to treat AL.

The invention also provides for a method of treating light chain amyloidosis (AL), comprising administering to a patient in need thereof an anti-CD38 antibody comprising the HCDR1, the HCDR2 and the HCDR3 of SEQ ID NOs: 6, 7 and 8, respectively and the LCDR1, the LCDR3 and the LCDR3 of SEQ ID NOs: 9, 10 and 11, respectively, in combination with lenalinomide for a time sufficient to treat AL.

The invention also provides for a method of treating light chain amyloidosis (AL), comprising administering to a patient in need thereof an anti-CD38 antibody comprising the HCDR1, the HCDR2 and the HCDR3 of SEQ ID NOs: 6, 7 and 8, respectively and the LCDR1, the LCDR3 and the LCDR3 of SEQ ID NOs: 9, 10 and 11, respectively, in combination with lenalinomide and cyclophosphamide for a time sufficient to treat AL.

The invention also provides for a method of treating light chain amyloidosis (AL), comprising administering to a patient in need thereof an anti-CD38 antibody comprising the HCDR1, the HCDR2 and the HCDR3 of SEQ ID NOs: 6, 7 and 8, respectively and the LCDR1, the LCDR3 and the LCDR3 of SEQ ID NOs: 9, 10 and 11, respectively, in combination with lenalinomide, cyclophosphamide and a corticosteroid for a time sufficient to treat AL.

The invention also provides for a method of treating light chain amyloidosis (AL), comprising administering to a patient in need thereof an anti-CD38 antibody comprising the HCDR1, the HCDR2 and the HCDR3 of SEQ ID NOs: 6, 7 and 8, respectively and the LCDR1, the LCDR3 and the LCDR3 of SEQ ID NOs: 9, 10 and 11, respectively, in combination with lenalinomide, cyclophosphamide and dexamethasone for a time sufficient to treat AL.

The invention also provides for a method of treating light chain amyloidosis (AL), comprising administering to a patient in need thereof an anti-CD38 antibody comprising the HCDR1, the HCDR2 and the HCDR3 of SEQ ID NOs: 6, 7 and 8, respectively and the LCDR1, the LCDR3 and the LCDR3 of SEQ ID NOs: 9, 10 and 11, respectively, in combination with pomalinomide for a time sufficient to treat AL.

The invention also provides for a method of treating light chain amyloidosis (AL), comprising administering to a patient in need thereof an anti-CD38 antibody comprising the HCDR1, the HCDR2 and the HCDR3 of SEQ ID NOs: 6, 7 and 8, respectively and the LCDR1, the LCDR3 and the LCDR3 of SEQ ID NOs: 9, 10 and 11, respectively, in combination with pomalinomide and a corticosteroid for a time sufficient to treat AL.

The invention also provides for a method of treating light chain amyloidosis (AL), comprising administering to a patient in need thereof an anti-CD38 antibody comprising the HCDR1, the HCDR2 and the HCDR3 of SEQ ID NOs: 6, 7 and 8, respectively and the LCDR1, the LCDR3 and the LCDR3 of SEQ ID NOs: 9, 10 and 11, respectively, in combination with pomalinomide and dexamethasone for a time sufficient to treat AL.

The invention also provides for a method of treating light chain amyloidosis (AL), comprising administering to a patient in need thereof an anti-CD38 antibody comprising the HCDR1, the HCDR2 and the HCDR3 of SEQ ID NOs: 6, 7 and 8, respectively and the LCDR1, the LCDR3 and the LCDR3 of SEQ ID NOs: 9, 10 and 11, respectively, in combination with thalidomide for a time sufficient to treat AL.

The invention also provides for a method of treating light chain amyloidosis (AL), comprising administering to a patient in need thereof an anti-CD38 antibody comprising the HCDR1, the HCDR2 and the HCDR3 of SEQ ID NOs: 6, 7 and 8, respectively and the LCDR1, the LCDR3 and the LCDR3 of SEQ ID NOs: 9, 10 and 11, respectively, in combination with thalidomide and a corticosteroid for a time sufficient to treat AL.

The invention also provides for a method of treating light chain amyloidosis (AL), comprising administering to a patient in need thereof an anti-CD38 antibody comprising the HCDR1, the HCDR2 and the HCDR3 of SEQ ID NOs: 6, 7 and 8, respectively and the LCDR1, the LCDR3 and the LCDR3 of SEQ ID NOs: 9, 10 and 11, respectively, in combination with thalidomide and dexamethasone for a time sufficient to treat AL.

The invention also provides for a method of treating light chain amyloidosis (AL), comprising administering to a patient in need thereof an anti-CD38 antibody comprising the HCDR1, the HCDR2 and the HCDR3 of SEQ ID NOs: 6, 7 and 8, respectively and the LCDR1, the LCDR3 and the LCDR3 of SEQ ID NOs: 9, 10 and 11, respectively, in combination with ixazomib for a time sufficient to treat AL.

The invention also provides for a method of treating light chain amyloidosis (AL), comprising administering to a patient in need thereof an anti-CD38 antibody comprising the VH of SEQ ID NO: 4 and the VL of SEQ ID NO: 5 in combination with bortezomib for a time sufficient to treat light chain amyloidosis (AL) for a time sufficient to treat AL.

The invention also provides for a method of treating light chain amyloidosis (AL), comprising administering to a patient in need thereof an anti-CD38 antibody comprising the VH of SEQ ID NO: 4 and the VL of SEQ ID NO: 5 in combination with bortezomib and cyclophosphamide for a time sufficient to treat AL.

The invention also provides for a method of treating light chain amyloidosis (AL), comprising administering to a patient in need thereof an anti-CD38 antibody comprising the VH of SEQ ID NO: 4 and the VL of SEQ ID NO: 5 in combination with bortezomib, cyclophosphamide and a corticosteroid for a time sufficient to treat AL.

The invention also provides for a method of treating light chain amyloidosis (AL), comprising administering to a patient in need thereof an anti-CD38 antibody comprising the VH of SEQ ID NO: 4 and the VL of SEQ ID NO: 5 in combination with bortezomib, cyclophosphamide and dexamethasone for a time sufficient to treat AL.

The invention also provides for a method of treating light chain amyloidosis (AL), comprising administering to a patient in need thereof an anti-CD38 antibody comprising the VH of SEQ ID NO: 4 and the VL of SEQ ID NO: 5 in combination with bortezomib and a corticosteroid for a time sufficient to treat AL.

The invention also provides for a method of treating light chain amyloidosis (AL), comprising administering to a patient in need thereof an anti-CD38 antibody comprising the VH of SEQ ID NO: 4 and the VL of SEQ ID NO: 5 in combination with bortezomib and dexamethasone for a time sufficient to treat AL.

The invention also provides for a method of treating light chain amyloidosis (AL), comprising administering to a patient in need thereof an anti-CD38 antibody comprising the VH of SEQ ID NO: 4 and the VL of SEQ ID NO: 5 in combination with melphalan for a time sufficient to treat AL.

The invention also provides for a method of treating light chain amyloidosis (AL), comprising administering to a patient in need thereof an anti-CD38 antibody comprising the VH of SEQ ID NO: 4 and the VL of SEQ ID NO: 5 in combination with bortezomib and melphalan for a time sufficient to treat AL.

The invention also provides for a method of treating light chain amyloidosis (AL), comprising administering to a patient in need thereof an anti-CD38 antibody comprising the VH of SEQ ID NO: 4 and the VL of SEQ ID NO: 5 in combination with bortezomib, melphalan and a corticosteroid for a time sufficient to treat AL.

The invention also provides for a method of treating light chain amyloidosis (AL), comprising administering to a patient in need thereof an anti-CD38 antibody comprising the VH of SEQ ID NO: 4 and the VL of SEQ ID NO: 5 in combination with bortezomib, melphalan and dexamethasone for a time sufficient to treat AL.

The invention also provides for a method of treating light chain amyloidosis (AL), comprising administering to a patient in need thereof an anti-CD38 antibody comprising the VH of SEQ ID NO: 4 and the VL of SEQ ID NO: 5 in combination with IFN-α for a time sufficient to treat AL.

The invention also provides for a method of treating light chain amyloidosis (AL), comprising administering to a patient in need thereof an anti-CD38 antibody comprising the VH of SEQ ID NO: 4 and the VL of SEQ ID NO: 5 in combination with IFN-α and a corticosteroid for a time sufficient to treat AL.

The invention also provides for a method of treating light chain amyloidosis (AL), comprising administering to a patient in need thereof an anti-CD38 antibody comprising the VH of SEQ ID NO: 4 and the VL of SEQ ID NO: 5 in combination with IFN-α and dexamethasone for a time sufficient to treat AL.

The invention also provides for a method of treating light chain amyloidosis (AL), comprising administering to a patient in need thereof an anti-CD38 antibody comprising the VH of SEQ ID NO: 4 and the VL of SEQ ID NO: 5 in combination with lenalinomide for a time sufficient to treat AL.

The invention also provides for a method of treating light chain amyloidosis (AL), comprising administering to a patient in need thereof an anti-CD38 antibody comprising the VH of SEQ ID NO: 4 and the VL of SEQ ID NO: 5 in combination with lenalinomide and cyclophosphamide for a time sufficient to treat AL.

The invention also provides for a method of treating light chain amyloidosis (AL), comprising administering to a patient in need thereof an anti-CD38 antibody comprising the VH of SEQ ID NO: 4 and the VL of SEQ ID NO: 5 in combination with lenalinomide, cyclophosphamide and a corticosteroid for a time sufficient to treat AL.

The invention also provides for a method of treating light chain amyloidosis (AL), comprising administering to a patient in need thereof an anti-CD38 antibody comprising the VH of SEQ ID NO: 4 and the VL of SEQ ID NO: 5 in combination with lenalinomide, cyclophosphamide and dexamethasone for a time sufficient to treat AL.

The invention also provides for a method of treating light chain amyloidosis (AL), comprising administering to a patient in need thereof an anti-CD38 antibody comprising the VH of SEQ ID NO: 4 and the VL of SEQ ID NO: 5 in combination with pomalinomide for a time sufficient to treat AL.

The invention also provides for a method of treating light chain amyloidosis (AL), comprising administering to a patient in need thereof an anti-CD38 antibody comprising the VH of SEQ ID NO: 4 and the VL of SEQ ID NO: 5 in combination with pomalinomide and a corticosteroid for a time sufficient to treat AL.

The invention also provides for a method of treating light chain amyloidosis (AL), comprising administering to a patient in need thereof an anti-CD38 antibody comprising the VH of SEQ ID NO: 4 and the VL of SEQ ID NO: 5 in combination with pomalinomide and dexamethasone for a time sufficient to treat AL.

The invention also provides for a method of treating light chain amyloidosis (AL), comprising administering to a patient in need thereof an anti-CD38 antibody comprising the HCDR1, the HCDR2 and the HCDR3 of SEQ ID NOs: 6, 7 and 8, respectively and the VH of SEQ ID NO: 4 and the VL of SEQ ID NO: 5 in combination with thalidomide for a time sufficient to treat AL.

The invention also provides for a method of treating light chain amyloidosis (AL), comprising administering to a patient in need thereof an anti-CD38 antibody comprising the VH of SEQ ID NO: 4 and the VL of SEQ ID NO: 5 in combination with thalidomide and a corticosteroid for a time sufficient to treat AL.

The invention also provides for a method of treating light chain amyloidosis (AL), comprising administering to a patient in need thereof an anti-CD38 antibody comprising the VH of SEQ ID NO: 4 and the VL of SEQ ID NO: 5 in combination with thalidomide and dexamethasone for a time sufficient to treat AL.

The invention also provides for a method of treating light chain amyloidosis (AL), comprising administering to a patient in need thereof an anti-CD38 antibody comprising the VH of SEQ ID NO: 4 and the VL of SEQ ID NO: 5 in combination with ixazomib for a time sufficient to treat AL.

In some embodiments, the patient is resistant to treatment with a proteasome inhibitor.

In some embodiments, the patient is resistant to treatment with cyclophosphamide.

In some embodiments, the patient is resistant to treatment with a corticosteroid.

In some embodiment, the patient is resistant to treatment with a proteasome inhibitor, cyclophosphamide and a corticosteroid.

In some embodiment, the patient is resistant to treatment with a Velcade® (bortezomib), cyclophosphamide and dexamethasone.

In some embodiments, the combination of the anti-CD38 antibody and the second therapeutic agent may be administered over any convenient timeframe. For example, the anti-CD38 antibody and the second therapeutic agent may be administered to a patient on the same day, and even in the same intravenous infusion. However, the anti-CD38 antibody and the second therapeutic agent may also be administered on alternating days or alternating weeks or months, and so on. In some embodiments, the anti-CD38 antibody and the second therapeutic agent may be administered with sufficient proximity in time that they are simultaneously present (e.g., in the serum) at detectable levels in the patient being treated. In some embodiments, an entire course of treatment with the anti-CD38 antibody consisting of a number of doses over a time period is followed or preceded by a course of treatment with the second therapeutic agent, consisting of a number of doses. A recovery period of 1, 2 or several days or weeks may be used between administration of the anti-CD38 antibody and the second therapeutic agent.

Anti-CD38 antibody or a combination of anti-CD38 antibody and the second therapeutic agent may be administered together with any form of radiation therapy including external beam radiation, intensity modulated radiation therapy (IMRT) and any form of radiosurgery including Gamma Knife, Cyberknife, Linac, and interstitial radiation (e.g. implanted radioactive seeds, GliaSite balloon), and/or with surgery.

While having described the invention in general terms, the embodiments of the invention will be further disclosed in the following examples that should not be construed as limiting the scope of the claims.

Further Embodiments of the Invention

Set out below are certain further embodiments of the invention according to the disclosures elsewhere herein. Features from embodiments of the invention set out above described as relating to the invention disclosed herein also relate to each and every one of these further numbered embodiments.

1. An anti-CD38 antibody that competes for binding to CD38 with an antibody comprising a heavy chain variable region (VH) of SEQ ID NO: 4 and a light chain variable region (VL) of SEQ ID NO: 5 for use in treating a patient having a CD38-positive hematological malignancy, wherein the patient is undergoing hematopoietic stem cell transplantation (HSCT).

2. The anti-CD38 antibody for use according to embodiment 1, wherein the CD38-positive hematological malignancy is
   a. light chain amyloidosis (AL), multiple myeloma (MM), acute lymphoblastic leukemia (ALL), non-Hodgkin's lymphoma (NHL), diffuse large B-cell lymphoma (DLBCL), Burkitt's lymphoma (BL), follicular lymphoma (FL) or mantle-cell lymphoma (MCL);
   b. a plasma cell disease;
   c. light chain amyloidosis (AL);
   d. multiple myeloma (MM); or
   e. Waldenstrom's macroglobulinemia.

3. The anti-CD38 antibody for use according to embodiment 2, wherein AL is cardiac stage I, cardiac stage II, cardiac stage III, relapsed or refractory.

4. The anti-CD38 antibody for use according to any one of embodiments 1-3, wherein the HSCT
   a. is allogeneic, autologous or syngeneic; or
   b. comprises transplantation of blood stem cells derived from bone marrow, blood or amniotic fluid.

5. The anti-CD38 antibody for use according to any one of embodiments 1-4, wherein the anti-CD38 antibody is administered prior to, during or after HSCT.

6. The anti-CD38 antibody for use according to any one of embodiments 1-5, wherein the patient has completed chemotherapy and/or radiation therapy prior to HSCT.

7. The anti-CD38 antibody for use according to any one of embodiments 1-6, wherein the anti-CD38 antibody binds to the region SKRNIQFSCKNIYR (SEQ ID NO: 2) and the region EKVQTLEAWVIHGG (SEQ ID NO: 3) of human CD38 (SEQ ID NO: 1).

8. The anti-CD38 antibody for use according to any one of embodiments 1-7, wherein the anti-CD38 antibody comprises the heavy chain complementarity determining regions (HCDR) 1, HCDR2 and HCDR3 sequences of SEQ ID NOs: 6, 7 and 8, respectively; and the light chain complementarity determining regions (LCDR) 1, LCDR2 and LCDR3 sequences of SEQ ID NOs: 9, 10 and 11, respectively.

9. The anti-CD38 antibody for use according to any one of embodiments 1-8, wherein the anti-CD38 antibody comprises the heavy chain variable region (VH) of SEQ ID NO: 4 and the light chain variable region (VL) of SEQ ID NO: 5.

10. The anti-CD38 antibody for use according to any one of embodiments 1-9, wherein the anti-CD38 antibody comprises a heavy chain comprising an amino acid sequence that is 95%, 96%, 97%, 98% or 99% identical to that of SEQ ID NO: 12 and a light chain comprising an amino acid sequence that is 95%, 96%, 97%, 98% or 99% identical to that of SEQ ID NO: 13.

11. The anti-CD38 antibody for use according to any one of embodiments 1-10, wherein the anti-CD38 antibody comprises the heavy chain comprises the heavy chain of SEQ ID NO: 12 and the light chain of SEQ ID NO: 13.

12. An anti-CD38 antibody that competes for binding to CD38 with an antibody comprising a heavy chain variable region (VH) of SEQ ID NO: 4 and a light chain variable region (VL) of SEQ ID NO: 5 for use in treating a patient having light chain amyloidosis.

13. The anti-CD38 antibody for use according to embodiment 12, wherein the patient is resistant to treatment with a proteasome inhibitor, cyclophosphamide and/or a corticosteroid.

14. The anti-CD38 antibody for use according to embodiment 13, wherein the proteasome inhibitor is Velcade® (bortezomib).

15. The anti-CD38 antibody for use according to any one of embodiments 13-14, wherein the corticosteroid is dexamethasone.

16. The anti-CD38 antibody for use according to any one of embodiments 12-15, wherein the anti-CD38 antibody is administered in combination with a second therapeutic agent.

17. The anti-CD38 antibody for use according to embodiment 16, wherein the second therapeutic agent is a proteasome inhibitor, cyclophosphamide or a corticosteroid.

18

18. The anti-CD38 antibody for use according to any one of embodiments 16-17, wherein the proteasome inhibitor is Velcade® (bortezomib) or NINLARO® (ixazomib).

19. The anti-CD38 antibody for use according to any one of embodiments 16-18, wherein the corticosteroid is dexamethasone.

20. The anti-CD38 antibody for use according to any one of embodiments 16-19, wherein the second therapeutic agent is Velcade® (bortezomib), NINLARO® (ixazomib), Kyprolis® (carfilzomib), Farydak® (panobinostat), cyclophosphamide, Alkeran® (melphalan), Thalomid® (thalidomide), Revlimid® (lenalidomide), Pomalyst® (pomalidomide), dexamethasone or interferon alpha.

21. The anti-CD38 antibody for use according to any one of embodiments 12-20, wherein the anti-CD38 antibody is administered in combination with a proteasome inhibitor, cyclophosphamide and a corticosteroid.

22. The anti-CD38 antibody for use according to embodiment 21, wherein the proteasome inhibitor is Velcade® (bortezomib).

23. The anti-CD38 antibody for use according to any one of embodiments 21-22, wherein the proteasome inhibitor is NINLARO® (ixazomib).

24. The anti-CD38 antibody for use according to any one of embodiments 21-23, wherein the corticosteroid is dexamethasone.

25. The anti-CD38 antibody for use according to any one of embodiments 21-24, wherein the proteasome inhibitor is Velcade® (bortezomib) and the corticosteroid is dexamethasone.

26. The anti-CD38 antibody for use according to any one of embodiments 21-25, wherein the proteasome inhibitor is NINLARO® (ixazomib) and the corticosteroid is dexamethasone.

27. The anti-CD38 antibody for use according to any one of embodiments 16-26, wherein the anti-CD38 antibody and the second therapeutic agent are administered simultaneously, sequentially or separately.

28. The anti-CD38 antibody for use according to any one of embodiments 16-27, wherein the anti-CD38 antibody and the second therapeutic agent are administered simultaneously, sequentially or separately.

29. The anti-CD38 antibody for use according to any one of embodiments 21-28, wherein the anti-CD38 antibody, proteasome inhibitor, cyclophosphamide and the corticosteroid are administered simultaneously, sequentially or separately.

30. The anti-CD38 antibody for use according to any one of embodiments 12-29, wherein AL is cardiac stage I, cardiac stage II, cardiac stage III, relapsed or refractory.

31. The anti-CD38 antibody for use according to any one of embodiments 12-30, wherein the patient is undergoing hematopoietic stem cell transplantation (HSCT).

32. The anti-CD38 antibody for use according to any one of embodiments 12-31, wherein the HSCT is allogeneic, autologous or syngeneic.

33. The anti-CD38 antibody for use according to any one of embodiments 12-32, wherein the HSCT comprises transplantation of blood stem cells derived from bone marrow, blood or amniotic fluid.

34. The anti-CD38 antibody for use according to any one of embodiments 12-33, wherein the anti-CD38 antibody is administered prior to, during or after HSCT.

35. The anti-CD38 antibody for use according to any one of embodiments 12-34, wherein the patient has completed chemotherapy and/or radiation therapy prior to HSCT.

36. The anti-CD38 antibody for use according to any one of embodiments 12-35, wherein the patient is further treated with radiotherapy.

37. The anti-CD38 antibody for use according to any one of embodiments 12-36, wherein the anti-CD38 antibody does not mediate killing of CD34-positive hematopoietic progenitor cells by complement dependent cytotoxicity (CDC).

38. The anti-CD38 antibody for use according to any one of embodiments 12-37, wherein the anti-CD38 antibody induces killing of CD38 positive plasma cells by antibody-dependent cell-mediated cytotoxicity (ADCC), antibody-dependent cellular phagocytosis (ADCP), complement dependent cytotoxicity (CDC), apoptosis, or modulation of CD38 enzymatic activity.

39. The anti-CD38 antibody for use according to any one of embodiments 12-38, wherein the anti-CD38 antibody competes for binding to CD38 with an antibody comprising a heavy chain variable region (VH) of SEQ ID NO: 4 and a light chain variable region (VL) of SEQ ID NO: 5.

40. The anti-CD38 antibody for use according to any one of embodiments 12-39, wherein the anti-CD38 antibody binds at least to the region SKRNIQFSCKNIYR (SEQ ID NO: 2) and the region EKVQTLEAWVIHGG (SEQ ID NO: 3) of human CD38 (SEQ ID NO: 1).

41. The anti-CD38 antibody for use according to any one of embodiments 12-40, wherein the anti-CD38 antibody comprises a heavy chain complementarity determining region 1 (HCDR1), a HCDR2 and a HCDR3 amino acid sequences of SEQ ID NOs: 6, 7 and 8, respectively, and a light chain complementarity determining region 1 (LCDR1), a LCDR2 and a LCDR3 amino acid sequences of SEQ ID NOs: 9, 10 and 11, respectively.

42. The anti-CD38 antibody for use according to any one of embodiments 12-41, wherein the anti-CD38 antibody comprises the VH comprising an amino acid sequence that is 95%, 96%, 97%, 98%, 99% or 100% identical to that of SEQ ID NO: 4 and the VL comprising an amino acid sequence that is 95%, 96%, 97%, 98%, 99% or 100% identical to that of SEQ ID NO: 5.

43. The anti-CD38 antibody for use according to any one of embodiments 12-42, wherein the anti-CD38 antibody comprises the VH of SEQ ID NO: 4 and the VL of SEQ ID NO: 5.

44. The anti-CD38 antibody for use according to any one of embodiments 12-43, wherein the anti-CD38 antibody comprises a heavy chain comprising an amino acid sequence that is 95%, 96%, 97%, 98%, 99% or 100% identical to that of SEQ ID NO: 12 and a light chain comprising an amino acid sequence that is 95%, 96%, 97%, 98%, 99% or 100% identical to that of SEQ ID NO: 13.

45. The anti-CD38 antibody for use according to any one of embodiments 12-44, wherein the anti-CD38 antibody comprises the heavy chain of SEQ ID NO: 12 and the light chain of SEQ ID NO: 13.

46. The anti-CD38 antibody for use according to any one of embodiments 12-46, wherein the anti-CD38 antibody comprises the HCDR1, the HCDR2, the HCDR3, the LCDR1, the LCDR2 and the LCDR3 of:
   a. the VH of SEQ ID NO: 14 and the VL of SEQ ID NO: 15;
   b. the VH of SEQ ID NO: 16 and the VL of SEQ ID NO: 17;
   c. the VH of SEQ ID NO: 18 and the VL of SEQ ID NO: 19; or
   d. the VH of SEQ ID NO: 20 and the VL of SEQ ID NO: 21, wherein the HCDR1, the HCDR2, the HCDR3, the LCDR1, the LCDR2 and the LCDR3 are defined by Kabat, Chothia, or IMGT.

47. The anti-CD38 antibody for use according to embodiment 46, wherein the anti-CD38 antibody comprises
   e. the VH of SEQ ID NO: 14 and the VL of SEQ ID NO: 15;
   f. the VH of SEQ ID NO: 16 and the VL of SEQ ID NO: 17;
   g. the VH of SEQ ID NO: 18 and the VL of SEQ ID NO: 19; or
   h. the VH of SEQ ID NO: 20 and the VL of SEQ ID NO: 21.

48. The anti-CD38 antibody for use according to any one of embodiments 12-47, wherein the anti-CD38 antibody is humanized or human.

49. The anti-CD38 antibody for use according to any one of embodiments 12-48, wherein the anti-CD38 antibody is of IgG1, IgG2, IgG3 or IgG4 isotype.

50. The anti-CD38 antibody for use according to any one of embodiments 12-49, wherein the anti-CD38 antibody is of IgG1 isotype.

51. The anti-CD38 antibody for use according to any one of embodiments 12-50, wherein the anti-CD38 antibody is administered intravenously.

52. The anti-CD38 antibody for use according to any one of embodiments 12-51, wherein the anti-CD38 antibody is administered subcutaneously in a pharmaceutical composition comprising the anti-CD38 antibody and a hyaluronidase.

53. The anti-CD38 antibody for use according to embodiment 42, wherein the hyaluronidase is rHuPH20 of SEQ ID NO: 22.

Example 1

Materials and Methods

Mobilized blood stem and progenitor cells from MM and AL patients undergoing blood stem cell mobilization and collection on an IRB approved clinical study (Tufts Medical Center IRB #10680 *Pre-Clinical Studies of DARZALEX™ (daratumumab) in Stem-Cell Mobilization and Transplant for Patients with Clonal Plasma cell Disease*s) requiring written informed consent were used to study the effects of DARZALEX™ (daratumumab) on $CD34^+$ cell growth in vitro. Both unselected and CD34-selected mobilized blood progenitor cells from patients with MM and AL were used. The effects of DARZALEX™ (daratumumab) or an isotype control antibody was assessed on in vitro progenitor cell colony growth in semisolid assays as an indicator of DARZALEX™ (daratumumab)'s impact on the proliferation of $CD34^+$ human hematopoietic progenitor cells.

Methylcellulose progenitor cell assays containing recombinant cytokines (Stem Cell Technologies, Vancouver, CA; Cat #04435) were performed according to manufacturer's instructions with unselected and CD34-selected mobilized blood stem cells from the day 1 leukapheresis product at several concentrations. CD34 selection was performed with the Miltenyi MiniMacs device. CD34-unselected cells were used at a concentration of $0.5 \times 10^4$/ml and CD34-selected cells at 500 cells/ml. Assays were performed with DARZALEX™ (daratumumab) or control antibody at varying concentrations; in some assays, cells were plated in media containing DARZALEX™ (daratumumab) or control antibody, while in other assays cells were plated after incubating at 37° C. in 5% $CO_2$ for one hour in complement-rich human serum with DARZALEX™ (daratumumab) or control antibody. Colonies were counted on day 14 (CFU-GM, BFU-E, CFU-Mix).

Example 2

CD38 is Expressed on Clonal AL Plasma Cells

The clonal plasma cells of patients with AL express high levels of mRNA for CD38 based on transcriptional profiles of FACS-sorted $CD138^+$ bone marrow plasma cells (n=16, GEO GSE24128; Zhou et al., Clin Lymphoma Myeloma Leuk 12:49-58, 2012) obtained at diagnosis prior to therapy (FIG. 1). In addition, in an analysis of the immunophenotype of the $CD138^+$ bone marrow plasma cells from newly diagnosed AL patients, CD38 was uniformly found on the cell surface in all cases (Paiva et al., Blood 117:3613-6, 2011).

Example 3

NK Cells from Patients with AL are Functional and Induce DARZALEX™ (Daratumumab)-Mediated ADCC Against CD38-Expressing Cells Three Weeks After Stem Cell Transplant (SCT)

With an IRB approved investigational protocol described in Example 1, requiring written informed consent, NK cells (CD3−/CD56+/CD16+) obtained three weeks post-SCT from AL patients were evaluated, assessing the percentage and number of NK cells in the peripheral blood specimens and the in vitro activity of these NK cell effectors with DARZALEX™ (daratumumab) in ADCC assays with human plasma cells (MM1S cells) as targets. MM1S cells express high levels of CD38, making them suitable targets for DARA. Flow cytometry was performed employing the FlowCellect™ Human Natural Killer Cell Characterization Kit (Millipore, Billerica, MA; catalogue #FCIM025164). The bioluminescent cytotoxicity assays (Cell Technology; Mountain View, CA) were performed following manufacturer's instructions. Target cell concentration was optimized at 5000 MM1S cells per well. Target cells were incubated with DARZALEX™ (daratumumab) or control antibody (human IgG1 kappa, Sigma-Aldrich, St Louis MO) at 100 ng/mL for 15 minutes in a 37° C. 5% $CO_2$ incubator. Then, they were added to wells containing patient NK cells at 10:1 effector:target cell concentration. The number of NK cells in each sample was calculated based upon the flow cytometry characterization of the fresh patient specimens. The ADCC was determined by calculating luminescent values for each reaction condition as per manufacturer's instructions using standard controls. The amount of lysis per situation (% ADCC) was determined by the following calculation:

% ADCC=(Sample)−(Control 1)−(Control 2)×100 (Control 3)−(Control 1)

Sample: sample with DARZALEX™ (daratumumab)
Control 1: assay with isotype control (Target spontaneous release)
Control 2: no antibody, no effector cells
Control 3: maximum lysis in the presence of lysis reagent The amount of DARZALEX™ (daratumumab) specific lysis was calculated by subtracting the % ADCC with isotype control from the % ADCC with DARZALEX™ (daratumumab).

Figure 2:
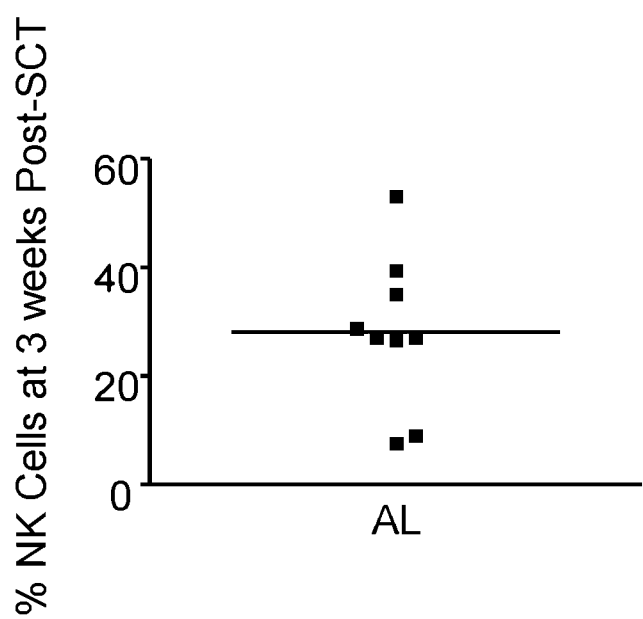
FIG. 2 shows the percentage (%) of NK cells of the mononuclear cells in the peripheral blood of AL patients at 3 weeks after stem cell transplant (SCT).

As shown in FIG. 2, NK cells were almost one third of all mononuclear cells in the peripheral blood of AL patients (n=9) at 3 weeks after SCT. In the bioluminescent ADCC assays, NK cells from patients with AL (n=6) combined with DARZALEX™ (daratumumab) had a median specific lysis of 32% (range, −3 to 73%).

Example 4

Figure 3:
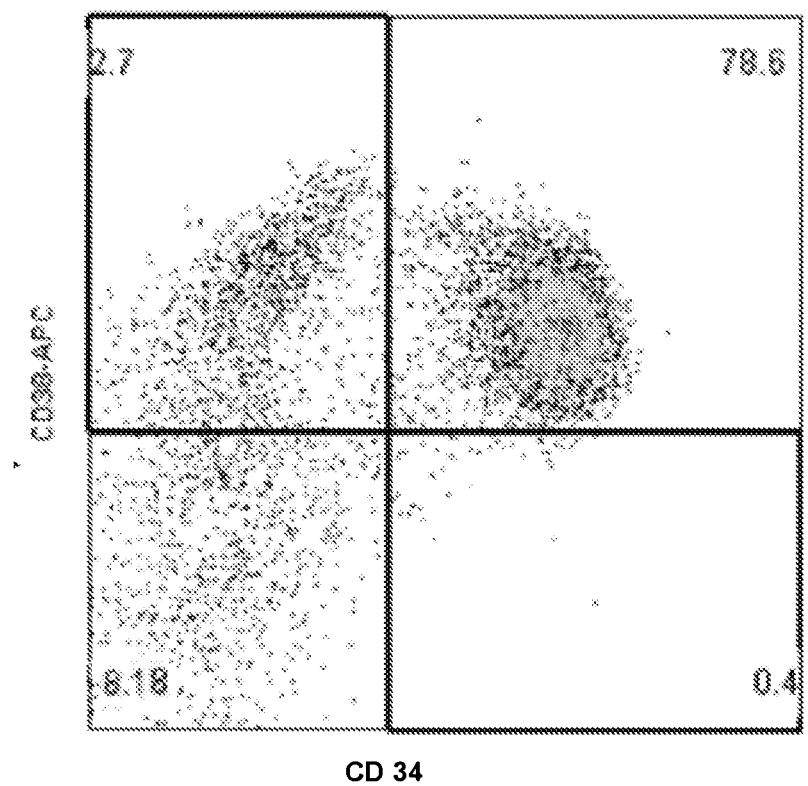
FIG. 3 shows that CD38 is expressed on $CD34^+$ hematopoietic progenitor cells.

DARZALEX™ (Daratumumab) Does Not Induce CD34+ Hematopoietic Progenitor Cell Killing Even Though High CD38 Expression is Found on These Cells CD38 expression on CD34+ cells was analyzed using flow cytometry using APC-conjugated anti-human CD38 (HIT2, Biolegend, San Diego CA). The CD34+ cells had the appearance of myeloblasts, and expressed high levels of CD38 (FIG. 3).

The effects of DARZALEX™ (daratumumab) on CD34+ cell growth in vitro was studied using mobilized blood stem and progenitor cells from MM and AL patients undergoing blood stem cell mobilization and collection on an IRB approved clinical study requiring informed consent as described in Example 1. Both unselected and CD34-selected mobilized blood progenitor cells from patients with MM and AL were used, and the effects of daratumumab or an isotype control antibody on in vitro progenitor cell colony growth in semisolid assays was assessed as an indicator of DARZA-LEX™ (daratumumab)'s impact on the proliferation of CD34+ human hematopoietic progenitor cells.

Methylcellulose progenitor cell assays containing recombinant cytokines (Stem Cell Technologies, Vancouver, CA; Cat #04435) were performed according to manufacturer's instructions with unselected or CD34-selected mobilized blood stem cells from the day 1 leukapheresis product at several concentrations. CD34 selection was performed with the Miltenyi MiniMacs device. CD34-unselected cells were used at a concentration of $0.5 \times 10^4$/ml and CD34-selected cells at 500 cells/ml. Assays were performed with DARZA-LEX™ (daratumumab) or control antibody at varying concentrations; in some assays, cells were plated in media containing DARZALEX™ (daratumumab) or control antibody, while in other assays cells were plated after incubating at 37° C. in 5% $CO_2$ for one hour in complement-rich human serum with DARZALEX™ (daratumumab) or control antibody. Colonies were counted on day 14 (CFU-GM, BFU-E, CFU-Mix).

Figure 4A:
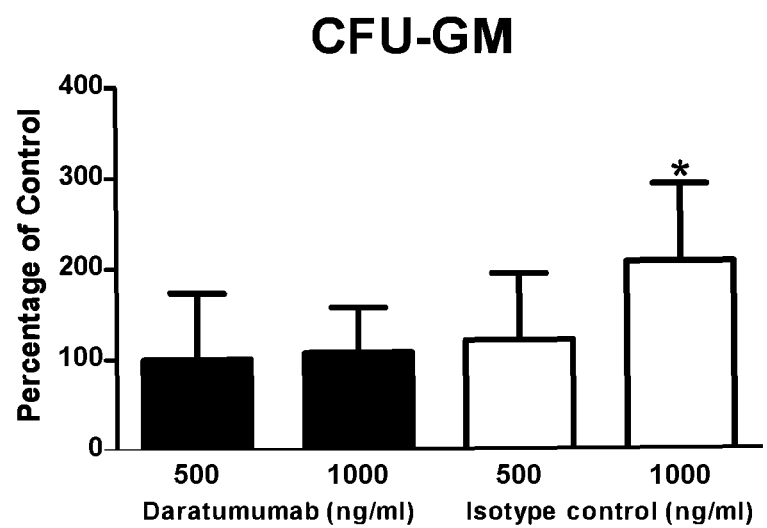
FIG. 4A shows that DARZALEX™ (daratumumab) has no effect on proliferation of thawed cryopreserved unselected mobilized blood progenitor cells, assessed by the ability of the progenitor cells to form similar numbers of colonies in the presence of 500 ng or 1000 ng/ml DARZALEX™ (daratumumab) when compared to isotype control. In this assay, colony forming unit granulocyte-macrophage (CFU-GM) was assessed after 14 days of culture in methylcellulose in the presence of DARZALEX™ (daratumumab), isotype control or no antibody control, and % colonies formed was plotted as a function of no antibody control. *p<0.05, paired t test. All assays were done in triplicates and 3 independent experiments were performed with progenitor cell specimens from 3 different patients. Data shows mean+/−SD.
Figure 4B:
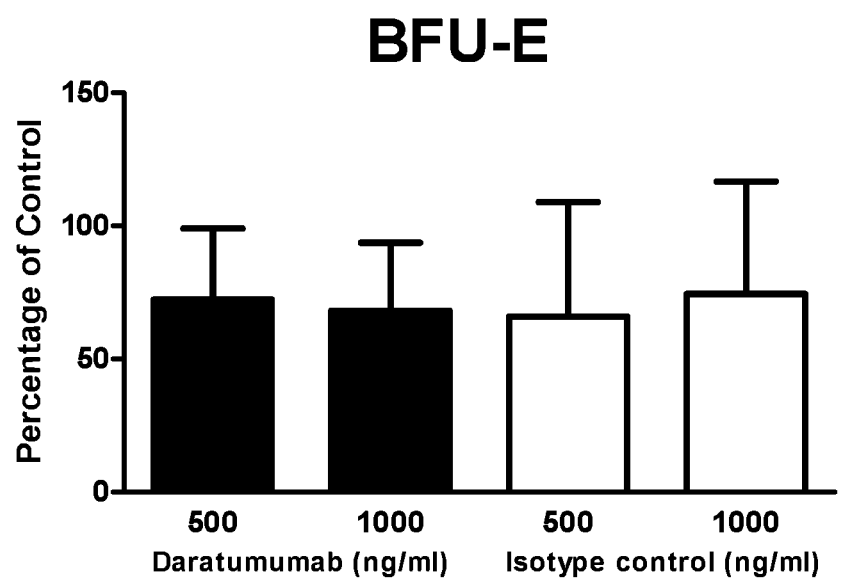
FIG. 4B shows that DARZALEX™ (daratumumab) has no effect on proliferation of thawed cryopreserved unselected mobilized blood progenitor cells, assessed by the ability of the progenitor cells to form similar numbers colonies in the presence of 500 ng or 1000 ng/ml DARZALEX™ (daratumumab) when compared to the isotype control. In this assay, blast forming unit erythroid (BFU-E) was assessed after 14 day growth in methylcellulose in the presence of DARZALEX™ (daratumumab), isotype control or no antibody control, and % colonies formed was plotted as a function of no antibody control. All assays were done in triplicates and 3 independent experiments were performed with progenitor cell specimens from 3 different patients. Data shows mean+/−SD.

Thawed cryopreserved unselected mobilized blood progenitor cells grew similar numbers of CFU-GM (FIG. 4A) and BFU-E (FIG. 4B) in cultures with DARZALEX™ (daratumumab) or isotype control (500 or 1000 ng/ml, compared to no antibody control. In these experiments, thawed unselected mobilized human blood progenitor cells were plated at a concentration of $5 \times 10^4$ cells per ml of semisolid medium (methylcellulose) in the presence of DARZALEX™ (daratumumab) or isotype control at 500 ng/ml or 1000 ng/ml. CFU-GM and GFU-E were counted two weeks later as percentage CFU-GM when compared to no antibody control. Of note, in the plates with 1000 ng/ml of isotype control antibody there was significantly more CFU-GM for unclear reasons.

Figure 5A:
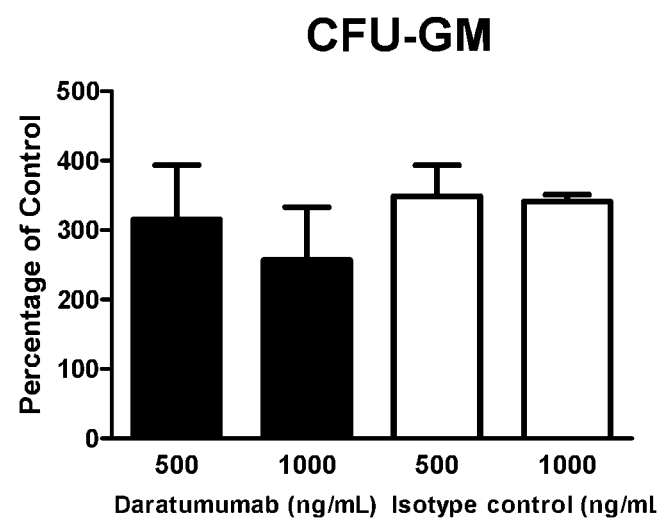
FIG. 5A shows that DARZALEX™ (daratumumab) has no effect on proliferation of fresh unselected mobilized blood progenitor cells assessed by their ability to form similar numbers of colonies in methylcellulose in the presence of 500 ng or 1000 ng/ml DARZALEX™ (daratumumab) when compared to isotype control. Colony formation was measured at day 14 as CFU-GM and % colonies formed was plotted as a function of no antibody control. All assays were done in triplicates and 3 independent experiments were performed with progenitor cell specimens from 3 different patients. Data shows mean+/−SD.
Figure 5B:
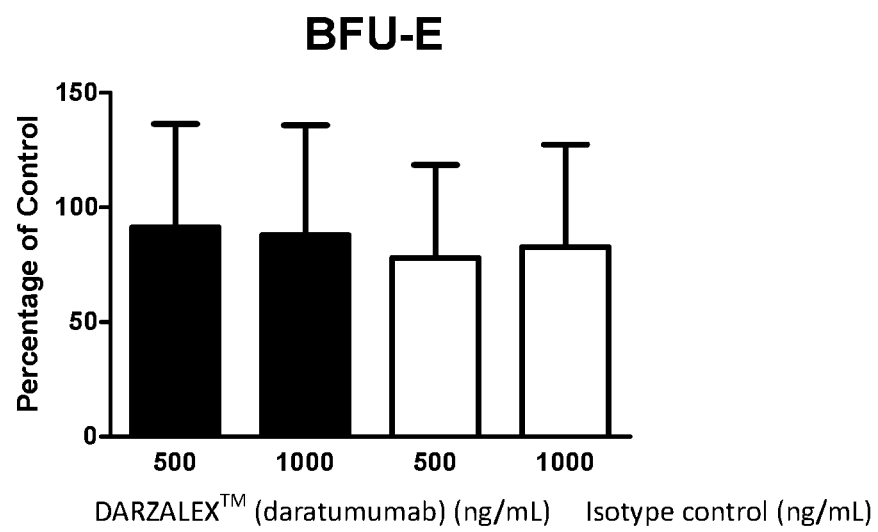
FIG. 5B shows that DARZALEX™ (daratumumab) has no effect on proliferation of fresh unselected mobilized blood progenitor cells assessed by their ability to form similar numbers of colonies in methylcellulose in the presence of 500 ng or 1000 ng/ml DARZALEX™ (daratumumab) when compared to isotype control. Colony formation was measured at day 14 as BFU-E and % colonies formed was plotted as a function of no antibody control. All assays were done in triplicates and 3 independent experiments were performed with progenitor cell specimens from 3 different patients. Data shows mean+/−SD.

Effect of DARZALEX™ (daratumumab) on fresh unselected mobilized blood progenitor cells was also assessed. DARZALEX™ (daratumumab) did not reduce CFU-GM (FIG. 5A) or BFU-E (FIG. 5B). Both DARZALEX™ (daratumumab) and the isotype control had increased CFU-GM formation at similar levels when compared to the no antibody control.

Ability of DARZALEX™ (daratumumab) to induce CDC on fresh CD34-selected hematopoietic progenitor cells was assessed. The CD34+ cells were incubated in 10% complement-rich human serum with no antibody, 500 ng/ml DARZALEX™ (daratumumab) or 500 ng/ml isotype control for 1 hour and then plated directly in semisolid medium. Colony formation was assessed per 500 CD34-selected cells. DARZALEX™ (daratumumab) did not reduce either CFU-GM (FIG. 6A) or BFU-E (FIG. 6B), indicating that the antibody did not induce CDC on the initial CD34-selected progenitor cells, despite the expression of CD38 on these cells. For unclear reason, there were more BFU-E in DARZALEX™ (daratumumab) treated samples. DARZA-LEX™ (daratumumab) increased the number of BFU-E formed.

Figure 6A:
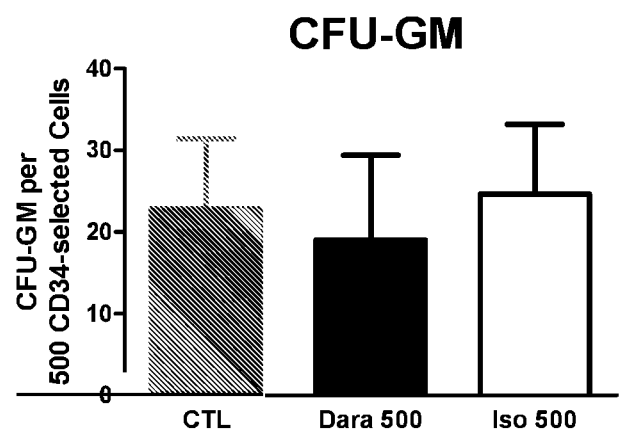
FIG. 6A shows that DARZALEX™ (daratumumab) does not kill CD34-selected hematopoietic progenitor cells by CDC despite high CD38 expression on the cells. $CD34^+$ cells were incubated 1 hour with serum with high complement with no antibody (CTL), 500 ng/ml DARZALEX™ (daratumumab) (Dara) or 500 ng/ml isotype control (Iso), after which cells were plated on semisolid media. Colony formation was measured at day 14 as CFU-GM per 500 CD34-selected cells. The results are from triplicate assays with cells from 1 patient with MM and 2 patients with AL.
Figure 6B:
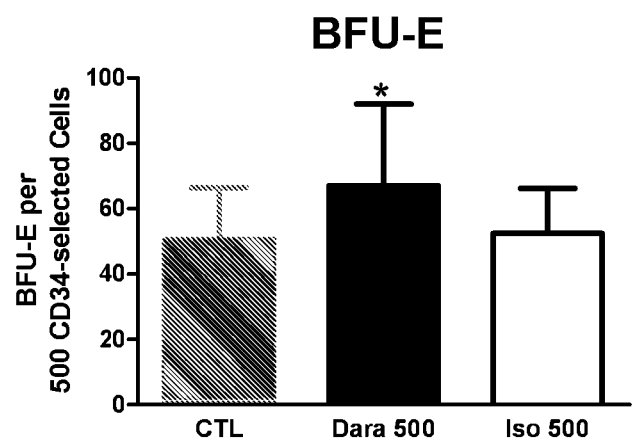
FIG. 6B shows that DARZALEX™ (daratumumab) does not kill CD34-selected hematopoietic progenitor cells by CDC despite high CD38 expression on the cells. $CD34^+$ cells were incubated 1 hour with serum with high complement, no antibody (CTL), 500 ng/ml DARZALEX™ (daratumumab) (Dara) or 500 ng/ml isotype control (Iso), after which cells were plated on semisolid media. Colony formation was measured at day 14 as BFU-E per 500 CD34-selected cells. There were more BFU-E in plates with DARZALEX™ (daratumumab) that reached statistical significance. The results are from triplicate assays with cells from 1 patient with MM and 2 patients with AL. (*p<0.01).
Figure 7A:
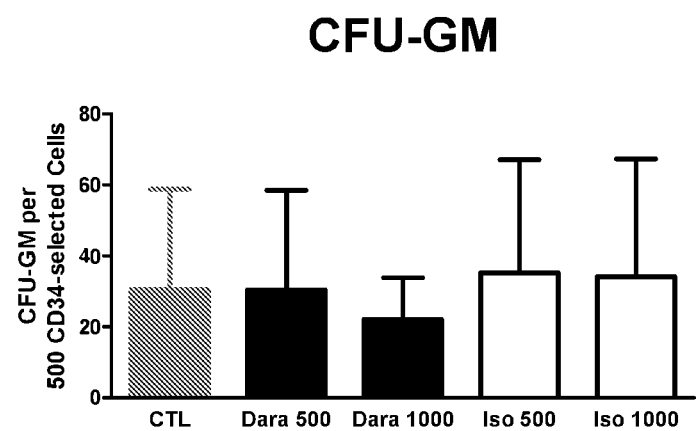
FIG. 7A shows that DARZALEX™ (daratumumab) has no adverse effect on fresh CD34-selected granulcytic-monocytic progenitor cells. Isolated $CD34^+$ cells were incubated in medium containing no antibody (CTL; control), DARZALEX™ (daratumumab) (Dara) or isotype control (Iso) at 500 ng/ml or 1000 ng/ml as indicated. Cells were placed in methylcellulose and colony formation was measured as CFU-GM per 500 CD34-selected cells at day 14. The results are from triplicate assays with cells from 1 patient with MM and 2 patients with AL.
Figure 7B:
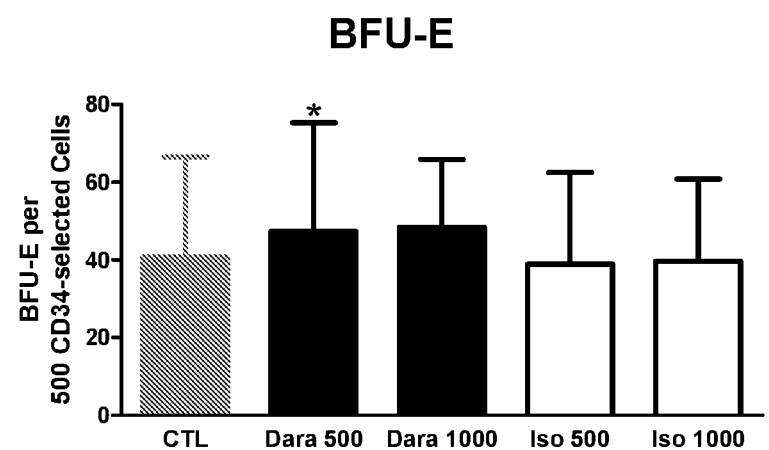
FIG. 7B shows that DARZALEX™ (daratumumab) has no adverse effect on fresh CD34-selected erythroid progenitor cells. Isolated CD34-cells were incubated in medium containing no antibody (CTL; control), daratumumab or isotype control (Iso) at 500 ng/ml or 1000 ng/ml. Cells were placed in methylcellulose and colony formation was measured as BFU-E per 500 CD34-selected cells at day 14. The results are from triplicate assays with cells from 2 patients with MM and 1 patient with AL. *p<0.02.

DARZALEX™ (daratumumab)'s effect on fresh CD34-selected hematopoietic progenitor cells was also tested by plating the cells directly into methylcellulose containing 500 ng/mL or 1000 ng/mL DARZALEX™ (daratumumab) or isotype control, or no antibody. Colony formation was assessed at day 14 for CFU-GM per 500 CD34-selected cells (FIG. 7A) or BFU-E per 500 CD34-selected cells (FIG. 7B). There was no decrease in colony formation with any concentration of DARZALEX™ (daratumumab), indicating that DARZALEX™ (daratumumab) was not toxic to CD34+ cell colony formation in this assay system. The results in FIGS. 6A, 6B and 7A show results from the mobilized blood progenitor cells of 1 patient with MM and 2 patients with AL. The results in FIG. 7B show results from the mobilized blood progenitor cells of 2 patients with MM and one patient with AL. Assays for BFU-E in the presence of 500 ng/ml DARZALEX™ (daratumumab) for unclear reasons contained significantly more BFU-E.

Example 5

DARZALEX™ (Daratumumab)-Mediated ADCC by Patient NK Cells is Dependent on FcγRIIIA Genotype Genomic DNA from patient cells was employed in PCR-based analysis using previously described methods and primers (Hatjiharissi et al., Blood 110:2561-2564, 2007) Amplicons were sequenced and analyzed for FcγRIIIA-158 polymorphisms. DARZALEX™ (daratumumab)-specific lysis in ADCC assays of patients with FcγRIIIA-158aa alleles encoding V/F and V/V was compared to F/F homozygotes.

Figure 8:
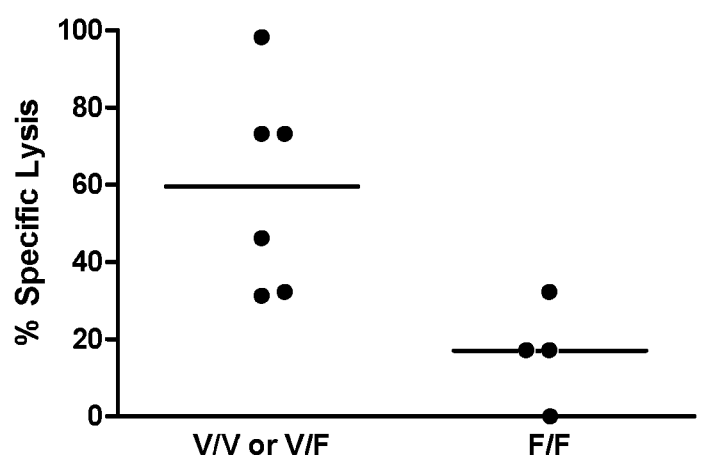
FIG. 8 shows that DARZALEX™ (daratumumab)-mediated ADCC was influenced by FCγRIIIa-158aa polymorphisms. Patients with 158V/V (V/V) and 158F/V (F/V) genotypes demonstrated an increased response rate when compared to the patients with 158F/F (F/F) genotype (vertical line is median for each group, P<0.05, Mann Whitney, two-tailed).

The PCR based-analysis showed that from ten patients analyzed in this study, six patients had V/F or V/V polymorphism and had a median 60% lytic activity (31-98) while 4 had F/F alleles and a median 17% lysis (0-32) (FIG. 8; P<0.05, Mann Whitney, two-tailed).

The initial correlation of Fc-receptor polymorphisms and DARZALEX™ (daratumumab) ADCC may be examined in future clinical trials.

Example 6

A Randomized Phase 3 Study to Evaluate the Efficacy and Safety of DARZALEX™ (Daratumumab) in Combination With Cyclophosphamide, Bortezomib and Dexamethasone (CyBorD) Compared to CyBorD Alone in Newly Diagnosed Systemic AL Amyloidosis A Phase 3, two-cohort, open-label study, comparing DARZALEX™ (daratumumab) in combination with CyBorD (Cyclophosphamide, Bortezomib, and Dexamethasone) to CyBorD alone in subjects with newly diagnosed AL Amyloidosis is conducted.

There are no currently approved medications for AL amyloidosis. In the absence of an approved treatment, medications developed for multiple myeloma are prescribed for the treatment. Combination of CyBorD is the most frequently used initial treatment for AL amyloidosis across EU and US (Venner et al., Blood 119:4387-4390, 2012; Mikhael et al., Blood 119: 4391-4394, 2012; Jaggard et al., Hematologica 99: 1479-1485, 2014; Palladini et al., Blood 126:612-615, 2015).

Primary Objective

The primary objective is to evaluate the complete hematologic response following treatment with DARZALEX™ (daratumumab) in combination with CyBorD compared to CyBorD alone in AL patients.

Secondary Objectives

To evaluate PFS based on all-cause mortality and progression disease (PD, including hematologic PD and organ PD according to consensus guidelines)
To evaluate the organ response rate (OrRR) (Comenzo 2012)
  Kidney
  Heart
  Liver
To evaluate hematologic response rate (ORR) and hematologic VGPR or better (i.e., CR+VGPR) rate.
To evaluate organ progression rate for the heart, kidneys, liver.
To evaluate duration of and time to hematologic CR and VGPR or better, respectively.
To evaluate duration of and time to organ response
To assess the safety and tolerability of DARZALEX™ (daratumumab) when administered in combination with CyBorD.
To assess DARZALEX™ (daratumumab) pharmacokinetics
To assess the immunogenicity of DARZALEX™ (daratumumab)
To evaluate treatment effects on patient-reported outcomes (PROs) including the SF-36 Health questionnaire, EuroQol-5 Dimensions (EQ-5D-5L) and European Organization for Research and Treatment of Cancer (EORTC) QLQ-C30.

Exploratory Objectives

To evaluate biomarkers of response including High Sensitivity (HS) Troponin T
To explore biomarkers predictive of response or resistance to therapy
To explore minimal residual disease status in amyloidosis patients Endpoints Primary Endpoint The primary endpoint is complete hematological response rate.

Secondary Endpoints

The secondary efficacy endpoints include:
Progression-free survival (PFS) based on all-cause mortality
Organ response rate (OrRR) for kidney, heart, liver
Overall survival (OS)
Time to next treatment (TNT)
Time to disease progression (TTP)
Time to hematologic disease progression
Overall Hematologic response
Hematologic VGPR or better rate
Time to complete hematologic response (or VGPR or better)
Duration of complete hematologic response (or VGPR or better)
Time to organ response
Duration of organ response
To evaluate treatment effects on patient reported outcomes including the EORTC QLQ-C30, Short Form-36 Health Survey [SF-36] and European Quality of Life Five Dimensions Questionnaire [EQ-5D-5L]).

Exploratory Endpoint

The exploratory endpoint is to evaluate minimal residual disease status in patients who achieve complete hematologic response in bone marrow and blood Hypothesis The primary hypothesis of this study is that is that DARZALEX™ (daratumumab) in combination with CyBorD will improve the complete hematological response rate compared to CyBorD alone, in subjects with newly diagnosed AL amyloidosis.

Study Design

This is a multicenter, Phase 3, two-cohort, open-label study, comparing DARZALEX™ (daratumumab) in combination with CyBorD to CyBorD alone in subjects with newly diagnosed AL. Approximately 360 subjects are randomized in two cohorts to initially receive either CyBorD or CyBorD in combination with DARZALEX™ (daratumumab) stratified by cardiac risk (Stage I, II, and Ma). Each cycle is 4 weeks. DARZALEX™ (daratumumab) is administered at 16 mg/kg weekly for the first 2 cycles (8 weeks) of treatment, followed by every 2 weeks for 4 cycles (16 weeks) and then every 4 weeks until a maximum of 6 cycles of therapy (24 weeks) with the CyBorD backbone (both cohorts). Subjects randomized to the DARZALEX™ (daratumumab) group may continue DARZALEX™ (daratumumab) every 4 weeks after 6 cycles until disease progression for a maximum of 2 years. Subjects receive weekly cyclophosphamide 300 mg/m² either po or IV, bortezomib 1.3 mg/m² SQ, and dexamethasone 40 mg per week. Cycles are repeated every 4 weeks. A maximum number of 6 cycles are given.

Prior to randomization, a safety run-in is conducted in 6 subjects treated with DARZALEX™ (daratumumab) plus CyBorD for at least 1 cycle to establish safety of the combination regimen. Dosing of these 6 subjects is staggered such that subjects receive the first dose no sooner than 48 hours apart from the previously enrolled subject. Safety evaluation is performed by the sponsor and external experts after at least 1 cycle is completed for 6 subjects prior to the start of the randomized portion of the protocol. Subjects in the safety run-in continue all scheduled assessments as specified in the T&E, and contribute to the overall safety evaluation of DARZALEX™ (daratumumab)+CyBorD regimen. However, these subjects are not included in the overall efficacy assessment.

Subject Selection

Inclusion Criteria

1. Subject must be at least 18 years of age.
2. Histopathological diagnosis of amyloidosis or light chain deposition disease based on detection by polarizing microscopy of green bi-refringent material in Congo Red stained tissue specimens or characteristic electron microscopy appearance
3. Measurable disease of amyloid light chain amyloidosis as defined by at least ONE of the following: serum monoclonal protein >=0.5 g/dL by protein electrophoresis, >200 mg of monoclonal protein in the urine on 24 hour electrophoresis, serum free light-chain >=5.0 mg/dL with an abnormal kappa:lambda ratio or the difference between involved and uninvolved free light chains (dFLC)≥5 mg/dL
4. Patient must have newly diagnosed AL Amyloidosis without prior systemic therapy. The only exception is that subjects may have up to 4 weeks of therapy with bortezomib, cyclophosphamide and/or dexamethasone (or equivalent steroid) prior to randomization on an emergency basis if the subject requires urgent therapy.
5. Eastern Cooperative Oncology Group (ECOG) Performance Status (PS) 0, 1 or 2
6. Subject must have pre-treatment clinical laboratory values meeting the following criteria during the Screening Phase:
   i) Absolute neutrophil count ≥1.0×10⁹/L;
   ii) Hemoglobin level ≥7.5 g/dL (≥5 mmol/L); (Blood transfusions to maintain Hb≥7.5 is acceptable)
   iii) Platelet count >50×10⁹/L; Platelet transfusions are acceptable
   iv) Alanine aminotransferase level (ALT)≤2.5 times the upper limit of normal (ULN);
   v) Aspartate Aminotransferase (AST)≤2.5 times the upper limit of normal (ULN)
   vi) Total bilirubin level≤1.5×ULN, (except for Gilbert Syndrome: direct bilirubin <2×ULN);
   vii) Creatinine clearance ≥=20 mL/min; Please note that the creatinine clearance can be either measured by 24 hour Urine study, or estimated using a validated equation, such as a the MDRD, CKD-epi, or Cockcroft Gault (see attachment 3 for details)
   viii) TSH and free T4 within normal limits. Patients may receive thyroid hormone therapy if needed to correct underlying hypothyroidism
7. Women of childbearing potential must be practicing a highly effective method of birth control 4 weeks prior to initiating treatment, during therapy, during the dose interruptions, and continuing for 4 weeks following discontinuation of study drugs. The birth control is consistent with local regulations regarding the use of birth control methods for subjects participating in clinical studies: e.g., established use of oral, injected or implanted hormonal methods of contraception; placement of an intrauterine device or intrauterine system; barrier methods: condom with spermicidal foam/gel/film/cream/suppository or occlusive cap (diaphragm or cervical/vault caps) with spermicidal foam/gel/film/cream/suppository (if hormonal or IUD contraception is medically contraindicated, 2 or other effective or highly effective methods may be used); male partner sterilization (the vasectomized partner should be the sole partner for that subject); true abstinence (when this is in line with the preferred and usual lifestyle of the subject) during and after the study (3 months after the last dose of DARZALEX™ (daratumumab) for women).
8. A man who is sexually active with a woman of childbearing potential and has not had a vasectomy must agree to use a barrier method of birth control, e.g. either condom with spermicidal foam/gel/film/cream/suppository or partner with occlusive cap (diaphragm or cervical/vault caps) with spermicidal foam/gel/film/cream/suppository. All men must also not donate sperm during the study and for 3 months after receiving the last dose of study drug.
9. A woman of childbearing potential must have 2 negative serum or urine pregnancy tests at Screening, first within 10 to 14 days prior to dosing and the second within 24 hours prior to dosing.
10. Each subject must sign an informed consent form (ICF) indicating that he or she understands the purpose of and procedures required for the study and are willing to participate in the study. Subjects must be willing and able to adhere to the prohibitions and restrictions specified in this protocol, as referenced in the ICF.

Exclusion Criteria

1. Prior therapy for AL Amyloidosis or Multiple myeloma with the exception of a single cycle (maximum 4 weeks) of bortezomib, cyclophosphamide and/or dexamethasone (or equivalent steroid) prior to randomization
2. Previous or current diagnosis of symptomatic multiple myeloma defined by CRAB criteria, including the presence of lytic bone disease, plasmacytomas, and/or hypercalcemia.
3. Evidence of significant cardiovascular conditions as specified below:
   a) NT-ProBNP>8500 ng/L
   b) New York Heart Association (NYHA) classification IIIB or IV heart failure
   c) Unstable angina or myocardial infarction within 6 months prior to first dose
   d) Grade 2 or 3 atrioventricular (AV) block or sick sinus syndrome, unless subject has a pacemaker (Mobitz type I AV block of any grade is permitted)

e) Known history of sustained (>30 second) ventricular tachycardia or cardiac syncope. Known history of recurrent non-sustained ventricular tachycardia (>3 beats) despite anti-arrhythmic therapy f) Screening 12-lead ECG showing a baseline QT interval as corrected (QTcF)>470 msec.

g) Supine systolic blood pressure <90 mm Hg, or symptomatic orthostatic hypotension, or a decrease in systolic blood pressure upon standing of >20 mm Hg despite medical management (e.g. midodrine, fludrocortisones)

h) Left Ventricular Ejection Fraction (LVEF) by transthoracic echocardiogram, MUGA scan, cardiac MRI or cardiac catheterization <40%. Assessment required during screening.

4. Subjects planning to undergo a stem cell transplant during first six cycles of protocol therapy are excluded. Stem cell collection during the first six cycles of protocol therapy is permitted.

5. Diagnosed or treated for malignancy other than AL, except:
   a) Malignancy treated with curative intent and with no known active disease present for ≥5 years before randomization
   b) Adequately treated non-melanoma skin cancer or lentigo maligna without evidence of disease
   c) Adequately treated carcinoma in situ (e.g. cervical, breast) with no evidence of disease 6. Subject has known chronic obstructive pulmonary disease (COPD) with a Forced Expiratory Volume in 1 second (FEV1)<50% of predicted normal. Note that FEV1 testing is required for patients suspected of having COPD and subjects must be excluded if FEV1<50% of predicted normal.

7. Subject has known moderate or severe persistent asthma within the past 2 years (see Attachment 5), or currently has uncontrolled asthma of any classification. (Note that subjects who currently have controlled intermittent asthma or controlled mild persistent asthma are allowed in the study).

8. Subject is known to be seropositive for human immunodeficiency virus (HIV), known to have hepatitis B surface antigen positivity, or known to have a history of hepatitis C.

9. Grade 3 sensory or grade 1 painful peripheral neuropathy

10. Known hypersensitivity to bortezomib, boron or mannitol

11. Subject has any concurrent medical condition or disease (e.g., active systemic infection) that is likely to interfere with study procedures or results, or that in the opinion of the investigator would constitute a hazard for participating in this study.

12. Any form of secondary or familial (ATTR) amyloidosis

13. Subject has known allergies, hypersensitivity, or intolerance to monoclonal antibodies or human proteins, or their excipients (refer to Investigator Brochure), or known sensitivity to mammalian-derived products.

14. Subject is known or suspected of not being able to comply with the study protocol (e.g., because of alcoholism, drug dependency, or psychological disorder) or the subject has any condition for which, in the opinion of the investigator, participation would not be in the best interest of the subject (e.g., compromise their well-being) or that could prevent, limit, or confound the protocol-specified assessments.

15. Subject is a woman who is pregnant or breast-feeding or planning to become pregnant while enrolled in this study or within 6 months after the last dose of study drug.

16. Subject has received an investigational drug (including investigational vaccines) or used an invasive investigational medical device within 4 weeks before Cycle 1, Day 1 (except for investigational anti-myeloma agents, which cannot be taken within 2 weeks prior to Cycle 1, Day 1, as described in exclusion #3).

17. Subject has had major surgery within 2 weeks before Cycle 1, Day 1, or will not have fully recovered from surgery, or has surgery planned during the time the subject is expected to participate in the study or within 2 weeks after the last dose of study drug administration. Note: subjects with planned surgical procedures to be conducted under local anesthesia may participate.

Safety Evaluations

Safety will be measured by adverse events, laboratory test results, ECGs, vital sign measurements, physical examination findings, and ECOG performance status. Any clinically relevant changes occurring during the study will be recorded on the Adverse Event section of the eCRF. Any clinically significant abnormalities persisting at the end of the study/early withdrawal will be followed by the investigator until resolution or until a clinically stable endpoint is reached.

Efficacy

Response Categories

Disease evaluations will be performed every 28 days on the scheduled assessment day (±3 days). If treatment has been delayed for any reason, then the disease evaluations will be performed according to schedule, regardless of any changes to the dosing regimen.

Disease evaluations will be performed by a central laboratory (unless otherwise specified) according to the Time and Events Schedules until disease progression. This study will use the consensus recommendations for AL amyloidosis treatment response criteria (Comenzo et al., Leukema 26:2317-2325, 2012) presented below. For free light chain assessment, quantitative immunoglobulin, M-protein, and immunofixation measurements in serum and 24 hour urine, the investigator will use results provided by the central laboratory. Subjects with positive serum IFE and confirmed DARZALEX™ (daratumumab) IFE interference, that meet all other clinical criteria for complete response, will be considered CR.

International Uniform Response Criteria Consensus Recommendations

| Hematologic response and progression criteria | |
|---|---|
| Response Category | Criteria |
| Complete | Normalization of free light chain levels and ratio, negative serum and urine immunofixation |
| Very Good Partial | Reduction in the dFLC < 40 mg/L |
| Partial | A greater than 50% reduction in the dFLC |
| No response | Less than a PR |

-continued

Hematologic response and progression criteria

| Response Category | Criteria |
|---|---|
| Progression | From CR, any detectable monoclonal protein or abnormal free light chain ratio (light chain must be double) From PR, 50% increase in serum M-protein to >0.5 g/dl or 50% increase in urine M-protein to >200 mg/day (a visible peak must be present) Free light chain increase of 50% to >100 mg/L |

Abbreviations:
CR, Complete response; dFLC difference between iFLC and uninvolved FLC; FLC free light chain; PR, partial response Example 7

A Randomized Phase 2 Study to Evaluate the Efficacy and Safety of DARZALEX™ (Daratumumab) as a Single Agent for the Treatment of Subjects With Systemic AL Amyloidosis A Phase 2 open-label study evaluating safety and efficacy of DARZALEX™ (daratumumab) as a single agent in subjects with systemic AL amyloidosis who have received treatment previously is conducted.

Approximately 40 subjects are randomized in two cohorts, one receiving DARZALEX™ (daratumumab) and the other one receiving placebo.

Adult patients 18 years or older with biopsy-proven systemic AL amyloidosis who are not in CR or VGPR after initial treatment, Mayo Clinic Cardiac stage I and II patients are included, stage III patients are included only with a NT-proBNP 5000 ng/l (or BNP 1000 ng/l).

Dosing Regimen

Two dosing regimens are considered.

Regimen 1

DARZALEX™ (daratumumab) is dosed 16 mg/kg IV weekly×8 doses, every other week×8 doses and then every 4 weeks until 6 cycles. After 6 cycles patients will continue DARZALEX™ (daratumumab) every 4 weeks until progression or elective discontinuation Regimen 2

Daratumumab is dosed for six 28-day cycles, 16 mg/kg administered by IV route.
For the first cycle, DARZALEX™ (daratumumab) is administered weekly at days 1, 8, 15, and 22
For cycles 2 and 3, DARZALEX™ (daratumumab) is administered every other week at days 1 and 15 1004381
From cycle 4 through 6, DARZALEX™ (daratumumab) is administered every 4 weeks at day 1
Primary objective, secondary objectives, key inclusion criteria and key exclusion criteria are similar to those described in Example 6.

What is claimed is:

1. A method of treating light chain amyloidosis (AL) in a newly diagnosed AL patient, comprising administering to the patient a pharmaceutical composition comprising an anti-CD38 antibody and a hyaluronidase for a time sufficient to treat the AL, wherein:
   a) the anti-CD38 antibody is of an IgG1 isotype comprising a heavy chain variable region (VH) sequence of SEQ ID NO: 4 and a light chain variable region (VL) sequence of SEQ ID NO: 5;
   b) the hyaluronidase is rHuPH20 recombinant hyaluronidase; and
   c) the pharmaceutical composition is administered in combination with cyclophosphamide, bortezomib and dexamethasone (CyBorD).

2. The method of claim 1, wherein the anti-CD38 antibody and CyBorD are administered simultaneously.

3. The method of claim 1, wherein the anti-CD38 antibody and CyBorD are administered sequentially or separately.

4. The method of claim 1, wherein the cyclophosphamide, the bortezomib and the dexamethasone are administered simultaneously.

5. The method of claim 1, wherein the cyclophosphamide, the bortezomib and the dexamethasone are administered sequentially or separately.

6. The method of claim 1, wherein the patient is undergoing hematopoietic stem cell transplantation (HSCT).

7. The method of claim 6, wherein the HSCT is allogeneic.

8. The method of claim 6, wherein the HSCT is autologous or syngeneic.

9. The method of claim 6, wherein the HSCT comprises transplantation of blood stem cells derived from bone marrow, blood or amniotic fluid.

10. The method of claim 6, wherein the anti-CD38 antibody is administered prior to HSCT.

11. The method of claim 6, wherein the anti-CD38 antibody is administered during or after HSCT.

12. The method of claim 6, wherein the patient has completed chemotherapy and/or radiation therapy prior to HSCT.

13. The method of claim 1, wherein the patient is further treated with radiotherapy.

14. The method of claim 1, wherein the anti-CD38 antibody does not mediate killing of CD34-positive hematopoietic progenitor cells by complement dependent cytotoxicity (CDC).

15. The method of claim 1, wherein the anti-CD38 antibody induces killing of CD38 positive plasma cells by antibody-dependent cell-mediated cytotoxicity (ADCC), antibody-dependent cellular phagocytosis (ADCP), complement dependent cytotoxicity (CDC), apoptosis, or modulation of CD38 enzymatic activity.

16. The method of claim 1, wherein the anti-CD38 antibody binds at least to the region SKRNIQFSCKNIYR (SEQ ID NO: 2) and the region EKVQTLEAWVIHGG (SEQ ID NO: 3) of human CD38 SEQ ID NO: 1.

17. The method of claim 1, wherein the anti-CD38 antibody comprises a heavy chain comprising an amino acid sequence that is 95%, 96%, 97%, 98%, 99% or 100% identical to that of SEQ ID NO: 12 and a light chain comprising an amino acid sequence that is 95%, 96%, 97%, 98%, 99% or 100% identical to that of SEQ ID NO: 13.

18. The method of claim 1, wherein the anti-CD38 antibody comprises the heavy chain of SEQ ID NO: 12 and the light chain of SEQ ID NO: 13.

* * * * *